US010752883B2

(12) United States Patent
Brodie

(10) Patent No.: US 10,752,883 B2
(45) Date of Patent: Aug. 25, 2020

(54) GENERATION OF NEURAL STEM CELLS AND MOTOR NEURONS

(71) Applicant: EXOSTEM BIOTEC LTD., Tel Aviv (IL)

(72) Inventor: Chaya Brodie, Southfield, MI (US)

(73) Assignee: EXOSTEM BIOTEC LTD., Tel Aviv (IL)

( * ) Notice: Subject to any disclaimer, the term of this patent is extended or adjusted under 35 U.S.C. 154(b) by 386 days.

(21) Appl. No.: 15/794,137

(22) Filed: Oct. 26, 2017

(65) Prior Publication Data

US 2018/0142208 A1 May 24, 2018

Related U.S. Application Data

(63) Continuation-in-part of application No. 14/380,165, filed as application No. PCT/IB2013/051429 on Feb. 21, 2013, now Pat. No. 9,803,175.

(60) Provisional application No. 61/601,596, filed on Feb. 22, 2012.

(51) Int. Cl.

| | |
|---|---|
| ***C12N 15/11*** | (2006.01) |
| ***C12N 5/00*** | (2006.01) |
| ***A61K 48/00*** | (2006.01) |
| ***C12N 5/0797*** | (2010.01) |
| ***C12N 5/0793*** | (2010.01) |
| ***A61K 35/28*** | (2015.01) |
| ***C12Q 1/6876*** | (2018.01) |
| *C12N 15/113* | (2010.01) |

(52) U.S. Cl.

CPC ............ *C12N 5/0623* (2013.01); *A61K 35/28* (2013.01); *C12N 5/0619* (2013.01); *C12Q 1/6876* (2013.01); *C12N 15/113* (2013.01); *C12N 2310/141* (2013.01); *C12N 2320/11* (2013.01); *C12N 2330/10* (2013.01); *C12N 2501/11* (2013.01); *C12N 2501/115* (2013.01); *C12N 2501/13* (2013.01); *C12N 2501/385* (2013.01); *C12N 2501/41* (2013.01); *C12N 2501/65* (2013.01); *C12N 2501/91* (2013.01); *C12N 2501/998* (2013.01); *C12N 2501/999* (2013.01); *C12N 2506/025* (2013.01); *C12N 2506/08* (2013.01); *C12N 2506/1353* (2013.01); *C12N 2506/1369* (2013.01); *C12N 2506/1384* (2013.01); *C12N 2506/1392* (2013.01); *C12N 2510/00* (2013.01); *C12Q 2600/158* (2013.01); *C12Q 2600/178* (2013.01)

(58) Field of Classification Search

None

See application file for complete search history.

(56) References Cited

U.S. PATENT DOCUMENTS

| | | | |
|---|---|---|---|
| 8,071,562 | B2 | 12/2011 | Bader et al. |
| 8,580,757 | B2 | 11/2013 | Federov et al. |
| 2006/0166362 | A1 | 7/2006 | Dezawa et al. |
| 2008/0171715 | A1 | 7/2008 | Brown et al. |
| 2008/0176328 | A1 | 7/2008 | Chang et al. |
| 2008/0206256 | A1 | 8/2008 | Spong et al. |
| 2008/0241115 | A1 | 10/2008 | Suh et al. |
| 2009/0010895 | A1 | 1/2009 | Often et al. |
| 2010/0003751 | A1 | 1/2010 | Revel et al. |
| 2010/0021434 | A1 | 1/2010 | Melamed et al. |
| 2010/0150947 | A1 | 6/2010 | Siemionow |
| 2011/0311984 | A1 | 12/2011 | Paek et al. |
| 2013/0149288 | A1 | 6/2013 | Slavin et al. |
| 2015/0024966 | A1 | 1/2015 | Brodie et al. |
| 2015/0037298 | A1 | 2/2015 | Brodie et al. |
| 2015/0037299 | A1 | 2/2015 | Brodie et al. |

FOREIGN PATENT DOCUMENTS

| | | |
|---|---|---|
| EP | 1506997 | 2/2005 |
| EP | 1705245 | 9/2006 |
| WO | 2006/134602 | 12/2006 |
| WO | 2009/023525 | 2/2009 |
| WO | 2009/122413 | 10/2009 |
| WO | 2009/144718 | 12/2009 |
| WO | 2010/111522 | 9/2010 |
| WO | 2010/144698 | 12/2010 |
| WO | 2011/030336 | 3/2011 |
| WO | 2011/159075 | 12/2011 |
| WO | 2012/023132 | 2/2012 |
| WO | 2013/124815 | 8/2013 |
| WO | 2013/124816 | 8/2013 |
| WO | 2013/124817 | 8/2013 |

OTHER PUBLICATIONS

Andersson Orom et al., Review Experimental identification of microRNA targets Gene 451 (2010) 1-5.

Antagomir From Wikipedia, the free encyclopedia downloaded Mar. 3, 2017; pp. 1-3.

Krek et al Nat Genet. May 2005; 37(5):495-500. Epub Apr. 3, 2005. Combinatorial microRNA target predictions.

Chen et al. miR-7 and miR-214 are specifically expressed during neuroblastoma differentiation, cortical development and embryonic stem cells differentiation, and control neurite outgrowth in vitroBiochemical and Biophysical Research Communications 394 (2010) 921-927.

(Continued)

*Primary Examiner* — Maria G Leavitt

(74) *Attorney, Agent, or Firm* — The Roy Gross Law Firm, LLC; Roy Gross

(57) ABSTRACT

A method of generating a population of cells useful for treating a brain disorder in a subject is disclosed. The method comprises contacting mesenchymal stem cells (MSCs) with at least one exogenous miRNA having a nucleic acid sequence at least 90% identical to a sequence selected from the group consisting of SEQ ID NOs: 15-19 and 27-35, thereby generating a population of cells and/or generating neurotrophic factors that may provide important signals to damaged tissues or locally residing stem cells. MSCs differentiated by miRs may also secrete miRs and deliver them to adjacent cells and therefore provide important signals to neighboring endogenous normal or malignant cells.

6 Claims, 16 Drawing Sheets

Specification includes a Sequence Listing.

(56) References Cited

OTHER PUBLICATIONS

*Genetic Technologies 2 Limited* v. *Merial L.L.C.*, United States Court of Appeals for the Federal Circuit; 2015-1202, 2015-1203; Decided: Apr. 8, 2016; pp. 1-20.
Lehmann et al. An unconventional role for mi RNA: let-7 activates Toll-like receptor 7 and causes neurodegeneration Nature Neuroscience 15,827-835(2012).
Roush et al. Review the let-7 family of microRNAs Trends in Cell Biology vol. 18, Issue 10, Oct. 2008, pp. 505-516.
Collino et al. Microvesicles Derived from Adult Human Bone Marrow and Tissue Specific Mesenchymal Stem Cells Shuttle Selected Pattern of miRNAs PLoS One. 201 O; 5(7): e11803.
Krichevsky Specific MicroRNAs Modulate Embryonic Stem Cell-Derived Neurogenesis Stem Cells. Apr. 2006; 24(4): 857-864.
DataSheet GeneChip® mi RNA 4.0 Array Affymetrix® mi RNA 4.1 Array Strip (Affymetrix, Santa Clara, CA, USA) downloaded Nov. 6, 2015.
Raghavachari et al., Integrated analysis of miRNA and mRNA during differentiation of human CD34+ cells delineates the regulatory roles of microRNA in hematopoiesis Experimental Hematology vol. 42, Issue 1, Jan. 2014, pp. 14-27.e2.
Smirnova Regulation of miRNA expression during neural cell specification European Journal of Neuroscience, vol. 21, pp. 1469-1477,2005.
Sasportas et al. "Assessment of Therapeutic Efficacy and Fated of Engineered Human Mesenchymal Stem Cells for Cancer Therapy", Proc. Natl. Acad. Sci. USA, PNAS, 106(12): 4322-4327, Mar. 24, 2009.
Akkerblom et al. "Functional Studies of MicroRNAs in Neural Stem Cells: Problems and Perspectives", Frontiers in Neuroscience, XP055074176, 6(Art.14): 1-10, Feb. 2012.
Gao "Context-Dependent Functions of Specific MicroRNAs in Neuronal Development", Neuronal Development, XP021081673, 5(25): 1-9, Oct. 2010.
Gong et al. "Innnortalized Mesenchymal Stem Cells: An Alternative to Primary Mesenchymal Stem Cells in Neuronal Differentiation and Neurogeneration Associated Studies", Journal of Biomedical Science, XP021 II 1456, 18(87): 1-16, Nov. 25, 2011.
Kang et al. "Kaposi's Sarcoma-Associated Herpesvirus ORF57 Promotes Escape of Viarl and Human Interleukin-6 From MicroRNA-Mediated Suppression", Journal of Virology, XP055073965, 85(6): 2620-2630, Mar. 2011.
Karaoz et al. "Human Dental Pulp Stem Cells Demonstrate Better Neural and Epithelial Stem Cell Properties Than Bone Marrow-Derived Mesenchymal Stem Cells", Histochemistry and Cell Biology, XP055074788, 136(4): 455-473, Oct. 31, 2011.
Katsushima et al. "Contribution of MicroRNA-127 5 to Claudin 11 Protein Suppression Via a Polycomb-Mediated Silencing Mechanism in Human Glioma Stem-Like Cells", The Journal of Biological Chemistry, XP055074166, 287(33): 27396-27406, Aug. 10, 2012.
Kim et al. "A Development Taxonomy of Gliobastoma Defined and Maintained by MicroRNAs", Cancer Research, XP055073956, 71(9): 3387-3399, May 2011.
Kosztowski et al. "Applications of Neural and Mesenchymal Stem Cells in the Treatment of Gliomas", Expert Review of Anticancer Therapy, 9(5): 597-612, May 2009.
Lakshrnipathy et al. "Concise Review: MicroRNA Expression in Multipotent Mesenchyrnal Stromal Cells", Stern Cells, 26: 356-363, 2008. p. 356, Abstract, p. 357, Left col., Para 5, p. 358, Right col., Table 2, Para 2, p. 359, Left col., Para 4, Right col., Last Para, p. 360, Right col., Para 2.
Letzen et al. "MicroRNA Expression Profiling of Oligodendrocyte Differentiation From Human Embryonic Stem Cells", PLoS ONE, XP055091734, 5(5): e-10480-1-e10480-12, May 2010. p. 2, col. 2, Para 2, Fig.2, Table 1.
Liu et al. "Induction of Oligodendrocyte Differentiation by Olig2 and Sox10: Evidence for Reciprocal Interactions and Dosage-Dependent Mechanisms", Developmental Biology, 302: 683-693, 2007.
Liu et al. "MicroRNAs Regulation Modulated Self-Renewal and Lineage Differentiation of Stern Cells", Cell Transplantation, XP002605501, 18(9): 1039-1045, Jan. 2009.
Luo et al. "Connective Tissue Growth Factor (CTGF) Is Regulated by Wnt and Bone Morphogenetic Proteins Signaling in Osteoblast Differentiation of Mesenchyrnal Stern Cells", The Journal of Biological Chemistry, 279(53): 55958-55968, Dec. 31, 2004. p. 55958, Abstract, p. 55967, Fig. 7.
Maisel et al. "Genome-Wide Expression Profiling and Functional Network Analysis Upon Neuroectodermal Conversion of Human Mesenchymal Stern Cells Suggest HIF-1 and MiR-124a as Important Regulators", Experimental Cell Research, XP055074156, 316(17): 2760-2778, Oct. 2010.
Nakamizo et al. "Human Bone Marrow-Derived Mesenchymal Stem Cells in the Treatment of Gliomas", Cancer Research, 65(8): 3307-3318, Apr. 15, 2005.
Ozata et al. "The Role of MicroRNA Deregulation in the Pathogenesis of Adrenocortical Carcinoma", Endocrine-Related Cancer, XP055074 I 62, 18( 6): 643-655, Oct. 27, 2011.
Phillips et al. "Genetic Modification of Stern Cells for Transplantation", Advanced Drug Delivery Reviews, 60(2): 160-172, Jan. 14, 2008.
Riggi et al. "EWS-FLI-1 Modulates MiRNA145 and SOX2 Expression to Initiate Mesenchymal Stern Cell Reprogramming Toward Ewing Sarcoma Cancer Stern Cells", Genes & Development, 24: 916-932, 2010.
Shookhoff et al. "The Emerging Role of MicroRNAs in Adult Stem Cells", Adult Stem Cells: Biology and Methods of Analysis, XP008163996, Chap.3: 57-97, 2011.
Silber et al. "MiR-124 and MiR-137 Inhibit Proliferation of Glioblastoma Multiforme Cells and Induce Differentiation of Brain Tumor Stem Cells", BMC Medicine, 6(14): 1-17, Jun. 24, 2008.
Song et al. "Connective Tissue Growth Factor (CTGF) Acts as a Downstream Mediator of TGF-Betal to Induce Mescnchymal Cell Condensation", Journal of Cellular Physiology, 210: 398-410, 2007. p. 398, Abstract, p. 399, Left col. Para 2, p. 402, Fig.2, p. 405, Right col., Para 1.
Xin et al. "Exosome-Mediated Transfer ofMiR-133b From Multipotent Mesenchymal Stromal Cells to Neural Cells Contributes to Neurite Outgrowth", Stem Cells, XP055073957, 30(7): 1556-1564, Jul. 18, 2012.
Zhang et al. "Isolation and Characterization of Mesenchymal Stern Cells Derived From Bone Marrow Patients With Parkinson's Disease", In Vitro Cellular & Developmental Biology—Animal, XP055074787, 44(5-6): 169-177, Jun. 2008.
Zhao et al. "MicroRNA-Mediated Control of Oligodendrocyte Differentiation", Neuron, XP055091729, 65(5): 612-626, Mar. 11, 2010. p. 613, col. 2, Para 2, Figs.3, 4.

MSC-derived NSCs

MSCs

Control

Treatment

Neural progenitor cells

Motor neurons

Stem cell-related miRNAs

Neuronal-related miRNAs

Hematopoietic-related miRNAs

GENERATION OF NEURAL STEM CELLS AND MOTOR NEURONS

CROSS REFERENCE TO RELATED APPLICATIONS

This application is a Continuation-in-Part of U.S. patent application Ser. No. 14/380,165 filed on Aug. 21, 2014 (now U.S. Pat. No. 9,803,175) and titled “Generation of Neural Stem Cells and Motor Neurons”, which is a national phase of PCT Patent Application No. PCT/IB2013/051429 filed on Feb. 21, 2013, which claims the benefit of priority of U.S. Provisional Patent Application No. 61/601,596 filed on Feb. 22, 2012. The contents of the above applications are all incorporated by reference as if fully set forth herein in their entirety.

FIELD AND BACKGROUND OF THE INVENTION

The present invention, in some embodiments thereof, relates to methods of ex vivo differentiating mesenchymal stem cells towards neural stem cells and motor neurons using microRNAs (miRNAs).

Mesenchymal stem cells (MSCs) are a heterogeneous population of stromal cells that can be isolated from multiple species, residing in most connective tissues including bone marrow, adipose, placenta, umbilical cord and perivascular tissues. MSCs can also be isolated from the placenta, amniotic fluid and cord’s Wharton’s jelly.

The concentration of MSCs in all tissues, including bone marrow and adipose tissue is very low but their number can be expanded in vitro. Typically, expansion of MSCs using up to 15 passages does not result in mutations indicating genetic stability. MSC can differentiate into cells of the mesenchymal lineage, such as bone, cartilage and fat but, under certain conditions, have been reported to acquire the phenotype of cells of the endodermal and neuroectodermal lineage, suggesting some potential for “trans-differentiation”.

Within the bone marrow compartment, these cells are tightly intermingled with and support hematopoiesis and the survival of hematopoietic stem cells in acquiescent state (7). In addition, after expansion in culture, MSCs retain their ability to modulate innate and adaptive immunity (8). Furthermore, MSCs migrate actively to sites of inflammation and protect damaged tissues, including the CNS, properties that supported their use as new immunosuppressive or rather immunoregulatory or anti-inflammatory agents for the treatment of inflammatory and immune-mediated diseases including autoimmune disorders (9). These features of MSCs merited their use to control life-threatening graft-versus-host-disease (GVHD) following allogeneic bone marrow transplantation, thus controlling one of the most serious complications of allogenic bone marrow transplantation, helping to lower transplant-related toxicity and mortality associated with multi-system organ injury (10).

Several studies have shown that MSCs following exposure to different factors in vitro, change their phenotype and demonstrate neuronal and glial markers [Kopen, G. C., et al., Proc Natl Acad USA. 96(19):10711-6, 1999; Sanchez-Ramos, et al. Exp Neurol. 164(2):247-56. 2000; Woodbury, D., J Neurosci Res. 61(4):364-70,2000; Woodbury, D., et al., J Neurosci Res. 69(6):908-17, 2002; Black, I. B., Woodbury, D. Blood Cells Mol Dis. 27(3):632-6, 2001; Kohyama, J., et al. Differentiation. 68(4-5):235-44, 2001; Levy, Y. S. J Mol Neurosci. 21(2):121-32, 2003].

Accordingly, MSCs (both ex-vivo differentiated and non-differentiated) have been proposed as candidates for cell replacement therapy for the treatment of various neurological disorders including multiple sclerosis, Parkinson’s disease, ALS, Alzheimer’s disease, spinal cord injury and stroke.

Motor neurons in the spinal cord innervate skeletal muscles, and originate from neuroepithelial cells in a restricted area of the developing spinal cord (neural tube). During embryonic development, motor neurons extend their processes (nerves) to the periphery to innervate skeletal muscles that are adjacent to the spinal cord. In an adult human body, however, motor neuron’s axons are projected large distances away from the cell bodies in the spinal cord to reach their target muscles. Because of this, motor neurons have a higher metabolic rate compared to smaller neurons, and this renders them more susceptible to genetic, epigenetic, and environmental changes. Motor neurons cannot renew themselves and therefore their loss or degeneration are generally associated with fatal neurological conditions including paralysis and disorders such as pediatric spinal muscular atrophy (SMA) and adult onset amyotrophic lateral sclerosis (ALS).

Roy et al., 2005 [Exp Neural. 2005; 196:224-234]; Zhang et al., 2006 [Stem Cells. 2006; 24:434-442]; Bohl et al., 2008 [Stem Cells. 2008; 26:2564-2575]; and Dimos et al., 2008 [Science. 2008; 321:1218-1221] the contents of which are incorporated by reference teach genetic modification of different stem cells to induce differentiation into motor neurons.

SUMMARY OF THE INVENTION

According to an aspect of some embodiments of the present invention there is provided a method of predisposing mesenchymal stem cells to differentiate into neural stem cells, the method comprising up-regulating a level of at least one exogenous miRNA selected from the group consisting of miR-1275, miR-891a, miR-154, miR-1202, miR-572, miR-935a, miR302b, miR-371, miR-134, miR-219, miR-155, miR-32, miR-33, miR-126, miR-127, miR-132, let-7c, miR-665, miR-4258, miR-361-3p, miR-374a-star, miR-892b, miR-361-5p, miR-181a, miR-16, miR-636, miR-4284, miR-1208, miR-1274b, miR-30c-2-star, miR-501-3p, hsa-miR-92a, miR-378b, miR-1287, miR-425-star, miR-324-5p, miR-3178, miR-219-1-3p, miR-197, miR-181b, miR-500-star, miR-106b, miR-502-3p, miR-30c, miR-1275, miR-422a, miR-93, miR-181d, miR-1307, miR-1301, miR-99a, miR-505-star, miR-1202, miR-12, miR-532-5p, miR-195, miR-532-3p, miR-106a, miR-17, miR-1271, miR-769-3p, miR-15b, miR-324-3p, miR-20a, miR-501-5p, miR-330-3p, miR-874, miR-500, miR-25, miR-769-5p, miR-125b-2-star, miR-130b, miR-504, miR-181a-2-star, miR-885-3p, miR-1246, miR-92b, miR-362-5p, miR-572, miR-4270, miR-378c, miR-93-star, miR-149, miR-363, miR-9, miR-18a, miR-346, miR-497, miR-378, miR-1231, miR-139-5p, miR-3180-3p, miR-935 and miR-20b in the mesenchymal stem cells (MSCs), thereby predisposing the MSCs to differentiate into the neural stem cells.

According to an aspect of some embodiments of the present invention there is provided a method of predisposing MSCs to differentiate into neural stem cells, the method comprising down-regulating an expression of at least one miRNA selected from the group consisting of miR-4317, miR-153, miR-4288, miR-409-5p, miR-193a-5p, miR-1Ob, miR-142-3p, miR-131a, miR-125b, miR-181a, miR-145, miR-143, miR-214, miR-199a-3p, miR-199a-5p, miR-199b-

3p, miR-138, miR-31, miR-21, miR-193a-5p, miR-224-star, miR-196a, miR-487b, miR-409-5p, miR-193b-star, miR-379, miR-21-star, miR-27a-star, miR-27a, miR-4317, miR-193b, miR-27b, miR-22, 574-3p, miR-4288, miR-23a, miR-221-star, miR-2113, let-7i, miR-24, miR-23b, miR-299-3p, miR-518c-star, miR-221, miR-431-star, miR-523, miR-4313, miR-559, miR-614, miR-653, miR-2278, miR-768-5p, miR-154-star, miR-302a-star, miR-3199 and miR-3137 in the mesenchymal stem cells by up-regulating a level of at least one polynucleotide agent that hybridizes and inhibits a function of the at least one miRNA thereby predisposing the MSCs to differentiate into the neural stem cells.

According to an aspect of some embodiments of the present invention there is provided a method of predisposing MSCs to differentiate into neural stem cells, the method comprising up-regulating a level of exogenous miR-124 in the mesenchymal stem cells (MSCs) and down-regulating a level of miR-let-7 in the MSCs, thereby predisposing the MSCs to differentiate into the neural stem cells.

According to an aspect of some embodiments of the present invention there is provided a method of predisposing MSCs to differentiate into neural stem cells, the method comprising contacting the mesenchymal stem cells (MSCs) with an agent that down-regulates an amount and/or activity of Related to testis-specific, vespid and pathogenesis protein 1 (RTVP-1), thereby predisposing MSCs to differentiate into the neural stem cells.

According to an aspect of some embodiments of the present invention there is provided a method of predisposing neural stem cells to differentiate into motor neurons, the method comprising up-regulating a level of at least one exogenous miRNA selected from the group consisting of miR-368, miR-302b, miR-365-3p, miR-365-5p, miR-Let-7a, miR-Let-7b, miR-218, miR-134, miR-124, miR-125a, miR-9, miR-154, miR-20a and miR-130a in neural stem cells (NSCs), thereby predisposing NSCs to differentiate into the motor neurons.

According to an aspect of some embodiments of the present invention there is provided a method of predisposing MSCs to differentiate into motor neurons, the method comprising up-regulating a level of at least one exogenous miRNA selected from the group consisting of miR-648, miR-368, miR-365, miR-500, miR-491, miR-218, miR-155, miR-192, let-7b, miR-16, miR-210, miR-197, miR-21, miR-373, miR-27a, miR-122, miR-17, miR-494, miR-449, miR-503, miR-30a, miR-196a, miR-122, miR-7, miR-151-5p, miR-16, miR-22, miR-31, miR-424, miR-1, miR-29c, miR-942, miR-100, miR-520, miR-663a, miR-562, miR-449a, miR-449b-5p, miR-520b, miR-451, miR-532-59, miR-605, miR-504, miR-503, miR-155, miR-34a, miR-16, miR-7b, miR-103, miR-124, miR-1385p, miR-16, miR-330, miR-520, miR-608, miR-708, miR-107, miR-137, miR-132, miR-145, miR-204, miR-125b, miR-224, miR-30a, miR-375, miR-101, miR-106b, miR-128, miR-129-5p, miR-153, miR-203, miR-214, miR-338-3p, miR-346, miR-98, miR-107, miR-141, miR-217, miR-424, miR-449, miR-7, miR-9, miR-93, miR-99a, miR-100, miR-1228, miR-183, miR-185, miR-190, miR-522, miR-650, miR-675, miR-342-3p, miR-31 in the mesenchymal stem cells (MSCs), thereby predisposing MSCs to differentiate into the motor neurons.

According to an aspect of some embodiments of the present invention there is provided a method of predisposing NSCs to differentiate into motor neurons, the method comprising down-regulating an expression of at least one miRNA selected from the group consisting of miR-372, miR-373, miR-141, miR-199a, miR-32, miR-33, miR-221 and miR-223 by up-regulating a level of at least one polynucleotide agent that hybridizes and inhibits a function of the at least one miRNA in the NSCs thereby predisposing NSCs to differentiate into the motor neurons.

According to an aspect of some embodiments of the present invention there is provided a method of predisposing MSCs to differentiate into motor neurons, the method comprising down-regulating an expression of at least one miRNA selected from the group consisting of miR-372, miR-373, miR-942, miR-2113, miR-199a-3p, miR-199a-5p, miR-372, miR-373, miR-942, miR-2113, miR-301a-3p, miR-302c, miR-30b-5p, miR-30c, miR-326, miR-328, miR-331-3p, miR-340, miR-345, miR-361-5p, miR-363, miR-365a-3p, miR-371a-3p, miR-373-3p, miR-374a, miR-423-3p, miR-449b-5p, miR-451a, miR-494, miR-504, miR-515-3p, miR-516a-3p, miR-519e, miR-520a-3p, miR-520c-3p, miR-520g, miR-532-5p, miR-559, miR-562, miR-572, miR-590-5p, miR-605, miR-608, miR-626, miR-639, miR-654-3p, miR-657, miR-661, miR-708-5p, miR-942, miR-96, miR-99amo and miR-194 by up-regulating a level of at least one polynucleotide agent that hybridizes and inhibits a function of the at least one miRNA in the MSCs thereby predisposing MSCs to differentiate into the motor neurons.

According to an aspect of some embodiments of the present invention there is provided a genetically modified isolated population of cells which comprise at least one exogenous miRNA selected from the group consisting of miR302b, miR-371, miR-134, miR-219, miR-154, miR-155, miR-32, miR-33, miR-126, miR-127, miR-132 and miR-137 and/or which comprise at least one polynucleotide agent that hybridizes and inhibits a function of at least one miRNA selected from the group consisting of miR-10b, miR-142-3p, miR-131a, miR-125b, miR-153 and miR-181a, wherein the cells have a neural stem cell phenotype.

According to an aspect of some embodiments of the present invention there is provided a genetically modified isolated population of cells which comprise at least one exogenous miRNA selected from the group consisting of miR-368, miR-302b, miR-365-3p, miR-365-5p, miR-Let-7a, miR-Let-7b, miR-218, miR-134, miR-124, miR-125a, miR-9, miR-154, miR-20a, miR-130a and/or which comprise at least one polynucleotide agent that hybridizes and inhibits a function of at least one miRNA selected from the group consisting of miR-372, miR-373, miR-141, miR-199a, miR-32, miR-33, miR-221 and miR-223, wherein the cells have a motor neuron phenotype.

According to an aspect of some embodiments of the present invention there is provided a method of treating a brain disease or disorder in a subject in need thereof, the method comprising administering to the subject a therapeutically effective amount of the isolated population of cells of claim 33, thereby treating the brain disease or disorder.

According to an aspect of some embodiments of the present invention there is provided a pharmaceutical composition comprising the isolated population of cells described herein and a pharmaceutically acceptable carrier.

According to an aspect of some embodiments of the present invention there is provided a method of selecting a miRNA which may be regulated for the treatment of a motor neuron disease comprising:

(a) differentiating a population of neural stem cells towards a motor neuron phenotype; and (b) analyzing a change in expression of a miRNA in the population of MSCs prior to and following the differentiating of the MSCs towards a motor neuron phenotype, wherein a change of expression of a miRNA above or below a predetermined level is indicative that the miRNA may be regulated for the treatment of the motor neuron disease.

According to an aspect of some embodiments of the present invention there is provided a method of treating a motor neuron disease in a subject in need thereof, the method comprising administering to the subject a therapeutically effective amount of the isolated population of cells of claim 35, thereby treating the brain disease or disorder.

According to an aspect of some embodiments of the present invention there is provided a genetically modified isolated population of cells which comprise at least one exogenous miRNA selected from the group consisting of miR-1275, miR-891a, miR-154, miR-1202, miR-572 and miR-935a and/or which comprise at least one polynucleotide agent that hybridizes and inhibits a function of at least one miRNA selected from the group consisting of miR-4317, miR-153, miR-4288, miR-409-5p, miR-193a-5p, wherein said cells have a neural stem cell phenotype.

According to an aspect of some embodiments of the present invention there is provided a genetically modified isolated population of cells which comprise at least one exogenous miRNA selected from the group consisting of miR-648, miR-368, miR-365, miR-500 and miR-491 and/or which comprise at least one polynucleotide agent that hybridizes and inhibits a function of at least one miRNA selected from the group consisting of miR-372, miR-373, miR-942, miR-2113, miR-199a-3p and miR-199a-5p, wherein said cells have a motor neuron phenotype.

According to some embodiments of the invention, the at least one exogenous miRNA is selected from the group consisting of miR-1275, miR-891a, miR-154, miR-1202, miR-572 and miR-935a.

According to some embodiments of the invention, the at least one exogenous miRNA is selected from the group consisting of miR-20b, miR-925, miR-891 and miR-378.

According to some embodiments of the invention, the at least one miRNA is selected from the group consisting of miR-4317, miR-153, miR-4288, miR-409-5p, and miR-193a-5p.

According to some embodiments of the invention, the at least one miRNA is selected from the group consisting of miR-138, miR-214, miR-199a and miR-199b.

According to some embodiments of the invention, the at least one miRNA is miR-138, the method further comprises:

(i) down-regulating an expression of miR-891 using a polynucleotide agent that hybridizes and inhibits the function of miR-891;

(ii) up-regulating a level of exogenous miR20b; or (iii) up-regulating a level of exogenous miR378.

According to some embodiments of the invention, the miRNA is selected from the group consisting of miR-648, miR-368, miR-365, miR-500 and miR-491.

According to some embodiments of the invention, the miRNA is selected from the group consisting of miR-372, miR-373, miR-942, miR-2113, miR-199a-3p and miR-199a-5p.

According to some embodiments of the invention, the at least one miRNA comprises each of miR Let-7a, miR-124, miR-368 and miR-154.

According to some embodiments of the invention, the at least one miRNA comprises each of miR-125a, miR-9 and miR-130a.

According to some embodiments of the invention, the at least one miRNA comprises each of miR-218, miR-134 and miR-20a.

According to some embodiments of the invention, the method further comprises down-regulating each of miR-141, miR-32, miR-33, miR-221, miR-223 and miR-373.

According to some embodiments of the invention, the NSCs are generated by ex vivo differentiating MSCs.

According to some embodiments of the invention, the ex vivo differentiating is affected according to any of the methods described herein.

According to some embodiments of the invention, the MSCs are isolated from a tissue selected from the group consisting of bone marrow, adipose tissue, placenta, cord blood and umbilical cord.

According to some embodiments of the invention, the MSCs are autologous to the subject.

According to some embodiments of the invention, the MSCs are non-autologous to the subject.

According to some embodiments of the invention, the MSCs are semi-allogeneic to the subject.

According to some embodiments of the invention, the up-regulating comprises introducing into the MSCs the at least one miRNA.

According to some embodiments of the invention, the up-regulating is affected by transfecting the MSCs with an expression vector which comprises a polynucleotide sequence which encodes a pre-miRNA of the at least one miRNA.

According to some embodiments of the invention, the up-regulating is affected by transfecting the MSCs with an expression vector which comprises a polynucleotide sequence which encodes the at least one miRNA.

According to some embodiments of the invention, the method further comprises analyzing an expression of at least one marker selected from the group consisting of nestin and Sox2 following the generating.

According to some embodiments of the invention, the method further comprises analyzing an expression of at least one marker selected from the group consisting of Islet1, HB9 and the neuronal markers neurofilament and tubulin following the generating.

According to some embodiments of the invention, the method is effected in vivo. According to some embodiments of the invention, the method is effected ex vivo.

According to some embodiments of the invention, at least 50% of the population of cells express at least one marker selected from the group consisting of nestin and Sox2.

According to some embodiments of the invention, the at least 50% of the population of cells express at least one marker selected from the group consisting of Islet1, HB9 and the neuronal markers neurofilament and tubulin.

According to some embodiments of the invention, the isolated population of cells is for use in treating a brain disease or disorder.

According to some embodiments of the invention, the isolated population of cells is for brain disease or disorder is a neurodegenerative disorder.

According to some embodiments of the invention, the neurodegenerative disorder is selected from the group consisting of multiple sclerosis, Parkinson's, epilepsy, amyotrophic lateral sclerosis (ALS), stroke, Rett Syndrome, autoimmune encephalomyelitis, spinal cord injury, cerebral palsy, stroke, Alzheimer's disease and Huntingdon's disease.

According to some embodiments of the invention, the isolated population is for use in treating a motor neuron disease.

According to some embodiments of the invention, the motor neuron disease is selected from the group consisting of amyotrophic lateral sclerosis (ALS), primary lateral sclerosis (PLS), pseudobulbar palsy and progressive bulbar palsy.

According to some embodiments of the invention, the nerve disease or disorder is a neurodegenerative disorder.

According to some embodiments of the invention, the neurodegenerative disorder is selected from the group consisting of multiple sclerosis, Parkinson's, epilepsy, amyotrophic lateral sclerosis (ALS), stroke, Rett Syndrome, autoimmune encephalomyelitis, spinal cord injury, cerebral palsy, stroke, Alzheimer's disease and Huntingdon's disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

Figure 1A:
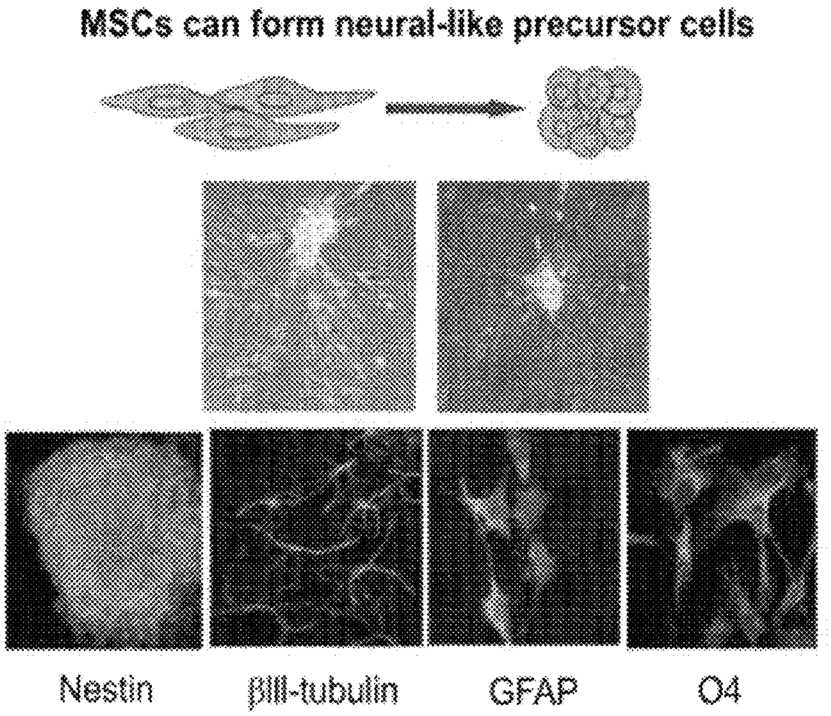
FIGS. 1A-B are photographs and graphs illustrating that mesenchymal stem cells (MSCs) may be induced to differentiate to neural stem cell (NSC)-like cells and express NSC markers. MSCs were plated in neurosphere medium on bacteria dishes as described in Methods.

The MSC-derived spheroids were characterized by immunofluorescence (FIG. 1A) and real-time PCR (FIG. 1 B).

Figure 2:
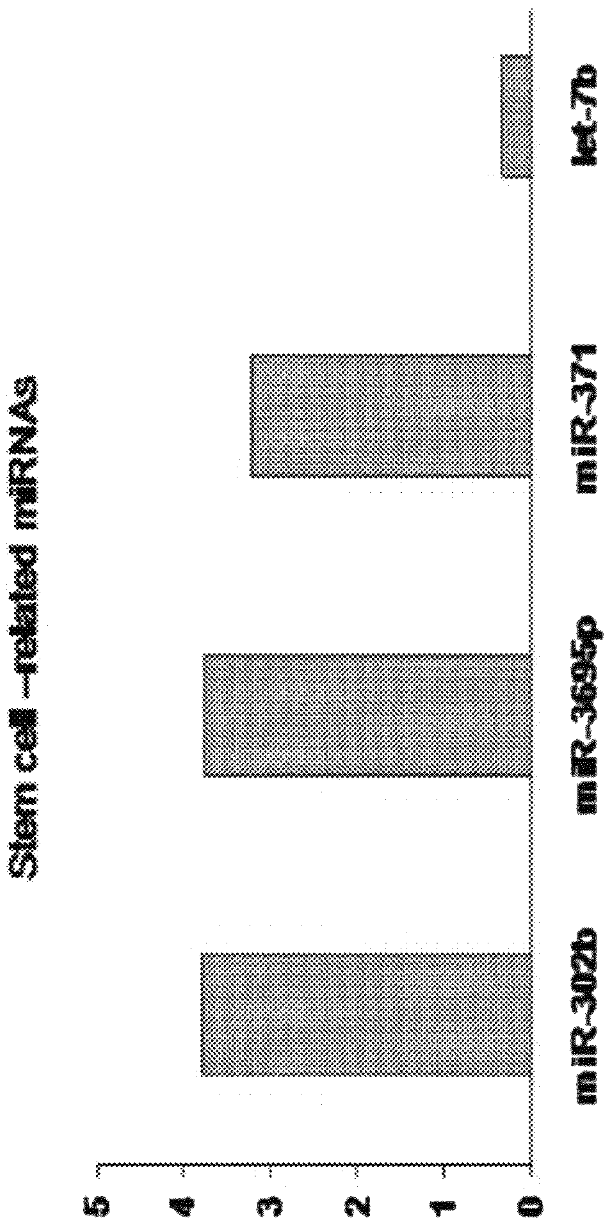

FIG. 2 is a bar graph illustrating exemplary miRNAs associated with stem cell signature and self renewal that were up-regulated during NSC differentiation.

Figure 3:
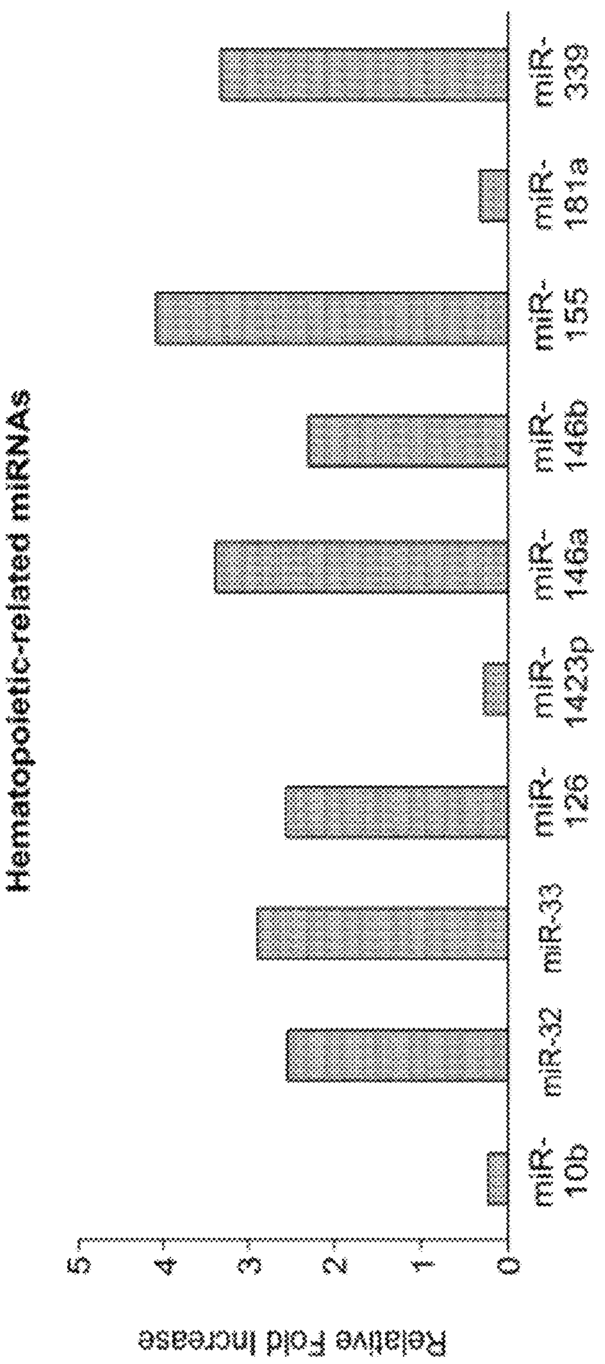

FIG. 3 is a bar graph illustrating exemplary miRNAs associated with hematopoiesis that were up-regulated during NSC differentiation.

FIGS. 4A-D are bar graphs illustrating exemplary miRNAs associated with a neuronal signature and self renewal that were up-regulated (FIGS. 4A-C) or down-regulated (FIG. 4D) during NSC differentiation.

Figure 4A:
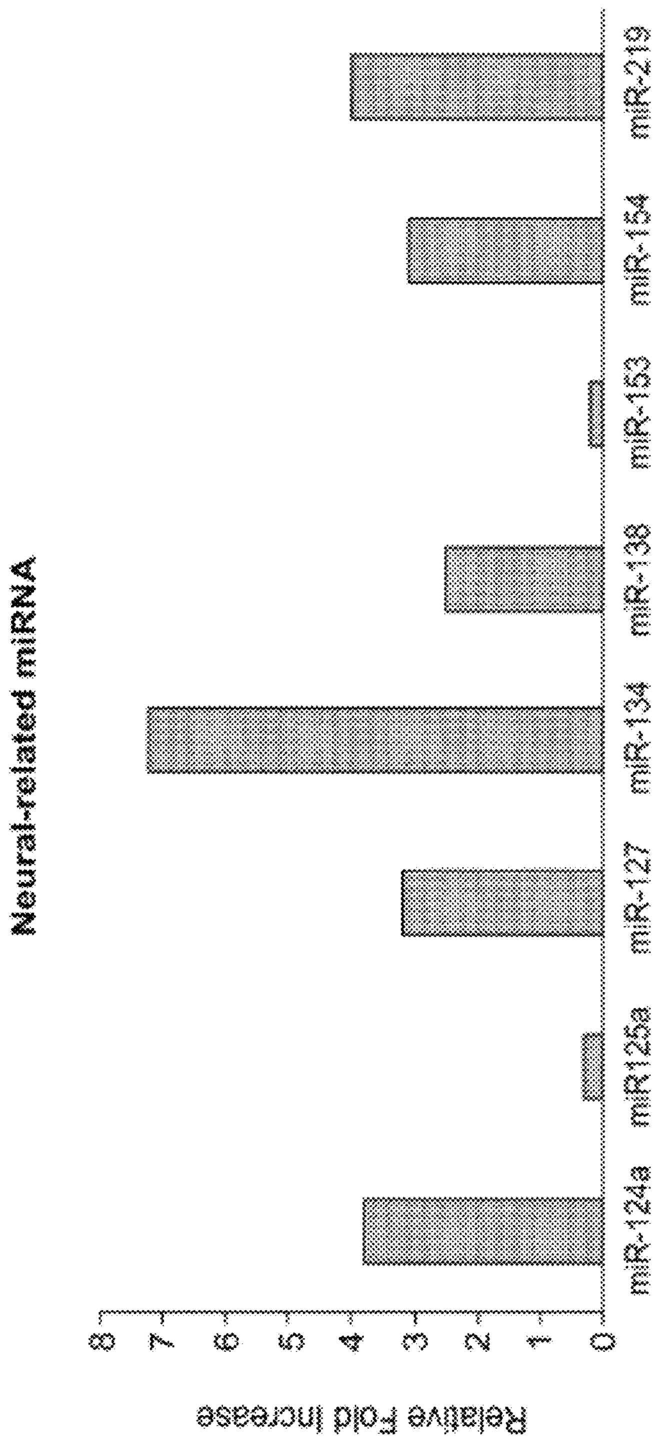
Figure 4B:
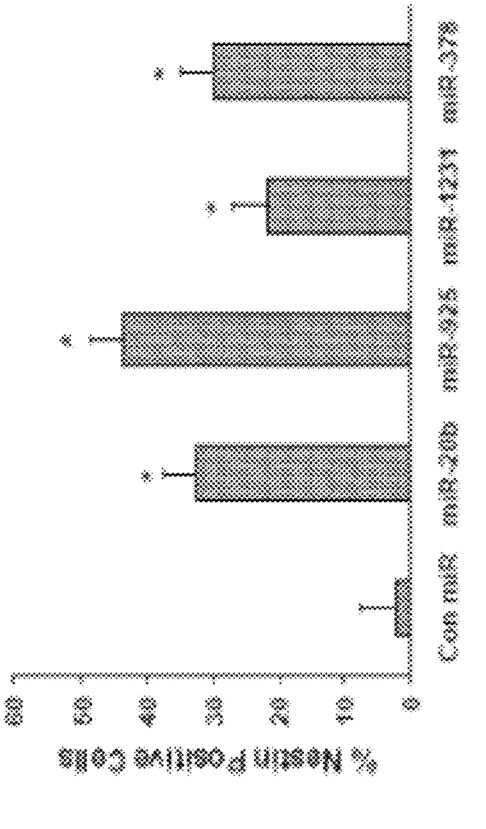
Figure 4C:
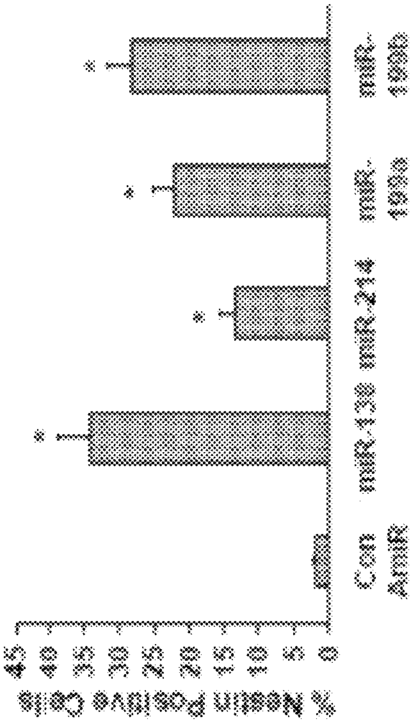
Figure 4D:
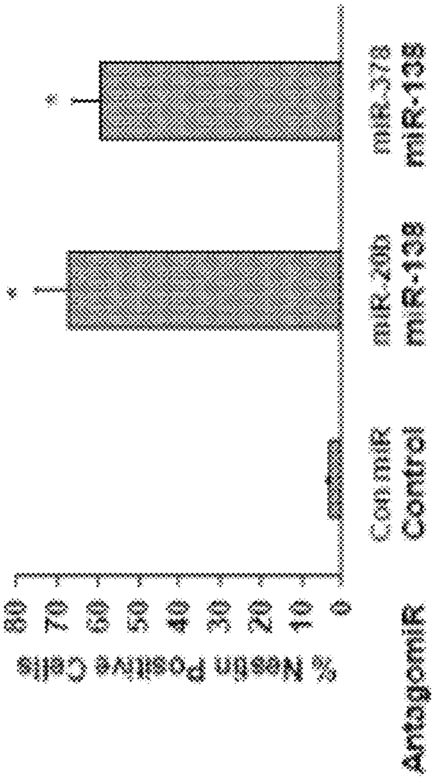
Figure 4F:
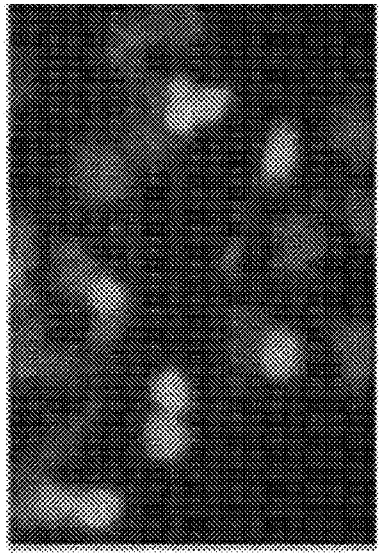
Figure 4E:
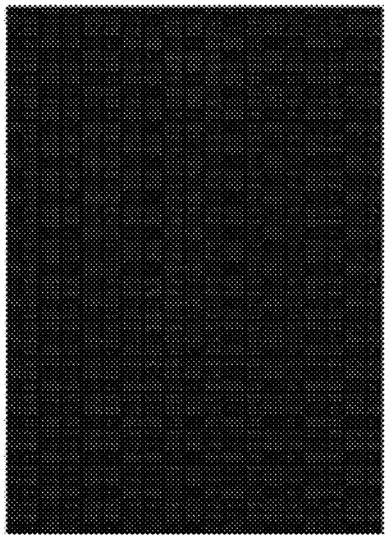

FIGS. 4E-F are photographs illustrating bone marrow MSCs transfected with antagomiR-138 and miR-891 using a nestin promoter reporter assay.

FIGS. 5A-D are graphs and photographs illustrating that RTVP-1 plays a role in differentiation of MSCs towards NSCs. RTVP-1 is expressed in high levels in BM-MSCs, similar to some glioma cells that are considered as the cells that expressed the highest levels of this protein, as determined by Western blot analysis (A). A diagram showing the mesenchymal lineage differentiation of MSCs (B). Silencing of RTVP-1 in BM-MSCs using siRNA duplexes decreases the osteogenic differentiation of these cells (C). Silencing of RTVP-1 in BM-MSCs decreases the expression of the different mesenchymal markers (D).

Figure 5A:
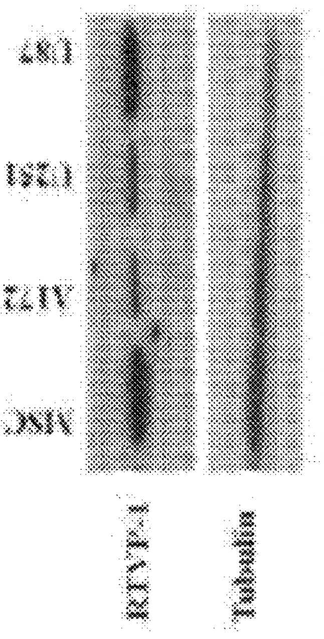
Figure 5B:
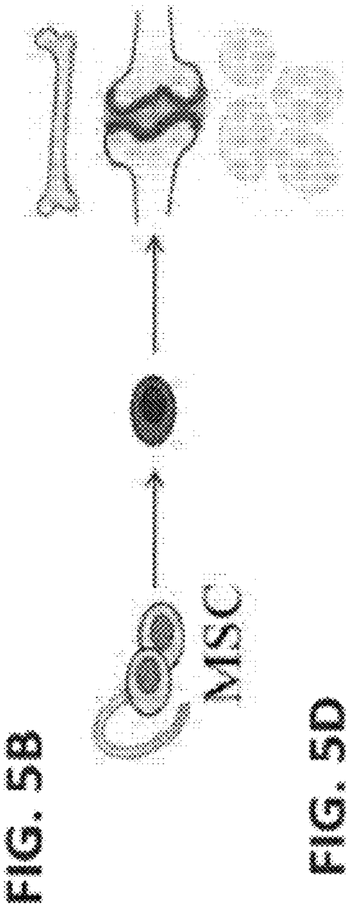
Figure 5C:
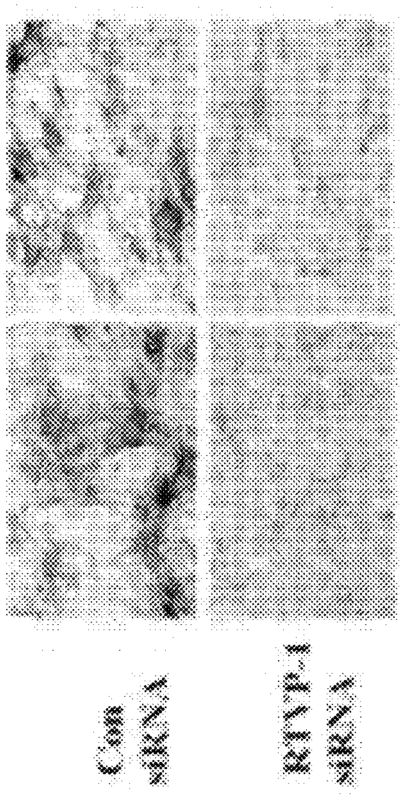
Figure 5D:
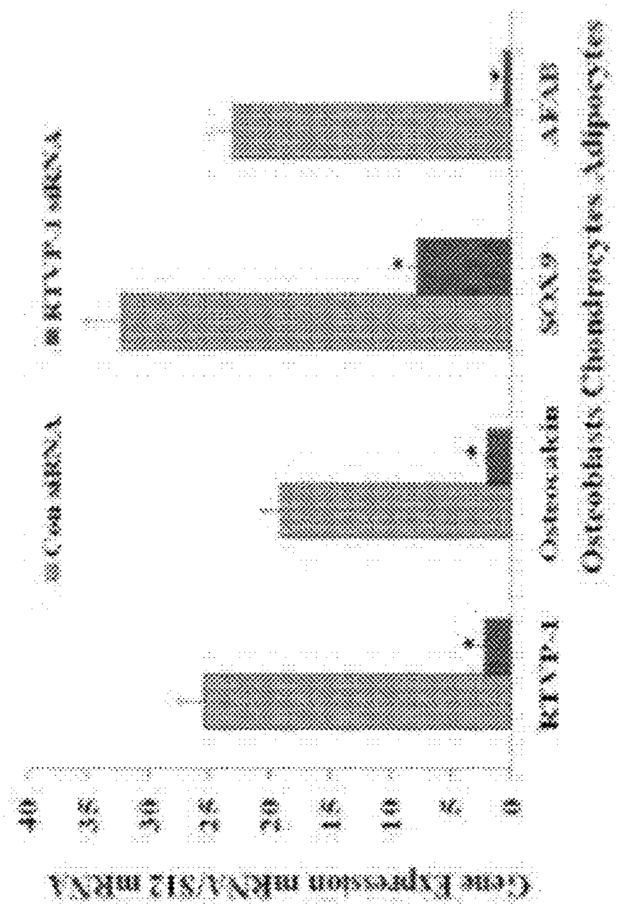
Figure 5F:
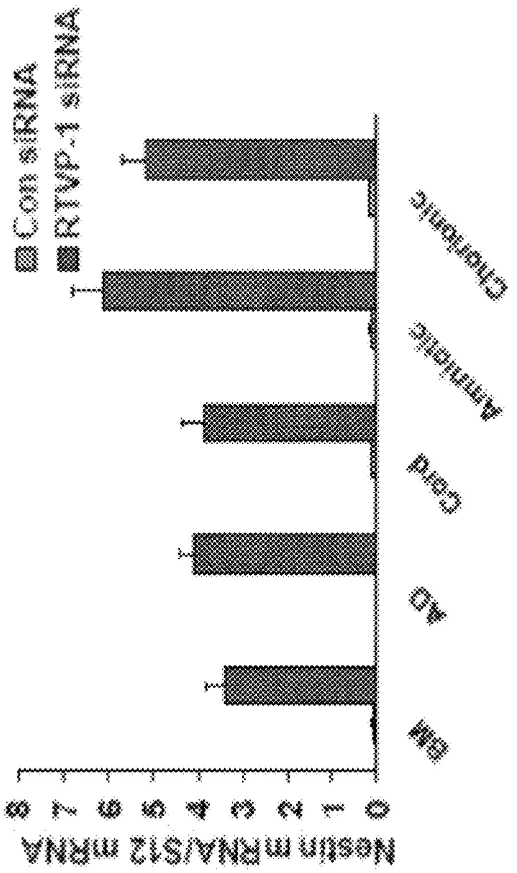
Figure 5E:
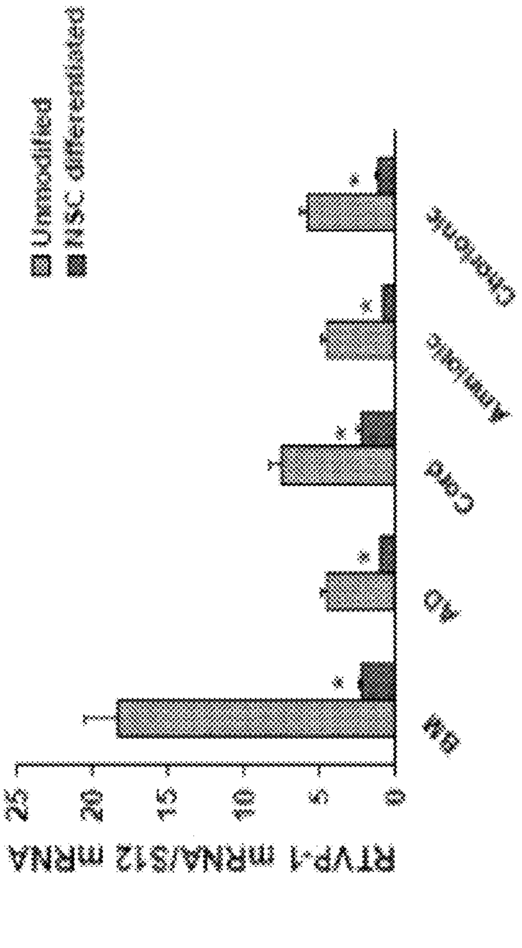

FIG. 5E is a bar graph illustrating the expression of RTVP-1 in MSCs and MSCs differentiated to NSCs.

FIG. 5F is a bar graph illustrating the effect of silencing of RTVP-1 on nestin expression in MSCs.

Figure 6A:
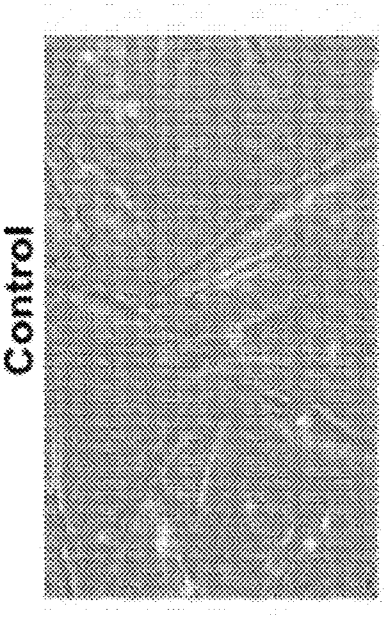
Figure 6B:
Figure 6C:
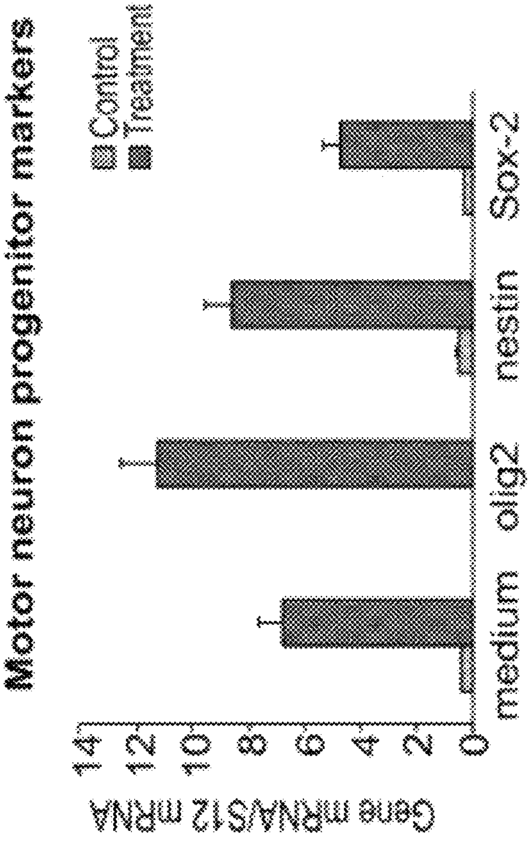
Figure 6D:
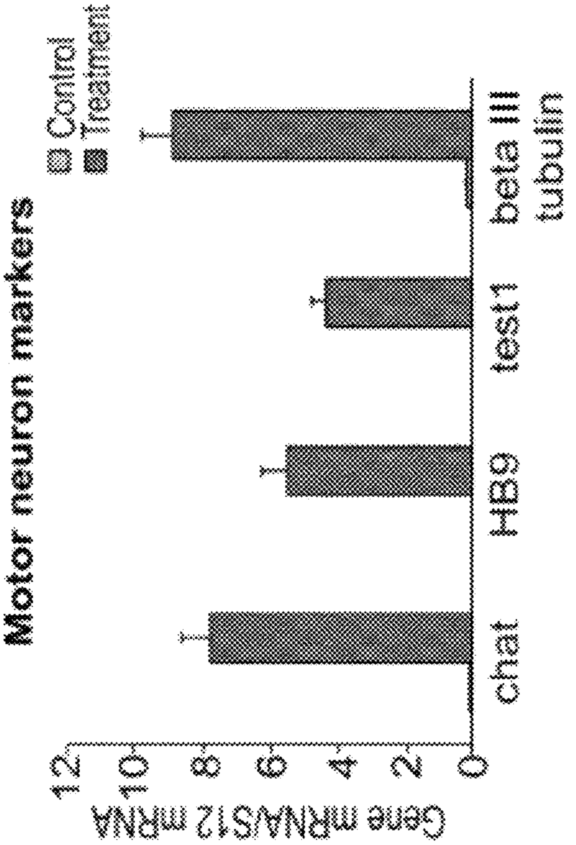

FIGS. 6A-D are photographs and graphs illustrating the effect of transfection of Olig2 and differentiation medium on placenta-derived MSCs. After 12 days in culture the cells were analyzed for the expression of motor neuron progenitor (FIG. 6C) and motor neuron markers (FIG. 6D) using real time PCR. FIG. 6A illustrates undifferentiated MSCs. FIG. 6B illustrates differentiated MSCs.

Figure 7A:
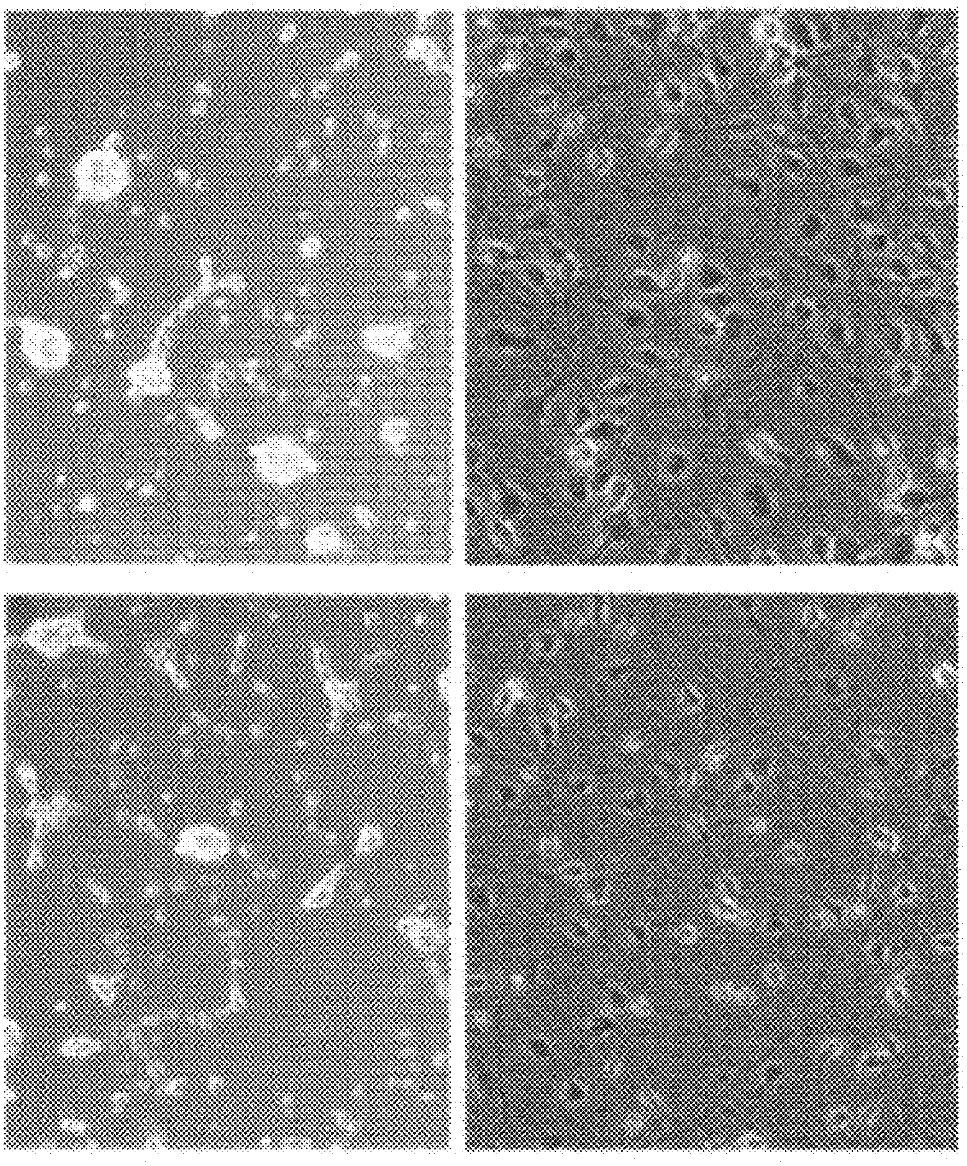
Figure 7B:
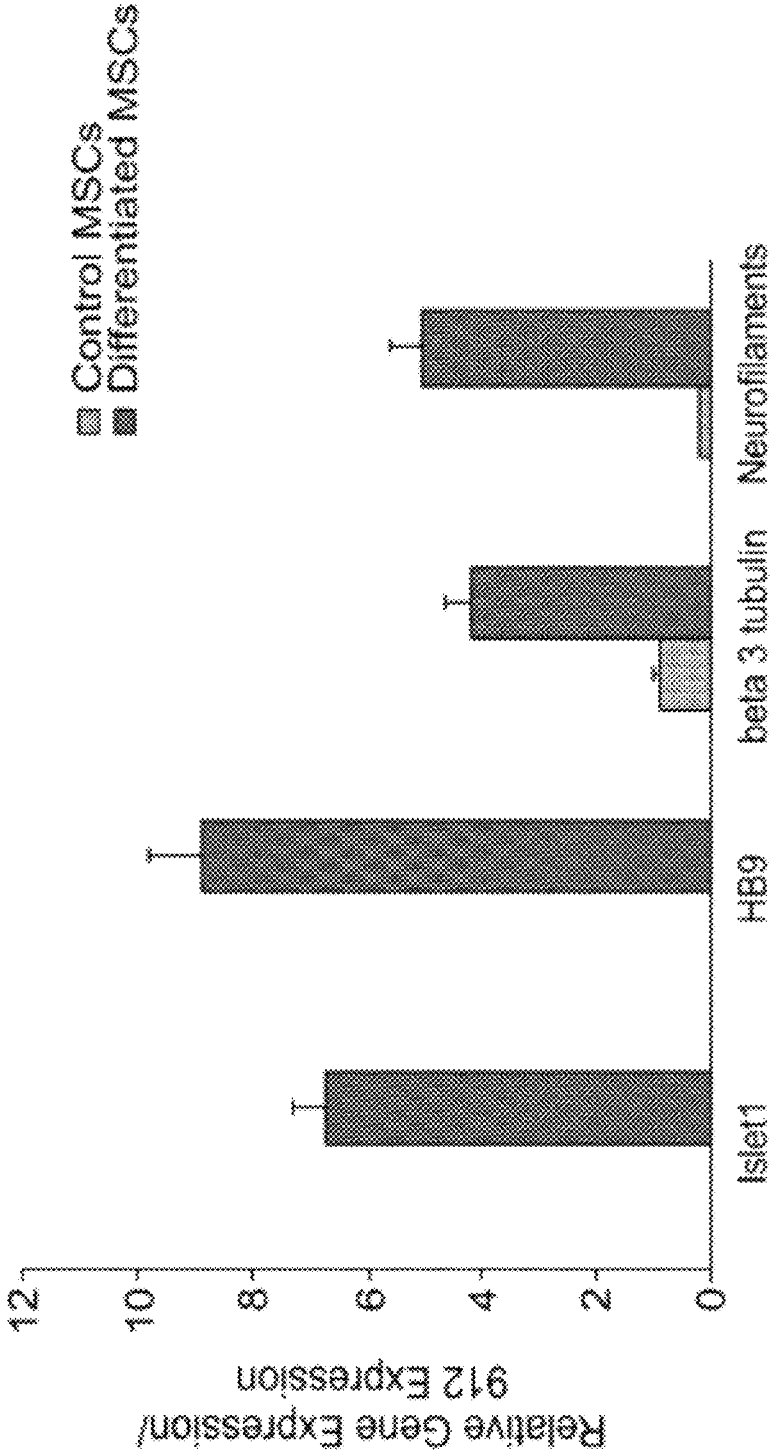

FIGS. 7A-B are graphs and photographs illustrating that NSCs may be induced to differentiate into motor neuron cells. The human neural progenitor cells (Lonza) were grown as spheroids and then plated on laminin and treated with the different factors as described in the methods. Following 12-14 days, the cells were analyzed for morphological appearance and for the different markers using real time PCR.

Figure 8:
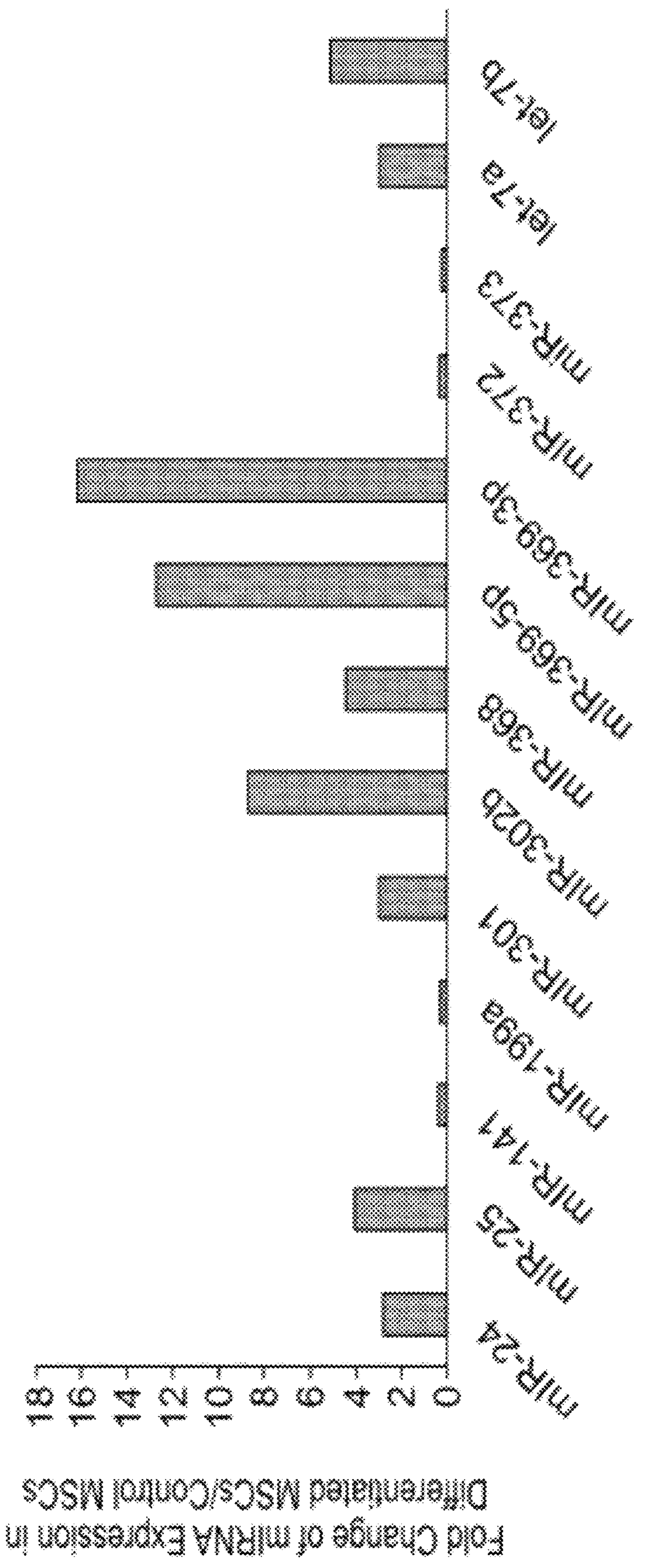

FIG. 8 is a bar graph illustrating exemplary miRNAs associated with stem cell signature and self renewal that were up-regulated during motor neuron differentiation.

Figure 9:
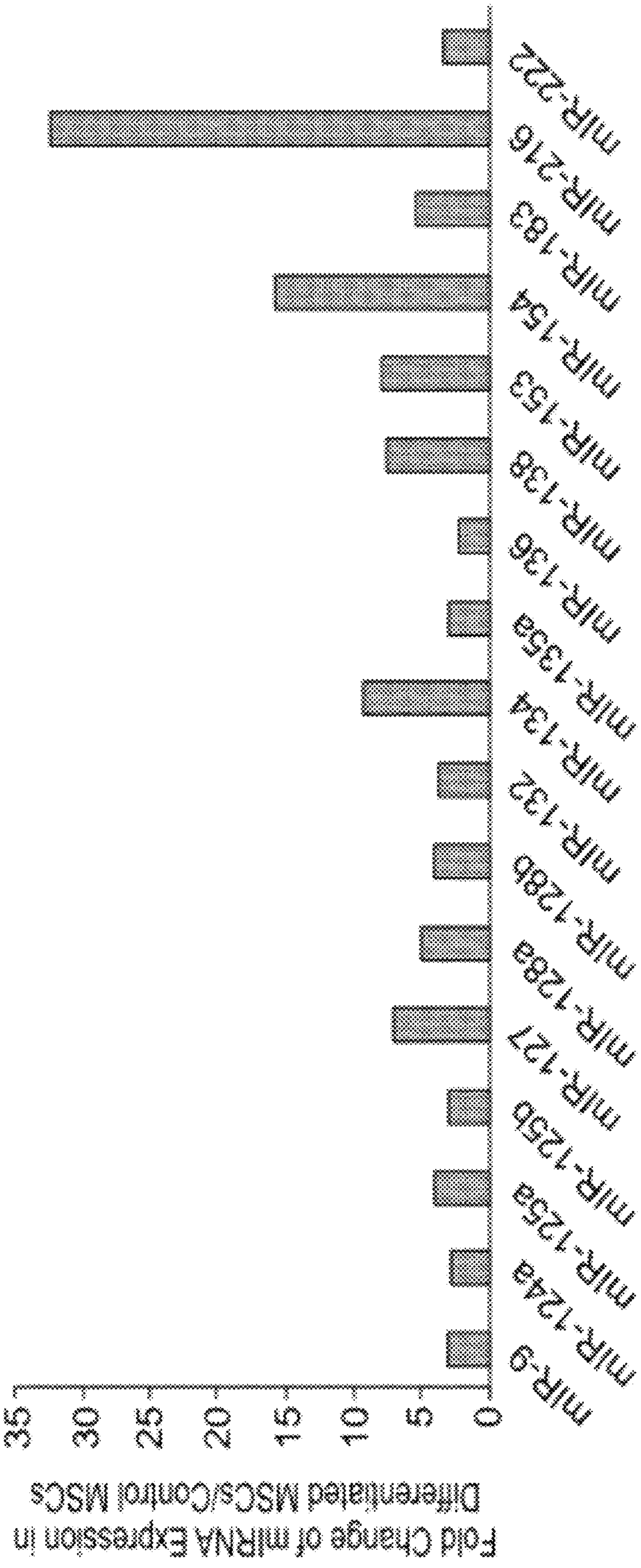

FIG. 9 is a bar graph illustrating exemplary miRNAs associated with hematopoiesis that were up-regulated during motor neuron differentiation.

Figure 10:
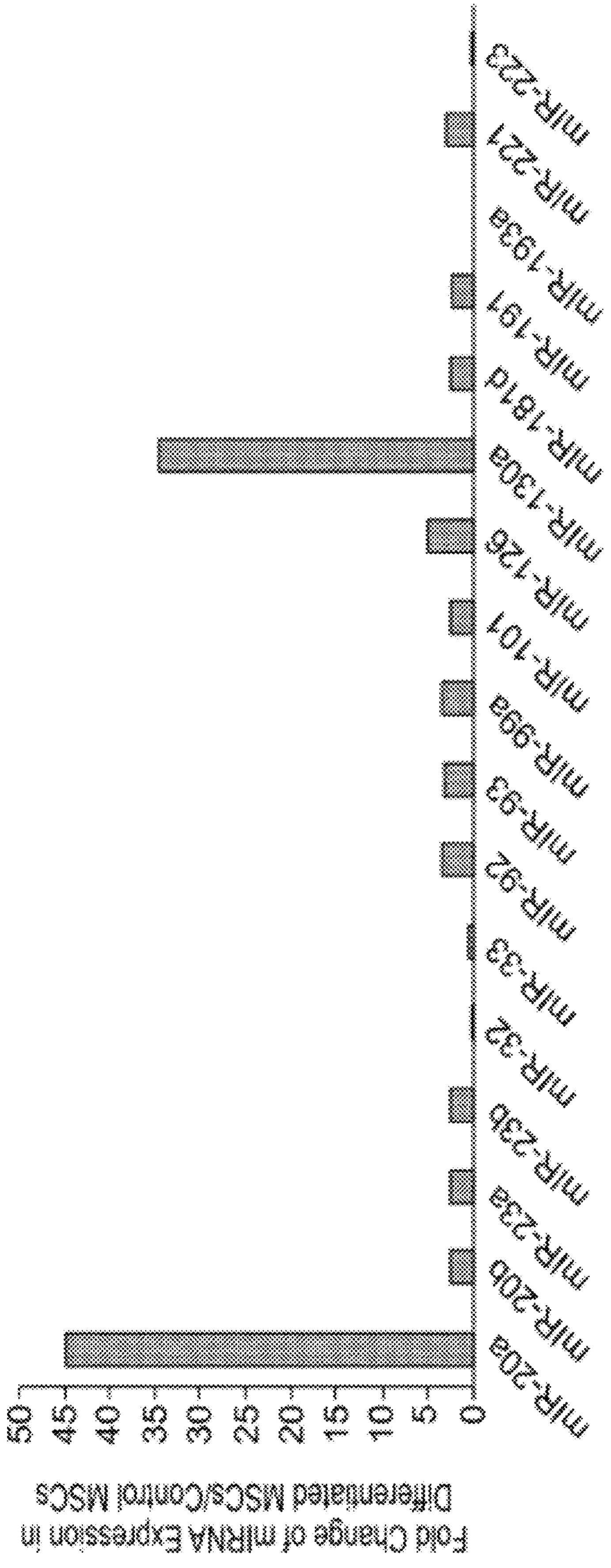

FIG. 10 is a bar graph illustrating exemplary miRNAs associated with a neuronal signature and self-renewal that were up-regulated during motor neuron differentiation.

Figure 11:
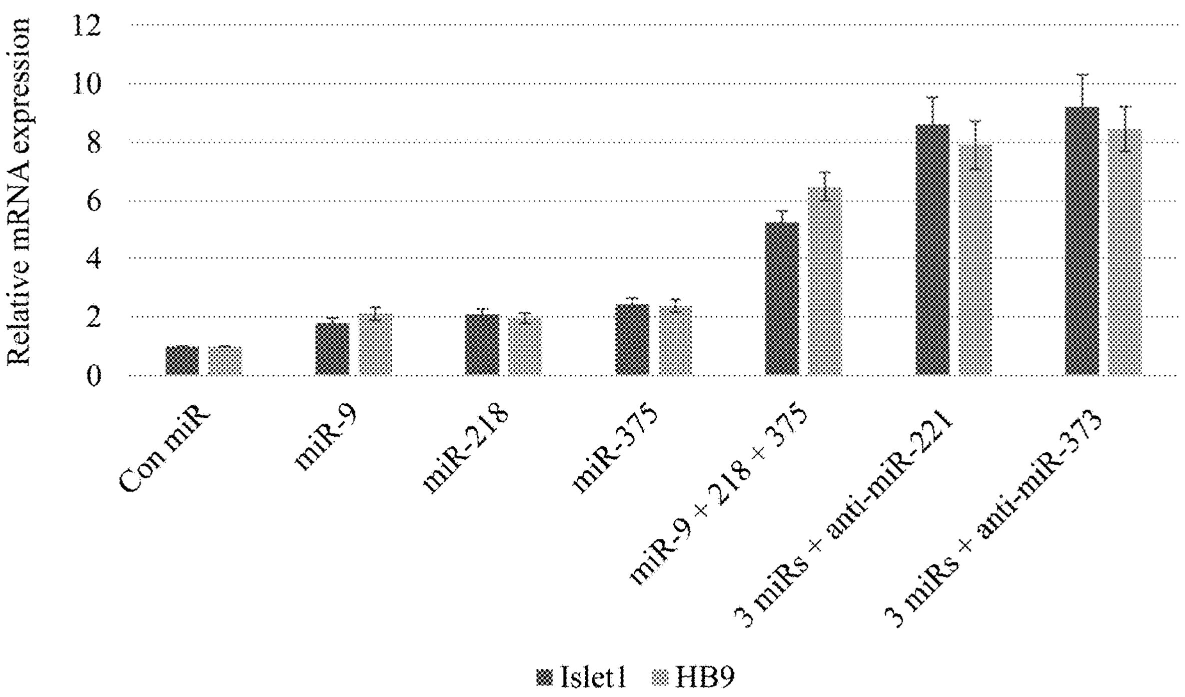

FIG. 11 is a bar graph illustrating Islet1 and HB9 mRNA expression in control MSCs and MSCs trans-differentiated toward a motor neuron cell.

Figure 12:
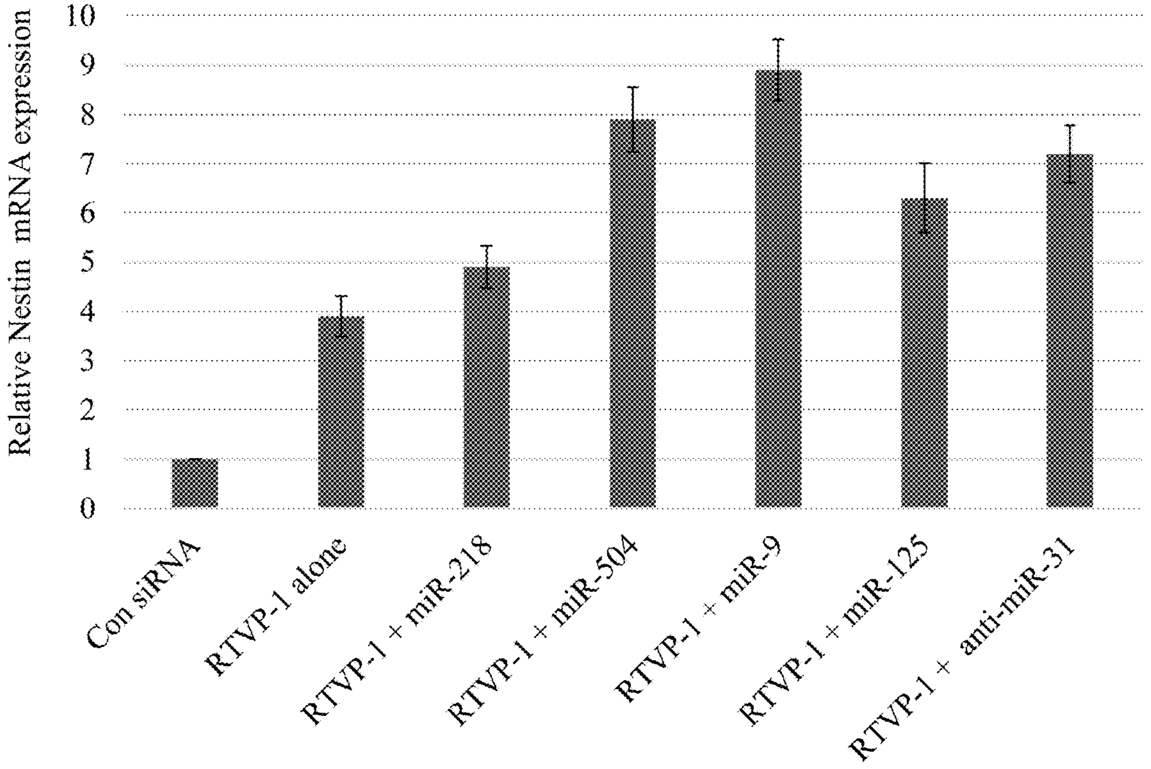

FIG. 12 is a bar graph illustrating nestin mRNA expression in control MSCs, MSCs with RTVP-1 silencing, and MSCs with RTVP-1 silencing and miR/antimiR transfection.

Figure 13:
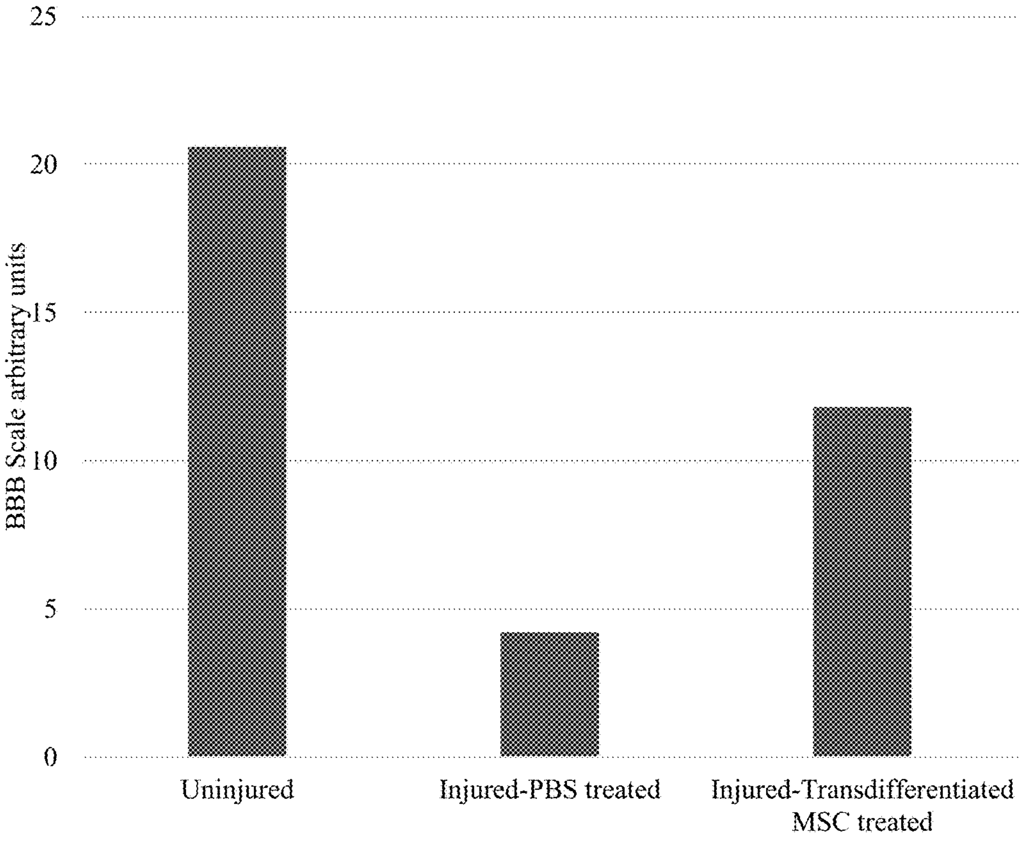

FIG. 13 is a bar graph illustrating the average score on the Basso, Beattie and Bresnahan (BBB) locomotor scale of rats with and without spinal cord injury and with injury treated with MSCs trans-differentiated toward a motor neuron cell.

DESCRIPTION OF SPECIFIC EMBODIMENTS OF THE INVENTION

The present invention, in some embodiments thereof, relates to methods of ex vivo differentiating mesenchymal stem cells towards neural progenitor cells and motor neurons using microRNAs.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Neural stem cells (NSCs) have been isolated from embryonic and fetal mammalian and human brains and propagated in vitro in a variety of culture systems (Doetsch et al., 1999, Subventricular zone astrocytes are neural stem cells in the adult mammalian brain. Cell 97:703-16, Johansson et al., 1999, Cell 96:25-34, Svendsen et al., 1998, J Neurosci Methods 85:141-52). A system for proliferating human neural stem cells (hNSCs) in serum-free culture medium containing human bFGF and human EGF also has been reported (Kim et al., 2002, Proc Natl Acad Sci USA 99: 4020-4025, Qu et al., 2001, NeuroReport 12: 1127-1132). Further, transplantation of hNSCs into experimental animals has been described (Qu et al., 2001, Id.; Qu et al., 2005, 35th Annual Meeting in Washington, D.C., November 2005).

However, challenges existed in the art of stem cell therapies using stem cells derived from embryonic/fetal tissue sources. Stem cell therapies using embryonic sources face challenges such as ethical issues, technical difficulties in cell isolation, and the need for long-term immunosuppressant administration to transplant recipients; the limitations of using fetal tissue sources have been set forth above. These challenges have hindered the applicability of hNSCs for human use.

Bone marrow (BM) contains stem cells involved not only in hematopoiesis but also for production of a variety of nonhematopoietic tissues. A subset of stromal cells in bone marrow, mesenchymal stem cells (MSCs), is capable of self-renewing and producing multiple mesenchymal cell lineages, including bone, cartilage, fat tendons, and other connective tissues (Majumdar et al., 1998, J Cell Physiol. 176:57-66, Pereira et al., 1995, Proc Natl Acad Sci USA. 92: 4857-61, Pittenger et al., 1999, Science 284: 143-7). Bone marrow mesenchymal stem cells normally are not committed to the neural lineage in differentiation. Although adult stem cells continue to possess some degrees of multipotency, cell types produced from adult stem cells are thought to be limited by their tissue-specific character. To overcome this barrier, it is necessary to alter the cell lineage of these adult stem cells.

Whilst reducing the present invention to practice, the present inventors have found that out of a vast number of potential micro RNAs (miRNAs), only particular miRNAs may be regulated in order to induce neural stem cell differentiation of mesenchymal stem cells (MSCs) and propose that such differentiated MSCs may be used to treat patients with brain diseases or disorders.

Further, the present inventors identified particular combinations of miRNAs whose regulation was found to synergistically increase the differentiation towards NSCs, as measured by nestin and SOX-2 expression.

Whilst further reducing the present invention to practice the present inventors uncovered that upon manipulation of the miRNA expression of NSCs, cells expressing motor neurons markers may be generated.

Thus, the present inventors showed that up-regulation of at least one of miR-368, miR-302b, miR-365-3p, miR-365-5p, miR-Let-7a, miR-Let-7b, miR-218, miR-134, miR-124, miR-125a, miR-9, miR-154, miR-20a, miR-130a in neural stem cells (NSCs), induced a motor neuron phenotype, whilst down-regulation of at least one of miR-372, miR-373, miR-141, miR-199a, miR-32, miR-33, miR-221 and miR-223 in NSCs also induced a motor neuron phenotype.

Further, the present inventors identified particular combinations of miRNAs whose regulation was found to synergistically increase the differentiation towards motor neurons, as measured by expression of motor neuron markers including islet1, HB9 and the neuronal markers neurofilament and tubulin.

Thus, according to one aspect of the present invention there is provided a method of predisposing mesenchymal stem cells to differentiate into neural stem cells, the method comprising up-regulating a level of at least one exogenous miRNA selected from the group consisting of miR302b, miR-371, miR-134, miR-219, miR-154, miR-155, miR-32, miR-33, miR-126, miR-127, miR-132, miR-137, miR-572, miR-935a, miR-891a, miR-1202, miR-1275, let-7c, miR-665, miR-4258, miR-361-3p, miR-374a-star, miR-892b, miR-361-5p, miR-181a, miR-16, miR-636, miR-4284, miR-1208, miR-1274b, miR-30c-2-star, miR-501-3p, hsa-miR-92a, miR-378b, miR-1287, miR-425-star, miR-324-5p, miR-3178, miR-219-1-3p, miR-197, miR-181b, miR-500-star, miR-106b, miR-502-3p, miR-30c, miR-1275, miR-422a, miR-93, miR-181d, miR-1307, miR-1301, miR-99a, miR-505-star, miR-1202, miR-12, miR-532-5p, miR-195, miR-532-3p, miR-106a, miR-17, miR-1271, miR-769-3p, miR-15b, miR-324-3p, miR-20a, miR-501-5p, miR-330-3p, miR-874, miR-500, miR-25, miR-769-5p, miR-125b-2-star, miR-130b, miR-504, miR-181a-2-star, miR-885-3p, miR-1246, miR-92b, miR-362-5p, miR-572, miR-4270, miR-378c, miR-93-star, miR-149, miR-363, miR-9, miR-18a, miR-891a, miR-346, miR-124, miR-497, miR-378, miR-1231, miR-139-5p, miR-3180-3p, miR-9-star, miR-935 and miR-20b in mesenchymal stem cells (MSCs), thereby predisposing mesenchymal stem cells to differentiate into the neural stem cells.

As used herein, the phrase "predisposing MSCs to differentiate into neural stem cells (NSCs)" refers to causing the MSCs to differentiate along the NSC lineage. The generated cells may be fully differentiated into NSCs, or partially differentiated into NSCs.

The phrase "at least one" as used in the specification refers to one, two, three four, five six, seven, eight, nine, ten or more miRNAs. Examples of particular combinations of miRNAs are provided herein below.

Mesenchymal stem cells give rise to one or more mesenchymal tissues (e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines. Although such cells can be isolated from embryonic yolk sac, placenta, umbilical cord, fetal and adolescent skin, blood and other tissues, their abundance in the easily accessible fat tissue and BM far exceeds their abundance in other tissues and as such isolation from BM and fat tissue is presently preferred.

Methods of isolating, purifying and expanding mesenchymal stem cells (MSCs) are known in the arts and include, for example, those disclosed by Caplan and Haynesworth in U.S. Pat. No. 5,486,359 and Jones E. A. et al., 2002, Isolation and characterization of bone marrow multipotential mesenchymal progenitor cells, Arthritis Rheum. 46(12): 3349-60.

Mesenchymal stem cells may be isolated from various tissues including but not limited to bone marrow, peripheral blood, blood, chorionic and amniotic placenta (e.g. fetal side of the placenta), cord blood, umbilical cord, amniotic fluid, placenta and from adipose tissue.

A method of isolating mesenchymal stem cells from peripheral blood is described by Kassis et al [Bone Marrow Transplant. 2006 May; 37(10):967-76]. A method of isolating mesenchymal stem cells from placental tissue is described by Zhang et al [Chinese Medical Journal, 2004, 117 (6):882-887]. Methods of isolating and culturing adipose tissue, placental and cord blood mesenchymal stem cells are described by Kern et al [Stem Cells, 2006; 24:1294-1301].

According to a preferred embodiment of this aspect of the present invention, the mesenchymal stem cells are human.

According to another embodiment of this aspect of the present invention, the mesenchymal stem cells are isolated from placenta and umbilical cord of newborn humans.

Bone marrow can be isolated from the iliac crest of an individual by aspiration. Low-density BM mononuclear cells (BMMNC) may be separated by a FICOL-PAQUE density gradient or by elimination of red blood cells using Hetastarch (hydroxyethyl starch). Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, a medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 μg/ml streptomycin (GIBCO); and 2 mM L-glutamine (GIBCO). Resuspended cells are plated in about 25 ml of medium in a 10 cm culture dish (Corning Glass Works, Corning, N.Y.) and incubated at 37° C. with 5% humidified C02. Following 24 hours in culture, non-adherent cells are discarded, and the adherent cells are thoroughly washed twice with phosphate buffered saline (PBS). The medium is replaced with a fresh complete medium every 3 or 4 days for about 14 days. Adherent cells are then harvested with 0.25% trypsin and 1 mM EDTA (Trypsin/EDTA, GIBCO) for 5 min at 37° C., re-plated in a 6-cm plate and cultured for another 14 days. Cells are then trypsinized and counted using a cell counting device such as for example, a hemocytometer (Hausser Scientific, Horsham, Pa.). Cultured cells are recovered by centrifugation and resuspended with 5% DMSO and 30% FCS at a concentration of 1 to 2×106 cells per ml. Aliquots of about 1 ml each are slowly frozen and stored in liquid nitrogen.

Adipose tissue-derived MSCs can be obtained by liposuction and mononuclear cells can be isolated manually by removal of the fat and fat cells, or using the Celution System (Cytori Therapeutics) following the same procedure as described above for preparation of MSCs.

According to one embodiment the populations are plated on polystyrene plastic surfaces (e.g. in a flask) and mesenchymal stem cells are isolated by removing non-adherent cells. Alternatively, mesenchymal stem cell may be isolated by FACS using mesenchymal stem cell markers.

Preferably the MSCs are at least 50% purified, more preferably at least 75% purified and even more preferably at least 90% purified.

To expand the mesenchymal stem cell fraction, frozen cells are thawed at 37° C., diluted with a complete medium and recovered by centrifugation to remove the DMSO. Cells are resuspended in a complete medium and plated at a concentration of about 5,000 cells/cm". Following 24 hours in culture, non-adherent cells are removed and the adherent cells are harvested using Trypsin/EDT A, dissociated by passage through a narrowed Pasteur pipette, and preferably re-plated at a density of about 1.5 to about 3.0 cells/cm". Under these conditions, MSC cultures can grow for about 50 population doublings and be expanded for about 2000 fold [Colter D C., et al. Rapid expansion of recycling stem cells in cultures of plastic-adherent cells from human bone marrow. Proc Natl Acad Sci USA. 97: 3213-3218, 2000].

MSC cultures utilized by some embodiments of the invention preferably include three groups of cells which are defined by their morphological features: small and agranular cells (referred to as RS-1, herein below), small and granular cells (referred to as RS-2, herein below) and large and moderately granular cells (referred to as mature MSCs, herein below). The presence and concentration of such cells in culture can be assayed by identifying a presence or absence of various cell surface markers, by using, for example, immunofluorescence, in situ hybridization, and activity assays.

When MSCs are cultured under the culturing conditions of some embodiments of the invention they exhibit negative staining for the hematopoietic stem cell markers CD34, CD11B, CD43 and CD45. A small fraction of cells (less than 10%) are dimly positive for CD31 and/or CD38 markers. In addition, mature MSCs are dimly positive for the hematopoietic stem cell marker, CD11 7 (c-Kit), moderately positive for the osteogenic MSCs marker, Stro-1 [Simmons, P. J. & Torok-Storb, B. (1991). Blood 78, and positive for the thymocytes and peripheral T lymphocytes marker, CD90 (Thy-1). On the other hand, the RS-1 cells are negative for the CD117 and Strol markers and are dimly positive for the CD90 marker, and the RS-2 cells are negative for all of these markers.

The mesenchymal stem cells of the present invention may be of autologous, syngeneic or allogeneic related (matched siblings or haploidentical family members) or unrelated fully mismatched source, as further described herein below.

Culturing of the mesenchymal stem cells can be performed in any media that supports neural stem cell differentiation (or at least does not prevent neural stem cell differentiation) such as those described in U.S. Pat. No. 6,528,245 and by Sanchez-Ramos et al. (2000); Woodburry et al. (2000); Woodburry et al. (J. Neurisci. Res. 96:908-917, 2001); Black and Woodbury (Blood Cells Mol. Dis. 27:632-635, 2001); Deng et al. (2001), Kohyama et al. (2001), Reyes and Verfatile (Ann. N.Y. Acad. Sci. 30 938:231-235, 2001) and Jiang et al. (Nature 418:47-49, 2002).

The differentiating media may be 05, neurobasal medium, DMEM or DMEM/F12, OptiMEM™ or any other medium that supports neuronal growth.

As mentioned, the mesenchymal stem cells are contacted (either ex vivo or in vivo) with at least one of the following miRNAs in order to induce differentiation into neural stem cells-miR302b, miR-371, miR-134, miR-219, miR-154, miR-155, miR-32, miR-33, miR-126, miR-127, miR-132, miR-137, miR-572, miR-935a, miR-891a, miR-1202, miR-1275, let-7c, miR-665, miR-4258, miR-361-3p, miR-374a-star, miR-892b miR-361-5p, miR-181a, miR-16, miR-636, miR-4284, miR-1208, miR-1274b, miR-30c-2-star, miR-501-3p, hsa-miR-92a, miR-378b, miR-1287, miR-425-star, miR-324-5p, miR-3178, miR-219-1-3p, miR-197, miR-181b, miR-500-star, miR-106b, miR-502-3p, miR-30c, miR-1275, miR-422a, miR-93, miR-181d, miR-1307, miR-1301, miR-99a, miR-505-star, miR-1202, miR-12, miR-532-5p, miR-195, miR-532-3p, miR-106a, miR-17, miR-1271, miR-769-3p, miR-15b, miR-324-3p, miR-20a, miR-501-5p, miR-330-3p, miR-874, miR-500, miR-25, miR-769-5p, miR-125b-2-star, miR-130b, miR-504, miR-181a-2-star, miR-885-3p, miR-1246, miR-92b, miR-362-5p, miR-572, miR-4270, miR-378c, miR-93-star, miR-149, miR-363, miR-18a, miR-891a, miR-346, miR-497, miR-378, miR-1231, miR-139-5p, miR-3180-3p, miR-935 and miR-20b.

According to a particular embodiment, the miRNA is selected from the group consisting of miR302b, miR-371, miR-134, miR-219, miR-154, miR-155, miR-32, miR-33, miR-126, miR-127, miR-132.

According to another embodiment, the miRNA is selected from the group consisting of miR-20b, miR-925, miR-891 and miR-378.

The present invention also contemplates differentiation of mesenchymal stem cells towards a neural stem cell phenotype by down-regulation of particular miRNAs—namely miR-1Ob, miR-142-3p, miR-131a, miR-125b, miR-153 and miR-181a.

The present invention contemplates down-regulation of additional miRNAs for the differentiation of MSCs towards a neural stem cell phenotype. These miRNAs include miR-409-5p, miR-193a-5p, miR-4317, miR-4288, miR-145, miR-143, miR-214, miR-199a-3p, miR-199a-5p, miR-199b-3p, miR-138, miR-31, miR-21, miR-193a-5p, miR-224-star, miR-196a, miR-487b, miR-409-5p, miR-193b-star, miR-379, miR-21-star, miR-27a-star, miR-27a, miR-4317, miR-193b, miR-27b, miR-22, 574-3p, miR-30 4288, miR-23a, miR-221-star, miR-2113, let-7i, miR-24, miR-23b, miR-299-3p, miR-518c-star, miR-221, miR-431-star, miR-523, miR-4313, miR-559, miR-614, miR-653, miR-2278, miR-768-5p, miR-154-star, miR-302a-star, miR-3199 and miR-3137.

According to a particular embodiment, the miRNA which is to be downregulated is selected from the group consisting of miR-138, miR-214, miR-199a and miR-199b.

Down-regulating such miRNAs can be affected using a polynucleotide which is hybridizable in cells under physiological conditions to the miRNA.

According to a particular embodiment, the cell population is generated by up-regulating an expression of miR-124 in mesenchymal stem cells (MSCs) whilst simultaneously down-regulating an expression of miR-let-7 in the population of MSCs.

According to a particular embodiment, the cell population is generated by down-regulating an expression of miR-891 in mesenchymal stem cells (MSCs) whilst simultaneously down-regulating an expression of miR-138 in the population of MSCs.

According to a particular embodiment, the cell population is generated by up-regulating an expression of miR-20b in mesenchymal stem cells (MSCs) whilst simultaneously down-regulating an expression of miR-138 in the population of MSCs.

According to a particular embodiment, the cell population is generated by up-regulating an expression of miR-378 in mesenchymal stem cells (MSCs) whilst simultaneously down-regulating an expression of miR-138 in the population of MSCs.

As used herein, the term "hybridizable" refers to capable of hybridizing, i.e., forming a double strand molecule such as RNA:RNA, RNA:DNA and/or DNA:DNA molecules. "Physiological conditions" refer to the conditions present in cells, tissue or a whole organism or body. Preferably, the physiological conditions used by the present invention include a temperature between 34-40° C., more preferably, a temperature between 35-38° C., more preferably, a temperature between 36 and 37.5° C., most preferably, a temperature between 37 to 37.5° C.; salt concentrations (e.g., sodium chloride NaCl) between 0.8-1%, more preferably, about 0.9%; and/or pH values in the range of 6.5-8, more preferably, 6.5-7.5, most preferably, pH of 7-7.5.

As mentioned, the present inventors have also uncovered that upon manipulation of particular miRNAs in neural stem cells, cells expressing motor neurons markers may be generated.

Thus, according to another aspect of the present invention there is provided a method of predisposing neural stem cells to differentiate into motor neurons comprising up-regulating a level of at least one exogenous miRNA selected from the group consisting of miR-368, miR-302b, miR-365-3p, miR-365-5p, miR-Let-7a, miR-Let-7b, miR-218, miR-134, miR-124, miR-125a, miR-9, miR-154, miR-20a, miR-130a in neural stem cells (NSCs).

The neural stem cells of this aspect of the present invention may be non-committed neural stem cells that are not committed to any particular type of neural cell such as but not limited to neuronal and glial cell types. Preferably these cells have a potential to commit to a neural fate. Alternatively, the neural stem cells may be committed to a particular neural cell type, such as a motor neuron, but do not express/secrete markers of terminal differentiation e.g. do not secrete neurotransmitters.

According to a particular embodiment, the neural stem cells express at least one of nestin and/or SOX-2. Additional markers include SOX1, SOX3, PSA-NCAM and MUSASHI-1.

Methods of confirming expression of the markers are provided herein below. Formation of "neural rosettes" is another morphologic marker of neural stem cell formation.

According to one embodiment, the neural stem cells have been generated by ex vivo differentiation of mesenchymal stem cells or embryonic stem cells (or induced embryonic stem cells).

Mesenchymal stem cells have been described herein above. Numerous methods are known in the art for differentiating MSCs towards a neural stem cell fate including genetic modification and/or culturing in a medium which promotes differentiation towards that fate. The medium typically comprises growth factors and/or cytokines including, but not limited to epidermal growth factor (EGF), basic fibroblast growth factor (bFGF). Typically, the differentiation is affected in serum free medium, or serum replacements.

According to a particular embodiment, NSCs are generated by genetically modifying the MSCs to express an exogenous miRNA, as described herein above.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see W02006/040763) and embryonic germ (EG) cells which are obtained from the genital tissue of a fetus any time during gestation, preferably before 10 weeks of gestation.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-program the cell to acquire embryonic stem cells characteristics. According to some embodiments of the invention, the induced pluripotent stem cells are formed by inducing the expression of Oct-4, Sox2, Kfl4 and c-Myc in a somatic stem cell.

The embryonic stem cells of some embodiments of the invention can be obtained using well-known cell-culture methods. For example, human embryonic stem cells can be isolated from human blastocysts. Human blastocysts are typically obtained from human in vivo pre-implantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 30 1989]; and Gardner et al., [Fertil. Steril. 69: 84, 1998].

It will be appreciated that commercially available stem cells can also be used with this aspect of some embodiments of the invention. Human ES cells can be purchased from the NIH human embryonic stem cells registry (www.escr.nih-.gov). Non-limiting examples of commercially available embryonic stem cell lines are BGO1, BG02, BG03, BG04, CY12, CY30, CY92, CY1O, TE03 and TE32.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 February 14. (Epub ahead of print); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

Methods of generating neural stem cells from ESCs or iPS cells are known in the art and include for example those which induce differentiation via embryoid bodies and those which induce differentiation via adherent culture. Particular protocols for differentiating ESCs towards a neuronal fate are reviewed in Dhara et al., Journal of Cellular Biochemistry 105:633-640 (2008), the contents of which are incorporated herein by reference. It will be appreciated that many other methods are known for differentiating ESC, iPSCs and MSCs towards neuronal stem cells and the present application contemplates use of all these methods.

The neuronal stem cells of the present invention may be of autologous, syngeneic or allogeneic related (matched siblings or haploidentical family members) or unrelated fully mismatched source.

Culturing of neuronal stem cells can be performed in any media that supports neural stem cell differentiation, examples of which are described herein above.

As mentioned, the neuronal stem cells are contacted (either ex vivo or in vivo) with at least one of the following miRNAs in order to induce differentiation towards the motor neuron lineage—miR-368, miR-302b, miR-365-3p, miR-365-5p, miR-Let-7a miR-Let-7b, miR-218, miR-134, miR-124, miR-125a, miR-9, miR-154, miR-20a and miR-130a.

The present invention also contemplates differentiation of neuronal stem cells towards motor neuron phenotype by down-regulation of particular miRNAs—namely miR-372, miR-373, miR-141, miR-199a, miR-32, miR-33, miR-221 and miR-223.

Down-regulating such miRNAs can be affected using a polynucleotide which is hybridizable in cells under physiological conditions to the miRNA molecule.

According to a particular embodiment, the cell population is generated by up-regulating an expression of each of miR Let-7a, miR-124, miR-368 and miR-154 in the neural stem cells.

According to a particular embodiment, the cell population is generated by up-regulating an expression of each of miR-125a, miR-9 and miR-130a in the neural stem cells.

According to still another embodiment, the cell population is generated by up-regulating an expression of each of each of miR-218, miR-134 and miR-20a.

The present inventors further contemplate down-regulating each of miR-141, miR-32, miR-33, miR-221, miR-223 and miR-373 in addition to any of the methods described herein above to enhance the differentiation towards the motor neuron phenotype.

Mesenchymal stem cells were differentiated into motor neurons by overexpressing Olig2 and HB9. The present inventors performed a miRNA array analysis on the differentiated and non-differentiated cells and found a number of miRNAs that were overexpressed in a statistically significant manner (more than 3 fold) and a number of miRNAs that were downregulated in a statistically significant manner (more than 3 fold). The present inventors contemplate that the miRNAs whose expression was increased in the differentiated cells may be candidates for overexpression in order to generate motor neurons from MSCs. The present inventors contemplate that the miRNAs whose expression was decreased in the differentiated cells are candidates for down-regulation in order to generate motor neurons from MSCs.

Thus, according to still another aspect of the present invention there is provided a method of predisposing MSCs to differentiate into motor neurons, the method comprising up-regulating a level of at least one exogenous miRNA selected from the group consisting of miR-368, miR-365, miR-500, miR-648, miR-491, miR-218, miR-155, miR-192, let-7b, miR-16, miR-210, miR-197, miR-21, miR-373, miR-27a, miR-122, miR-17, miR-494, miR-449, miR-503, miR-30a, miR-196a, miR-122, miR-7, miR-151-5p, miR-16, miR-22, miR-31, miR-424, miR-1, miR-29c, miR-942, miR-100, miR-520, miR-663a, miR-562, miR-449a, miR-449b-5p, miR-520b, miR-451, miR-532-59, miR-605, miR-504, miR-503, miR-155, miR-34a, miR-16, miR-7b, miR-103, miR-124, miR-1385p, miR-16, miR-330, miR-520, miR-608, miR-708, miR-107, miR-137, miR-132, miR-145, miR-204, miR-125b, miR-224, miR-30a, miR-375, miR-101, miR-106b, miR-128, miR-129-5p, miR-153, miR-203, miR-214, miR-338-3p, miR-346, miR-98, miR-107, miR-141, miR-217, miR-424, miR-449, miR-7, miR-9, miR-93, miR-99a, miR-100, miR-1228, miR-183, miR-185, miR-190, miR-522, miR-650, miR-675, miR-342-3p, miR-31 in the mesenchymal stem cells (MSCs).

According to yet another aspect of the present invention there is provided a method of predisposing MSCs to differentiate into motor neurons, the method comprising down-regulating an expression of at least one miRNA selected from the group consisting of miR-199a, miR-372, miR-373, miR-942, miR-2113, miR-301a-3p, miR-302c, miR-30b-5p, miR-30c, miR-326, miR-328, miR-331-3p, miR-340, miR-345, miR-361-5p, miR-363, miR-365a-3p, miR-371a-3p, miR-3'73-3p, miR-374a, miR-423-3p, miR-449b-5p, miR-451a, miR-494, miR-504, miR-515-3p, miR-516a-3p, miR-519e, miR-520a-3p, miR-520c-3p, miR-520g, miR-532-5p, miR-559, miR-562, miR-572, miR-590-5p, miR-605, miR-608, miR-626, miR-639, miR-654-3p, miR-657, miR-661, miR-708-5p, miR-942, miR-96, miR-99arno and miR-194 by up-regulating a level of at least one polynucleotide agent that hybridizes and inhibits a function of said at least one miRNA in the MSCs thereby predisposing MSCs to differentiate into the motor neurons.

The term "microRNA", "miRNA", and "miR" are synonymous and refer to a collection of non-coding single-stranded RNA molecules of about 19-28 nucleotides in length, which regulate gene expression. miRNAs are found in a wide range of organisms and have been shown to play a role in development, homeostasis, and disease etiology.

Below is a brief description of the mechanism of miRNA activity.

Genes coding for miRNAs are transcribed leading to production of a miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nt precursor known as the pre-miRNA. Drosha cleaves the pri-miRNA with a staggered cut typical of RNase III endonucleases yielding a pre-miRNA stem loop with a 5' phosphate and −2 nucleotide 3' overhang. It is estimated that approximately one helical turn of stem (−10 nucleotides) extending beyond the Drosha cleavage site is essential for efficient processing. The pre-miRNA is then actively transported from the nucleus to the cytoplasm by Ran-OTP and the export receptor exportin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and −2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRN A/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to down-regulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-0,4'-C-ethylene-bridged nucleic acids (ENA)). Other modifications are described herein below. For mature, double stranded miRNA mimics, the length of the duplex region can vary between 13-33, 18-20 24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise any of the sequences described herein, or variants thereof.

It will be appreciated from the description provided herein above, that contacting mesenchymal stem cells may be affected in a number of ways:

1. Transiently transfecting the mesenchymal stem cells with the mature miRNA (or modified form thereof, as described herein below). The miRNAs designed according to the teachings of the present invention can be generated according to any oligonucleotide synthesis method known in the art, including both enzymatic syntheses and solid-phase syntheses. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. 5 (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

2. Stably, or transiently transfecting the mesenchymal stem cells with an expression vector which encodes the mature miRNA or with miRNA mimic.

3. Stably, or transiently transfecting the mesenchymal stem cells with an expression vector which encodes the pre-miRNA. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of the miRNA, or variants thereof.

4. Stably, or transiently transfecting the mesenchymal stem cells with an expression vector which encodes the pri-miRNA. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. Preparation of miRNAs mimics can be affected by chemical synthesis methods or by recombinant methods.

miRNA antagonists may be introduced into cells using transfection protocols known in the art using either siRNAs or expression vectors such as Anatgomirs.

As mentioned herein above, the polynucleotides which down-regulate the miRNAs described herein above may be provided as modified polynucleotides using various methods known in the art.

For example, the oligonucleotides (e.g. miRNAs) or polynucleotides of the present invention may comprise heterocylic nucleosides consisting of purines and the pyrimidines bases, bonded in a 3'-to-5' phosphodiester linkage.

Preferably used oligonucleotides or polynucleotides are those modified either in backbone, internucleoside linkages, or bases, as is broadly described herein under.

Specific examples of preferred oligonucleotides or polynucleotides useful according to this aspect of the present invention include oligonucleotides or polynucleotides containing modified backbones or non-natural internucleoside linkages. Oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide or polynucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide or polynucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and CH2 component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677, 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides or polynucleotides which may be used according to the present invention are those modified in both sugar and the intemucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Oligonucleotides or polynucleotides of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990),"The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and 0-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-0-methoxyethyl sugar modifications.

To express miRNAs or polynucleotide agents which regulate miRNAs in mesencyhymal stem cells or neural stem cells, a polynucleotide sequence encoding the miRNA (or pre-miRNA, or pri-miRNA, or polynucleotide which downregulates the miRNAs) is preferably ligated into a nucleic acid construct suitable for mesenchymal stem cell (or neural stem cell) expression. Such a nucleic acid construct includes a promoter sequence for directing transcription of the polynucleotide sequence in the cell in a constitutive or inducible manner.

It will be appreciated that the nucleic acid construct of some embodiments of the invention can also utilize miRNA homologues which exhibit the desired activity (e.g. motor neuron or neural stem cell differentiating ability). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any of the sequences described herein above, as determined using the BestFit software of the Wisconsin sequence analysis package, utilizing the Smith and Waterman algorithm, where gap weight equals 50, length weight equals 3, average match equals 10 and average mismatch equals −9.

In addition, the homologues can be, for example, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the sequences described herein above, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example tetracycline-inducible promoter (Zabala M, et al., Cancer Res. 2004, 64(8): 2799-804).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed—i.e. mesenchymal stem cells or neural stem cells.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives. Other expression vectors are available from SBI or Sigma.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A+, pMTO1O/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-1) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

According to one embodiment, a lentiviral vector is used to transfect the mesenchymal stem cells or neural stem cells.

Various methods can be used to introduce the expression vector of some embodiments of the invention into mesenchymal stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Other vectors can be used that are non-viral, such as cationic lipids, polylysine, and dendrimers.

The miRNAs, miRNA mimics and pre-miRs can be transfected into cells also using nanoparticles such as gold nanoparticles and by ferric oxide magnetic NP—see for example Ghosh et al., Biomaterials. 2013 January; 34(3): 807-16; Crew E, et al., Anal Chem. 2012 Jan. 3; 84(1):26-9.

Other modes of transfection that do not involved integration include the use of minicircle DNA vectors or the use of PiggyBac transposon that allows the transfection of genes that can be later removed from the genome.

As mentioned hereinabove, a variety of prokaryotic or eukaryotic cells can be used as host-expression systems to express the miRNAs or polynucleotide agent capable of down-regulating the miRNA of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the miRNAs of some embodiments of the invention.

Examples of bacterial constructs include the pET series of *E. coli* expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

The conditions used for contacting the mesenchymal stem cells or neural stem cells are selected for a time period/concentration of cells/concentration of miRNA/ratio between cells and miRNA which enable the miRNA (or inhibitors thereof) to induce differentiation thereof. The present invention further contemplates incubation of the stem cells with a differentiation factor which promotes differentiation towards a motor neuron or neural stem cell lineage. The incubation with such differentiation factors may be affected prior to, concomitant with or following the contacting with the miRNA. Examples of such agents are provided in the Examples section herein below.

Alternatively, or additionally, the mesenchymal stem cells may be genetically modified so as to express such differentiation factors, using expression constructs such as those described herein above. Further, the mesenchymal stem cell can be genetically modified using the CRISPR/Cas9 system, or an equivalent system, to no long express a target which is being silenced/down-regulated, such as for example RTVP-1.

During or following the differentiation step the stem cells may be monitored for their differentiation state. Cell differentiation can be determined upon examination of cell or tissue-specific markers which are known to be indicative of differentiation.

For example, the neural stem cells may express at least one of nestin and SOX-2. Additional markers include SOX1, SOX3, PSA-NCAM and MUSASHI-1.

Below is a list of markers that may be used to confirm differentiation into motor neurons: ChAT (choline acetyltransferase), Chox1O, Enl, Even-skipped (Eve) transcription factor, Evx1/2, Fibroblast growth factor-1 (FGF1 or acidic FGF), HB9, Isl1 (lslet-1), Isl2, Islet1/2, Lim3, p75(NTR) (p75 neurotrophin receptor), REG2, Sim1, SMI32 (SMI-32) and Zfh1.

Tissue/cell specific markers can be detected using immunological techniques well known in the art [Thomson J A et al., (1998). Science 282: 1145-7]. Examples include, but are not limited to, flow cytometry for membrane-bound markers, immunohistochemistry for extracellular and intracellular markers and enzymatic immunoassay, for secreted molecular markers.

It will be appreciated that the cells obtained according to the methods described herein may be enriched for a particular cell type—e.g. progenitor cell type or mature cell type. Thus for example, the time of differentiation may be selected to obtain an earlier progenitor type (e.g. one that expresses at least one of the following markers nestin, olig2 and Sox2) or a later mature cell type (e.g. one that expresses at least one of the following markers ChAT, islet1, HB9 and J33 tubulin).

Further enrichment of a particular cell type may be affected using cell sorting techniques such as FACS and magnetic sorting.

In addition, cell differentiation can be also followed by specific reporters that are tagged with GFP or RFP and exhibit increased fluorescence upon differentiation.

By determining the targets of the miRNAs of the present invention that are proposed for up-regulation, it will be appreciated that the scope of the present invention may be broadened to include down-regulation of the targets by means other than contacting with miRNA. Correspondingly, by determining the targets of the miRNAs of the present invention that are proposed for down-regulation, it will be appreciated that the scope of the present invention may be broadened to include up-regulation of the targets.

For example, the present inventors have shown that one of the targets of miR-137 is Related to testis-specific, vespid and pathogenesis protein 1 (RTVP-1) Thus the present invention contemplates that differentiation towards the neural stem cell lineage may be affected by down-regulation of this protein.

Thus, according to another aspect of the invention, there is provided a method of generating neural stem cells, the method comprising contacting mesenchymal stem cells (MSCs) with an agent that down-regulates an amount and/or activity of Related to testis-specific, vespid and pathogenesis protein 1 (RTVP-1), thereby generating the neural stem cells.

Related to testis-specific, vespid and pathogenesis protein 1 (RTVP-1) was cloned from human GBM cell lines by two groups and was termed glioma pathogenesis-related protein-GLIPR1 or RTVP-1 [Rich T, et al., Gene 1996; 180: 125-30], incorporated herein by reference. RTVP-1 contains a putative signal peptide, a trans membrane domain and a SCP domain, with a yet unknown function which is also found in other RTVP-1 homologs including TPX-1, the venom allergen antigen 5 and group 1 of the plant pathogenesis-related proteins (PR-1).

Down-regulation of RTVP-1 (or any of the other miRNA targets of the present invention) can be obtained at the genomic and/or the transcript level using a variety of molecules which interfere with transcription and/or translation (e.g., RNA silencing agents, Ribozyme, DNAzyme and antisense), or on the protein level using e.g., antagonists, enzymes that cleave the polypeptide and the like.

Following is a list of agents capable of down-regulating expression level and/or activity of RTVP-1.

One example of an agent capable of down-regulating RTVP-1 is an antibody or antibody fragment capable of specifically binding thereto. Preferably, the antibody is capable of being internalized by the cell and entering the nucleus.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Down-regulation of RTVP-1 can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include non-coding RNA molecules, for example RNA duplexes comprising paired strands, as well as precursor RNAs from which such small non-coding RNAs can be generated. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to down-regulate protein expression from the mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi: 10.1089/154545703322617069.

The present invention also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate dsRNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3; (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA, as further described herein above.

Synthesis of RNA silencing agents suitable for use with the present invention can be affected as follows. First, the miRNA target mRNA sequence (e.g. CTGF sequence) is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

The RNA silencing agents of the present invention may comprise nucleic acid analogs that may have at least one different linkage, e.g., phosphoramidate, phosphorothioate, phosphorodithioate, or 0-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; 0- and N-alkylated nucleotides, e.g. N6-methyl adenosine are suitable. The 2'-0H-group may be replaced by a group selected from H, OR, R, halo, SH, SR, NH2, NHR, NR2 or CN, wherein R is C1-C6 alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432: 173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, plsl, TAT(48-60), pVEC, MTS, and MAP.

Another agent capable of down-regulating RTVP-1 is a DNAzyme molecule capable of specifically cleaving an mRNA transcript or DNA sequence of CTGF. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 20 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al.

Down-regulation of RTVP-1 can also be obtained by using an antisense polynucleotide capable of specifically hybridizing with an mRNA transcript encoding RTVP-1.

Design of antisense molecules which can be used to efficiently down-regulate RTVP-1 should take into consideration two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp 130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Another agent capable of down-regulating RTVP-1 is a ribozyme molecule capable of specifically cleaving an mRNA transcript encoding RTVP-1. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications.

An additional method of regulating the expression of a RTVP-1 gene in cells is via triplex forming oligonuclotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408.

Modification of the oligonuclotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| | | | | |
|---|---|---|---|---|
| oligo | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific down-regulation of gene expression. Examples of such suppression of gene expression in cells treated with TFOs include knockout of episomal supFG 1 and endogenous HPRT genes in mammalian cells (Vasquez et al., Nucl Acids Res. 1999; 27:1176-81, and Puri, et al, J Biol Chem, 2001; 276:28991-98), and the sequence- and target specific down-regulation of expression of the Ets2 transcription factor, important in prostate cancer etiology (Carbone, et al, Nucl Acid Res. 2003; 31:833-43) and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both down-regulation and up-regulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

The invention also contemplates silencing RTVP-1 by genetic modification of the RTVP-1 locus. This modification can include complete deletion of part or all of the coding region such that no functional protein is produced. Modification can also include mutation or deletion of the part or all of the promotor, such that the coding region is not transcribed. In some embodiments, silencing of RTVP-1 comprises introduction of CRISPR/Cas9 reagents to genetically delete and/or modify the RTVP-1 genomic locus.

The conditions used for contacting the mesenchymal stem cells are selected for a time period/concentration of cells/concentration of RTVP-1 down-regulatory agent/ratio between cells and RTVP-1 down-regulatory agent which enable the RTVP-1 down-regulatory agent to induce differentiation thereof.

Isolated cell populations obtained according to the methods describe herein are typically non-homogeneous, although homogeneous cell populations are also contemplated.

According to a particular embodiment, the cell populations are genetically modified to express an exogenous miRNA or a polynucleotide agent capable of down-regulating the miRNA.

The term “isolated” as used herein refers to a population of cells that has been removed from its in-vivo location (e.g. bone marrow, neural tissue). Preferably the isolated cell population is substantially free from other substances (e.g., other cells) that are present in its in-vivo location.

Cell populations may be selected such that more than about 50% (alternatively more than about 60%, more than about 70%, more than about 80%, more than about 90% or even more than about 95%) of the cells express at least one, at least two, at least three, at least four, at least five of the markers for motor neurons or at least one, at least two, at least three, at least four, at least five of the markers for neural stem cells.

Isolation of particular subpopulations of cells may be affected using techniques known in the art including fluorescent activated cell sorting and/or magnetic separation of cells.

The cells of the populations of this aspect of the present invention may comprise structural motor neuron or neural stem cell phenotypes including a cell size, a cell shape, an organelle size and an organelle number. These structural phenotypes may be analyzed using microscopic techniques (e.g. scanning electro microscopy). Antibodies or dyes may be used to highlight distinguishing features in order to aid in the analysis.

The cells and cell populations of the present invention may be useful for a variety of therapeutic purposes. Representative examples of CNS diseases or disorders that can be beneficially treated with the cells described herein include, but are not limited to, a pain disorder, a motion disorder, a dissociative disorder, a mood disorder, an affective disorder, a neurodegenerative disease or disorder, psychiatric disorders and a convulsive disorder.

More specific examples of such conditions include, but are not limited to, Parkinson's, ALS, Multiple Sclerosis, Huntingdon's disease, autoimmune encephalomyelitis, spinal cord injury, cerebral palsy, diabetic neuropathy, glaucatomus neuropathy, macular degeneration, action tremors and tardive dyskinesia, panic, anxiety, depression, alcoholism, insomnia, manic behavior, schizophrenia, autism-spectrum disorder, manic-depressive disorders, Alzheimer's and epilepsy.

The use of differentiated MSCs may be also indicated for treatment of traumatic lesions of the nervous system including spinal cord injury and also for treatment of stroke caused by bleeding or thrombosis or embolism because of the need to induce neurogenesis and provide survival factors to minimize insult to damaged neurons.

The motor neuron like cells of the present invention may be useful for motor neuron diseases including, but not limited to amyotrophic lateral sclerosis (ALS), primary lateral sclerosis (PLS), pseudobulbar palsy and progressive bulbar palsy.

In any of the methods described herein the cells may be obtained from an autologous, semi-allogeneic or non-autologous (i.e., allogeneic or xenogeneic) human donor or embryo or cord/placenta. For example, cells may be isolated from a human cadaver or a donor subject.

The term semi-allogeneic refers to donor cells which are partially-mismatched to recipient cells at a major histocompatibility complex (MHC) class I or class II locus.

The cells of the present invention can be administered to the treated individual using a variety of transplantation approaches, the nature of which depends on the site of implantation.

The term or phrase "transplantation", "cell replacement" or "grafting" are used interchangeably herein and refer to the introduction of the cells of the present invention to target tissue. As mentioned, the cells can be derived from the recipient or from an allogeneic, semi-allogeneic or xenogeneic donor.

The cells can be injected systemically into the circulation, administered intrathecally or grafted into the central nervous system, the spinal cord or into the ventricular cavities or subdurally onto the surface of a host brain. Conditions for successful transplantation include: (i) viability of the implant; (ii) retention of the graft at the site of transplantation; and (iii) minimum amount of pathological reaction at the site of transplantation. Methods for transplanting various nerve tissues, for example embryonic brain tissue, into host brains have been described in: "Neural grafting in the mammalian CNS", Bjorklund and Stenevi, eds. (1985); Freed et al., 2001; Olanow et al., 2003). These procedures include intraparenchymal transplantation, i.e. within the host brain (as compared to outside the brain or extraparenchymal transplantation) achieved by injection or deposition of tissue within the brain parenchyma at the time of transplantation.

Intraparenchymal transplantation can be performed using two approaches: (i) injection of cells into the host brain parenchyma or (ii) preparing a cavity by surgical means to expose the host brain parenchyma and then depositing the graft into the cavity.

Both methods provide parenchymal deposition between the graft and host brain tissue at the time of grafting, and both facilitate anatomical integration between the graft and host brain tissue. This is of importance if it is required that the graft becomes an integral part of the host brain and survives for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord. The cells may also be introduced into the putamen, nucleus basalis, hippocampus cortex, striatum, substantia nigra or caudate regions of the brain, as well as the spinal cord.

The cells may also be transplanted to a healthy region of the tissue. In some cases the exact location of the damaged tissue area may be unknown and the cells may be inadvertently transplanted to a healthy region. In other cases, it may be preferable to administer the cells to a healthy region, thereby avoiding any further damage to that region. Whatever the case, following transplantation, the cells preferably migrate to the damaged area.

For transplanting, the cell suspension is drawn up into the syringe and administered to anesthetized transplantation recipients. Multiple injections may be made using this procedure.

The cellular suspension procedure thus permits grafting of the cells to any predetermined site in the brain or spinal cord, is relatively non-traumatic, allows multiple grafting simultaneously in several different sites or the same site using the same cell suspension, and permits mixtures of cells from different anatomical regions.

Multiple grafts may consist of a mixture of cell types, and/or a mixture of transgenes inserted into the cells. Preferably from approximately 104 to approximately 109 cells are introduced per graft. Cells can be administered concomitantly to different locations such as combined administration intrathecally and intravenously to maximize the chance of targeting into affected areas.

For transplantation into cavities, which may be preferred for spinal cord grafting, tissue is removed from regions close to the external surface of the central nerve system (CNS) to form a transplantation cavity, for example as described by Stenevi et al. (Brain Res. 114:1-20, 1976), by removing bone overlying the brain and stopping bleeding with a material such a gelfoam. Suction may be used to create the cavity. The graft is then placed in the cavity. More than one transplant may be placed in the same cavity using injection of cells or solid tissue implants. Preferably, the site of implantation is dictated by the CNS disorder being treated. Demyelinated MS lesions are distributed across multiple locations throughout the CNS, such that effective treatment of MS may rely more on the migratory ability of the cells to the appropriate target sites.

Intranasal administration of the cells is also contemplated.

MSCs typically down regulate MHC class 2 and are therefore less immunogenic. Embryonal or newborn cells obtained from the cord blood, cord's Warton's gelly or placenta are further less likely to be strongly immunogenic and therefore less likely to be rejected, especially since such cells are immunosuppressive and immunoregulatory to start with.

Notwithstanding, since non-autologous cells may induce an immune reaction when administered to the body several approaches have been developed to reduce the likelihood of rejection of non-autologous cells. Furthermore, since diseases such as multiple sclerosis are inflammatory based diseases, the problem of immune reaction is exacerbated. These include either administration of cells to privileged sites, or alternatively, suppressing the recipient's immune system, providing anti-inflammatory treatment which may be indicated to control autoimmune disorders to start with and/or encapsulating the non-autologous/semi-autologous cells in immunoisolating, semipermeable membranes before transplantation.

As mentioned herein above, the present inventors also propose use of cord and placenta-derived MSCs that express very low levels of MHCII molecules and therefore limit immune response.

The following experiments may be performed to confirm the potential use of newborn's MSCs isolated from the cord I placenta for treatment of neurological disorders:

1) Differentiated MSCs (to various neural cells or neural progenitor cells) may serve as stimulators in one-way mixed lymphocyte culture with allogeneic T-cells and proliferative responses in comparison with T cells responding against allogeneic lymphocytes isolated from the same donor may be evaluated by 3H Thymidine uptake to document hyporesponsiveness.

2) Differentiated MSCs may be added/co-cultured to one-way mixed lymphocyte cultures and to cell cultures with T cell mitogens (phytohemmaglutinin and concanavalin A) to confirm the immunosuppressive effects on proliferative responses mediated by T cells.

3) Cord and placenta cells cultured from Brown Norway rats (unmodified and differentiated), may be enriched for MSCs and these cells may be infused into Lewis rats with induced experimental autoimmune encephalomyelitis (EAE). Alternatively, cord and placenta cells cultured from BALB/c mice, (BALB/cxC57BL/6)F1 or xenogeneic cells from Brown Norway rats (unmodified and differentiated), may be enriched for MSCs and these cells may be infused into C57BL/6 or SJL/j recipients with induced experimental autoimmune encephalomyelitis (EAE). The clinical effects against paralysis may be investigated to evaluate the therapeutic effects of xenogeneic, fully MHC mismatched or haploidentically mismatched MSCs. Such experiments may provide the basis for treatment of patients with a genetic disorder or genetically proned disorder with family member's haploidentical MSCs.

4) BALB/c MSCs cultured from cord and placenta may be transfused with pre-miR labeled with GFP or RFP, which will allow the inventors to follow the migration and persistence of these cells in the brain of C57BL/6 recipients with induced EAE. The clinical effects of labeled MHC mismatched differentiated MSCs may be evaluated by monitoring signs of disease, paralysis and histopathology. The migration and localization of such cells may be also monitored by using fluorescent cells from genetically transduced GFP "green" or Red2 "red" donors.

As mentioned, the present invention also contemplates encapsulation techniques to minimize an immune response.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylideneacetate). J. Microencapsul. 2000, 17: 245-51.

For example, microcapsules are prepared by complexing modified collagen with a per-polymer shell of 2-hydroxyethyl methylacrylate (HEMA), methacrylic acid (MAA) and methyl methacrylate (MMA), resulting in a capsule thickness of 2-5 um. Such microcapsules can be further encapsulated with additional 2-5 um per-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 um (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE™), etanercept, TNF alpha blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium, salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

In any of the methods described herein, the cells can be administered either per se or, preferably as a part of a pharmaceutical composition that further comprises a pharmaceutically acceptable carrier.

As used herein a “pharmaceutical composition” refers to a preparation of one or more of the cell compositions described herein, with other chemical components such as pharmaceutically suitable carders and excipients. The purpose of a pharmaceutical composition is to facilitate administration of the cells to a subject.

Hereinafter, the term “pharmaceutically acceptable earlier” refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term “excipient” refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in “Remington’s Pharmaceutical Sciences,” Mack Publishing Co., Easton, Pa., latest edition, which is incorporated herein by reference.

Suitable routes of administration include direct administration into the circulation (intravenously or intra-arterial), into the spinal fluid or into the tissue or organ of interest. Thus, for example the cells may be administered directly into the brain.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. For example, animal models of demyelinating diseases include shiverer (shi/shi, MBP deleted) mouse, MD rats (PLP deficiency), Jimpy mouse (PLP mutation), dog shaking pup (PLP mutation), twitcher mouse (galactosylceramidase defect, as in human Krabbe disease), trembler mouse (PMP-22 deficiency). Virus induced demyelination model comprise use if Theiler’s virus and mouse hepatitis virus. Autoimmune EAE is a possible model for multiple sclerosis.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient’s condition, (see e.g., Fingl, et al., 1975, in “The Pharmacological Basis of Therapeutics”, Ch. 1 p. 1). For example, a multiple sclerosis patient can be monitored symptomatically for improved motor functions indicating positive response to treatment.

For injection, the active ingredients of the pharmaceutical composition may be formulated in aqueous solutions, preferably in physiologically compatible buffers such as Hank’s solution, Ringer’s solution, or physiological salt buffer.

Dosage amount and interval may be adjusted individually to levels of the active ingredient which are sufficient to effectively treat the brain disease/disorder. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated multiple sclerosis patient will be administered with an amount of cells which is sufficient to alleviate the symptoms of the disease, based on the monitoring indications.

The cells of the present invention may be co-administered with therapeutic agents useful in treating neurodegenerative disorders, such as gangliosides; antibiotics, neurotransmitters, neurohormones, toxins, neurite promoting molecules; and antimetabolites and precursors of neurotransmitter molecules such as L-DOPA.

As used herein the term “about” refers to +/−10%.

As used herein the term “method” refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term “treating” includes abrogating, substantially inhibiting, slowing or reversing the progression of a condition, substantially ameliorating clinical or aesthetical symptoms of a condition or substantially preventing the appearance of clinical or aesthetical symptoms of a condition.

Various embodiments and aspects of the present invention as delineated hereinabove and as claimed in the claims section below find experimental support in the following examples.

The terms “comprises”, “comprising”, “includes”, “including”, “having” and their conjugates mean “including but not limited to”.

The term “consisting of” means “including and limited to”.

The term “consisting essentially of” means that the composition, method or structure may include additional ingredients, steps and/or parts, but only if the additional ingredients, steps and/or parts do not materially alter the basic and novel characteristics of the claimed composition, method or structure.

As used herein, the singular form “a”, “an” and “the” include plural references unless the context clearly dictates otherwise. For example, the term “a compound” or “at least one compound” may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It is noted that for each miR described herein the corresponding sequence (mature and pre) is provided in the sequence listing which should be regarded as part of the specification.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cclls-e-A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization=—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Differentiation of Mesenchymal Stem Cells (MSCs) to Neural Stem Cells (NSCs)

Methods

Mesenchymal stem cells (MSCs) from either bone marrow, adipose, placenta or umbilical cord were plated in high density in bacterial dishes in serum free medium supplemented with 10 mg/ml EGF and bFGF for 10 days. The cells started to aggregate and after 4-5 days were disaggregated mechanically to promote their detachment from the plates. The cells were then maintained for two weeks after which they were analyzed for the expression of NSC markers and for their ability to generate neurons, astrocytes and oligodendrocytes when plated on laminin in low-serum (5%) medium.

The cells were then subjected to miRNA microarray as described.

Results

Figure 1B:
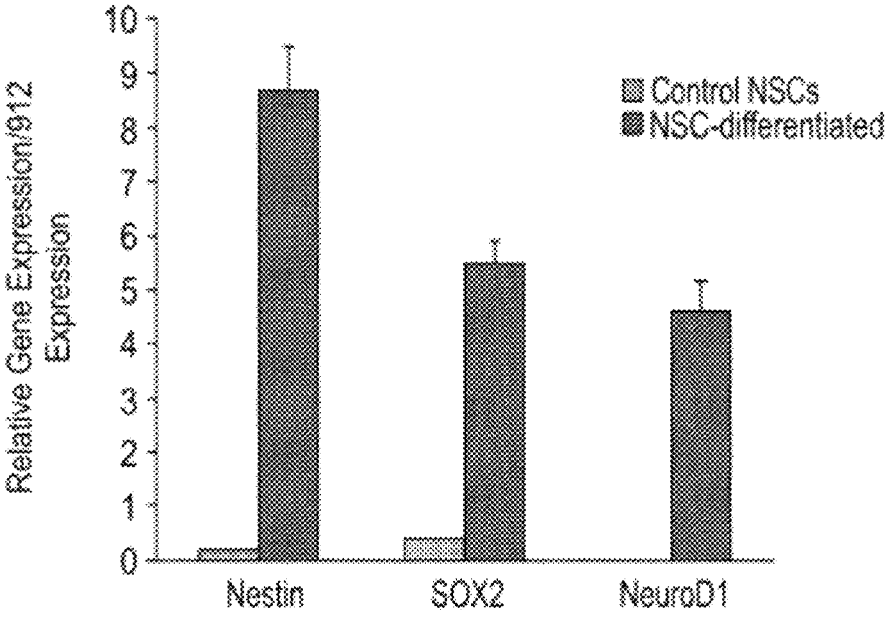

As illustrated in FIGS. 1A-B, the mesenchymal stem cells expressed neuronal markers following neural stem cell differentiation.

Example 2

Changes in miRNA Expression During NSC Differentiation

Materials and Methods miRNAs have been shown to play a role in the differentiation of various neural cells and neural stem cells. To analyze the expression and function of specific miRNAs in MSC-derived NSCs, the MSCs were differentiated towards NSCs as described in Example 1 and miRNA array analysis was performed to the control and differentiated cells. A qRT-PCR microarray was run that contained 96 miRNAs, all of which were related to stem cells and that were divided into subgroups based on their known association with stem cells, neural-related, hematopoietic and organ-related miRNAs.

For analyzing the differential expression of specific miRNA in control and differentiated MSCs, the Stem cell microRNA qPCR array was employed with quantiMiR from SBI company (catalog # RA620A-1), according to the user protocol, the contents of which are incorporated herein by reference. For the qPCR, the Applied Biosystems Power SYBR master mix (cat #4367659) was used.

The system allows for the ability to quantitate fold differences of 95 separate microRNAs between 2 separate experimental RNA samples. The array plate also includes the U6 transcript as a normalization signal. All 95 microRNAs chosen for the array have published implications with regard to potential roles in stem cell self-renewal, hematopoiesis, neuronal development and differentiated tissue identification.

The array plate also includes the U6 RNA as a normalization signal.

Total RNA was isolated from 105-106 cells of control and differentiated MSCs using miRneasy total RNA isolation kit from Qiagen (catalog #217004) that isolate RNA fraction with sizes <200 bp. 500 ng of total RNA was processed according to "SBI Stem Cell MicroRNA qPCR Array with QuantiMir™" (Cat. # RA620A-1) user protocol. For the qPCR, the Applied Biosystems Power SYBR master mix (cat #4367659) was used.

For validation, sybr-green qPCR of the specific miRNA of interest was performed on the same RNA samples processed according to QIAGEN miScript System handbook (cat #218061 & 218073) Hu hsa-miR MicroRNA Profiling Kit (System Biosciences) "SBI Stem Cell MicroRNA qPCR Array with QuantiMir™" (Cat. # RA620A-1) which detects the expression of 96 miRNAs, was used to profile the miRNAs in unmodified BM-MSC compared with MSCs differentiated to astrocytes. 500 ng of total RNA was tagged with poly(A) to its 3' end by poly A polymerase, and reverse-transcribed with oligo-dT adaptors by QuantiMir RT technology. Expression levels of the miRNAs were measured by quantitative PCR using SYBR green reagent and VIIA7, Real-Time PCR System (Applied Biosystems). All miRNAs could be measured with miRNA specific forward primers and a universal reverse primer (SBI). Expression level of the miRNAs was normalized to U6 snRNA, using the comparative CT method for relative quantification as calculated with the following equation: 2-[(CT astrocyte diff miRNA-CT astrocyte endogenous control)-(CTDMEM miRNA-CT DMEM endogenous control).

In addition, an Affymetrix miRNA 3.0 array was used to compare BM-MSCs and human NSCs and identify differentially expressed miRNAs.

Results

As presented in FIGS. 2, 3 and 4A, there were significant changes in the expression of specific miRNA of each group between the control MSCs and the differentiated ones.

The results of the Affymetrix miRNA 3.0 array analysis are detailed in Table 1 herein below.

Using a nestin promoter based reporter assay, the present inventors confirmed that overexpression of miR-20b, miR-935, miR-891 and miR-378 also induced differentiation of the MSCs into NSCs (FIG. 4B).

Similarly, silencing of miR-138, miR-214, miR-199a and miR-199b decreased the mesenchymal phenotypes of all the MSCs and induced their NSC differentiation (FIG. 4C).

Co-transfection of the MSCs with combination of miR-20b or miR-378 with antagomiR-138 further increased the differentiation of the MSCs to nestin positive cells (FIG. 4D).

As presented in FIGS. 4E-F, overexpression of antagomiR-138 and miR-891 mimic induced a significant increase in the generation of nestin positive cells in the transfected MSCs as demonstrated by the increased fluorescence intensity of cells transduced with the nestin-GFP reporter.

TABLE 1

| MSCs/NSCs miRNA | Up regulated Fold change | MSCs/NSCs miRNA | Down regulated Fold change | miRNA | Fold change |
|---|---|---|---|---|---|
| hsa-miR-145_st | 1379.78 | hsa-let-7c_st | −1.53698 | hsa-miR-324-3p_st | −7.34456 |
| hsa-miR-143_st | 752.7381 | hsa-miR-665_st | −1.58884 | hsa-miR-20a_st | −7.83858 |
| hsa-miR-214_st | 552.6854 | hsa-miR-4258_st | −1.61841 | hsa-miR-501-5p_st | −8.36351 |
| hsa-miR-199a-3p_st | 511.1263 | hsa-miR-361-3p_st | −1.63684 | hsa-miR-330-3p_st | −8.71869 |
| hsa-miR-199a-5p_st | 362.5667 | hsa-miR-374a-star_st | −1.76218 | hsa-miR-874_st | −9.13392 |
| hsa-miR-199b-3p_st | 347.4311 | hsa-miR-892b_st | −1.85672 | hsa-miR-500_st | −9.68441 |
| hsa-miR-138_st | 229.2463 | hsa-miR-361-5p_st | −1.90874 | hsa-miR-25_st | −9.86881 |
| hsa-miR-31_st | 190.5331 | hsa-miR-181a_st | −1.93941 | hsa-miR-769-5p_st | −10.1382 |
| hsa-miR-21_st | 59.83459 | hsa-miR-16_st | −2.19583 | hsa-miR-125b-2-star_st | −10.3325 |
| hsa-miR-193a-5p_st | 23.8986 | hsa-miR-636_st | −2.27398 | hsa-miR-130b_st | −16.7436 |
| hsa-miR-224-star_st | 21.60842 | hsa-miR-4284_st | −2.79417 | hsa-miR-504_st | −16.9435 |
| hsa-miR-196a_st | 21.38142 | hsa-miR-1208_st | −3.00768 | hsa-miR-181a-2-star_st | −17.7877 |
| hsa-miR-487b_st | 19.18475 | hsa-miR-1274b_st | −3.01855 | hsa-miR-885-3p_st | −20.1501 |
| hsa-miR-409-5p_st | 17.45522 | hsa-miR-30c-2-star_st | −3.46182 | hsa-miR-1246_st | −21.0971 |
| hsa-miR-193b-star_st | 10.34438 | hsa-miR-501-3p_st | −3.49025 | hsa-miR-92b_st | −22.8735 |
| hsa-miR-379_st | 9.571106 | hsa-miR-92a_st | −3.7152 | hsa-miR-362-5p_st | −23.3686 |
| hsa-miR-21-star_st | 8.401508 | hsa-miR-378b_st | −3.72739 | hsa-miR-572_st | −23.3743 |

TABLE 1-continued

| MSCs/NSCs miRNA | Up regulated Fold change | MSCs/NSCs miRNA | Down regulated Fold change | miRNA | Fold change |
|---|---|---|---|---|---|
| hsa-miR-27a-star_st | 7.080883 | hsa-miR-1287_st | −3.87466 | hsa-miR-4270_st | −24.4173 |
| hsa-miR-27a_st | 6.122331 | hsa-miR-425-star_st | −4.0524 | hsa-miR-378c_st | −26.6758 |
| hsa-miR-4317_st | 5.715753 | hsa-miR-324-5p_st | −4.37339 | hsa-miR-93-star_st | −28.4948 |
| hsa-miR-193b_st | 4.920511 | hsa-miR-3178_st | −4.40631 | hsa-miR-149_st | −28.7369 |
| hsa-miR-27b_st | 4.889609 | hsa-miR-219-1-3p_st | −4.52146 | hsa-miR-363_st | −28.9968 |
| hsa-miR-22_st | 4.798265 | hsa-miR-197_st | −4.609 | hsa-miR-9_st | −31.2283 |
| hsa-miR-574-3p_st | 3.402782 | hsa-miR-181b_st | −4.61406 | hsa-miR-18a_st | −32.3908 |
| hsa-miR-4288_st | 3.375774 | hsa-miR-500-star_st | −4.72807 | hsa-miR-891a_st | −33.1912 |
| hsa-miR-23a_st | 3.34163 | hsa-miR-106b_st | −4.96582 | hsa-miR-346_st | −38.7283 |
| hsa-miR-221-star_st | 3.09015 | hsa-miR-502-3p_st | −4.97984 | hsa-miR-124_st | −50.7583 |
| hsa-miR-2113_st | 3.030064 | hsa-miR-30c_st | −5.17107 | hsa-miR-497_st | −72.2314 |
| hsa-let-7i_st | 2.551577 | hsa-miR-1275_st | −5.29365 | hsa-miR-378_st | −73.6306 |
| hsa-miR-24_st | 2.300083 | hsa-miR-422a_st | −5.54416 | hsa-miR-1231_st | −82.7066 |
| hsa-miR-23b_st | 2.217338 | hsa-miR-93_st | −5.6233 | hsa-miR-139-5p_st | −92.6078 |
| hsa-miR-299-3p_st | 2.201907 | hsa-miR-181d_st | −5.74741 | hsa-miR-3180-3p_st | −94.3695 |
| hsa-miR-518c-star_st | 2.197822 | hsa-miR-1307_st | −5.82664 | hsa-miR-9-star_st | −114.107 |
| hsa-miR-221_st | 2.186328 | hsa-miR-1301_st | −5.84397 | hsa-miR-935_st | −140.688 |
| hsa-miR-431-star_st | 2.177192 | hsa-miR-99a_st | −5.88481 | hsa-miR-20b_st | −156.762 |
| hsa-miR-523_st | 2.116276 | hsa-miR-505-star_st | −5.9383 | | |
| hsa-miR-4313_st | 1.937531 | hsa-miR-1202_st | −5.94177 | | |
| hsa-miR-559_st | 1.916531 | hsa-miR-128_st | −6.05212 | | |
| hsa-miR-614_st | 1.894046 | hsa-miR-532-5p_st | −6.11976 | | |
| hsa-miR-653_st | 1.803374 | hsa-miR-195_st | −6.5161 | | |
| hsa-miR-2278_st | 1.675887 | hsa-miR-532-3p_st | −6.66014 | | |
| v11_hsa-miR-768-5p_st | 1.647103 | hsa-miR-106a_st | −6.91155 | | |
| hsa-miR-154-star_st | 1.608659 | hsa-miR-17_st | −6.91565 | | |
| hsa-miR-302a-star_st | 1.598961 | hsa-miR-1271_st | −7.05548 | | |
| hsa-miR-3199_st | 1.580479 | hsa-miR-769-3p_st | −7.1367 | | |
| hsa-miR-3137_st | 1.476948 | hsa-miR-15b_st | −7.31636 | | |

Example 3 miRNAs that Play a Role in the Differentiation of MSCs to NSCs

The present inventors further examined the role of the specific miRNAs that were found to be altered in the miR microarray on the differentiation of the MSCs to NSCs. These experiments were performed by transfecting MSCs with either specific or combination of mature miRNA mimics or miRNA inhibitors and then their ability to generate neurospheres and express the markers nestin and Sox2 was examined.

Results

It was found that the inhibition of let-7 together with expression of miR-124 increased NSC differentiation.

In addition, it was found that up-regulation of the following miRNAs: miR302b, miR-371, miR-134, miR-219, miR-154, miR-155, miR-32, miR-33, miR-126 and miR-127 and down-regulation of the following miRs-miR-10b, miR-142-3p, miR-131a, miR-125b, miR-153 and miR-181a either alone or in various combinations induced differentiation of the MSCs to NSCs albeit to different degrees.

In addition to the miRNAs that were described in the miRNA array, it was also found that transfection of the MSCs with miR-132 and miR-137 also increased the NSC differentiation.

Example 4

Additional Factors that Promote the Differentiation of MSCs to NSCs

Related to testis-specific, vespid and pathogenesis protein 1 (RTVP-1) was cloned from human GBM cell lines by two groups and was termed glioma pathogenesis-related protein-GLIPR1 or RTVP-1 [3]. RTVP-1 contains a putative signal peptide, a transmembrane domain and a SCP domain, with a yet unknown function which is also found in other RTVP-1 homologs including TPX-1 [4], the venom allergen antigen 5 [5] and group 1 of the plant pathogenesis-related proteins (PR-1). It has recently been reported that RTVP-1 acts as a tumor promoter in gliomas. Thus, the expression of RTVP-1 correlates with the degree of malignancy of astrocytic tumors and over-expression of RTVP-1 increases cell proliferation, invasion, migration and anchorage independent growth. Moreover, silencing of RTVP-1 induces apoptosis in glioma cell lines and primary glioma cultures [6]. Interestingly, RTVP-1 acts as a tumor suppressor in prostate cancer cells and adenovirus mediated delivery of RTVP-1 has therapeutic effects in a mouse prostate cancer model [7-9].

Results

Expression of RTVP-1 in MSCs is very high, as determined by Western blot (FIG. 5A). Moreover, silencing of RTVP-1 in MSCs abrogated their ability to differentiate to mesenchymal lineage cells (FIGS. 5C-D).

Further, silencing of RTVP-1 in MSCs increased the expression of both nestin and Sox 2 and some levels of beta 3 tubulin (data not shown). Interestingly, it was found that RTVP-1 is a novel target of miR-137, suggesting that the positive effect of miR-137 on the NSC differentiation of MSCs may be mediated by RTVP-1.

To further examine the role of RTVP-1, its expression was examined in MSCs, NSCs and in MSCs that were differentiated into NSCs. Human NSCs did not express RTVP-1 at all (data not shown) and the expression of RTVP-1 in MSCs was significantly higher than that of MSCs differentiated to NSCs irrespective of the source of MSCs that were examined (FIG. 5E).

The effect of RTVP-1 overexpression in human NSCs was examined. It was found that these cells acquired mesenchymal phenotypes and especially were predisposed to differentiate into adipocytes (data not shown).

Silencing of RTVP-1 in the different MSCs examined increased the expression of nestin in these cells (FIG. 5F).

To further analyze the effect of RTVP-1 on mesenchymal transformation, gene array analysis was performed on BM-MSCs in which the expression of RTVP-1 was silenced. Silencing of RTVP-1 decreased the expression of ALDH1A3 by 3.2-fold, VAV3 by 15 fold, CD200 by 5 fold and the sternness markers Oct4, Nanog and Sox2 by 2.3, 3.4 and 4.2, respectively. Collectively these results indicate that RTVP-1 decreases the proliferation and sternness signature of these cells.

In contrast, RTVP-1 silencing increased the expression of certain genes such as nestin (3.4 fold), NKX2.2 (4.7 fold) and calcium channel, voltage dependent (3 fold).

Together, these results implicate RTVP-1 as a major mesenchymal regulator and demonstrate that silencing of RTVP-1 induces differentiation of MSCs to cells with neural phenotypes.

Example 5

Differentiation of Neural Progenitor Cells to Motor Neurons

Materials and Methods

Plates were coated with 20 μg/ml laminin overnight and were then washed twice with PBS. The NPC were plated in the confluency of 50% and after 24 hr were incubated with priming medium: NM medium with heparin (use 10 μg/mL) and bFGF (100 μg/mL) for 5 days. After day 5 the medium was changed to the differentiation medium: F12 with 1 mL of B27 in 50 mL F12 (or 2%), retinoic acid (RA, 1 μM), and SHH (200 ng/mL). The RA was added every other day. After 5 days GDNF and BDNF were added to the medium (10 ng/mL).

Results

In the developing spinal cord, there is sequential generation of motor neurons (MNs) and oligodendrocytes (OLPs). There are common progenitors called pMN that first generate MN and then oligodendrocytes. The basic helix-loop-helix (bHLH) transcription factor Olig2, is expressed in the pMN domain and it's one of the important transcription factors that play a role in the development of both cell types. Over-expression of Olig2 in MSCs that were grow in NM medium supplemented with 200 ng/ml recombinant SHH, 20 ng/ml of each, GDNF, BDNF, CNTF and NT-3 and 1 mM retinoic acid induced the expression of two specific markers of motor neurons Hb9 and Islet1 (FIGS. 6A-D).

Example 6

Involvement of miRNAs in the Differentiation of NPCs to Motor Neurons

Materials and Methods

To identify specific miRNAs involved with motor neuron differentiation, the present inventors differentiated two types of neural stem/progenitor cells into motor neurons at different stages of development using the protocol described in Example 5. The characterization of the cells as motor neurons was characterized by the expression of the specific markers, islet1, HB9 and the neuronal markers neurofilament and tubulin.

To analyze the expression and function of specific miRNAs in motor neurons the neural progenitor cell system described herein above was used. miRNA array analysis was performed on the control and differentiated cells. A qRT-PCR microarray that contained 96 miRNAs, all of which were related to stem cells and that were divided into subgroups based on their known association with stem cells, neural-related, hematopoietic and organ-related miRNAs, as described in Example 2.

Results

As illustrated in FIGS. 7A-B, neural stem cells may be induced to differentiate into motor neurons.

As presented in FIGS. 8-10, there were significant changes in the expression of specific miRNA of each group between the control MSCs and the differentiated MSCs.

qRT-PCR studies were performed to validate the differences in the miRNA expression that were observed between the control and differentiated cells.

Similar to the results that were obtained with the microarray data, the qRT-PCR results demonstrated a decrease in miRs, 372, 373, 141, 199a, 32, 33, 221 and 223.

In contrast a significant increase was observed in all the miRNAs that increased in the array and specifically the following miRNAs: miR-368, 302b, 365-3p, 365-5p, Let-7a, Let-7b, 218, 134, 124, 125a, 9, 154, 20a, 130a.

The present inventors further examined the role of the specific miRNAs in the differentiation of MSCs to motor neurons. It was found that the combination of Let-7a and miR-124, 368 and miR-154 increased the expression of Hb9 and Islet-1. Similarly, transfection with combinations of miR-125a, 9, 130a and 218, 134 and 20a together and in combination with miRNA inhibitors of miR-141, 32, 33, 221, 223 and miR373 also induced differentiation of MSCs to either motor neuron progenitors or to immature motor neurons.

Example 7

Sequences

TABLE 2

| Name | Sequence of mature miRNA | Sequence of premiRNA |
|---|---|---|
| hsa-let-7a | seq id no: 1 | seq id no: 73 |
| | | seq id no: 74 |
| | | seq id no: 75 |
| hsa-let-7b | seq id no: 2 | seq id no: 76 |
| hsa-let-7c | seq id no: 3 | seq id no: 77 |
| hsa-let-7d | seq id no: 4 | seq id no: 78 |
| hsa-let-7e | seq id no: 5 | seq id no: 79 |
| hsa-let-7f | seq id no: 6 | seq id no: 80 |
| hsa-let-7g | seq id no: 7 | seq id no: 81 |
| hsa-let-7i | seq id no: 8 | seq id no: 82 |
| hsa-mir-106a | seq id no: 9 | seq id no: 83 |
| hsa-mir-106b | seq id no: 10 | seq id no: 84 |
| hsa-mir-1294 | seq id no: 11 | seq id no: 85 |
| hsa-mir-1297 | seq id no: 12 | seq id no: 86 |
| hsa-mir-143 | seq id no: 13 | seq id no: 87 |
| hsa-mir-144 | seq id no: 14 | seq id no: 88 |
| hsa-mir-145 | seq id no: 15 | seq id no: 89 |
| hsa-mir-17 | seq id no: 16 | seq id no: 90 |
| miR-181a | seq id no: 17 | seq id no: 91 |
| miR-181a | seq id no: 18 | seq id no: 92 |
| miR-181b | seq id no: 19 | seq id no: 93 |
| miR-181b | seq id no: 20 | seq id no: 94 |
| miR-181c | seq id no: 21 | seq id no: 95 |
| hsa-mir-181d | seq id no: 22 | seq id no: 96 |
| hsa-mir-199a-3p | seq id no: 23 | seq id no: 97 |
| hsa-mir-199b-3p | seq id no: 24 | seq id no: 98 |
| hsa-mir-202 | seq id no: 25 | seq id no: 99 |
| hsa-mir-20a | seq id no: 26 | seq id no: 100 |
| hsa-mir-20b | seq id no: 27 | seq id no: 101 |
| hsa-mir-2113 | seq id no: 28 | seq id no: 102 |
| hsa-mir-25 | seq id no: 29 | seq id no: 103 |
| hsa-mir-26a | seq id no: 30 | seq id no: 104 |
| | seq id no: 31 | seq id no: 105 |
| hsa-mir-26b | seq id no: 32 | seq id no: 106 |
| hsa-mir-29a | seq id no: 33 | seq id no: 107 |
| hsa-mir-29b | seq id no: 34 | seq id no: 108 |
| | | seq id no: 109 |
| hsa-mir-29c | seq id no: 35 | seq id no: 110 |
| hsa-mir-3129-5p | seq id no: 36 | seq id no: 111 |
| hsa-mir-3177-5p | seq id no: 37 | seq id no: 112 |
| hsa-mir-32 | seq id no: 38 | seq id no: 113 |
| hsa-mir-326 | seq id no: 39 | seq id no: 114 |
| hsa-mir-330-5p | seq id no: 40 | seq id no: 115 |
| hsa-mir-363 | seq id no: 41 | seq id no: 116 |
| hsa-mir-3659 | seq id no: 42 | seq id no: 117 |
| hsa-mir-3662 | seq id no: 43 | seq id no: 118 |
| hsa-mir-367 | seq id no: 44 | seq id no: 119 |
| hsa-mir-372 | seq id no: 45 | seq id no: 120 |
| hsa-mir-373 | seq id no: 46 | seq id no: 121 |
| hsa-mir-3927 | seq id no: 47 | seq id no: 122 |
| hsa-mir-4262 | seq id no: 48 | seq id no: 123 |
| hsa-mir-4279 | seq id no: 49 | seq id no: 124 |
| hsa-mir-4458 | seq id no: 50 | seq id no: 125 |
| hsa-mir-4465 | seq id no: 51 | seq id no: 126 |

TABLE 2-continued

| Name | Sequence of mature miRNA | Sequence of premiRNA |
|---|---|---|
| hsa-mir-4500 | seq id no: 52 | seq id no: 127 |
| hsa-mir-4658 | seq id no: 53 | seq id no: 128 |
| hsa-mir-4724-3p | seq id no: 54 | seq id no: 129 |
| hsa-mir-4742-3p | seq id no: 55 | seq id no: 130 |
| hsa-mir-4770 | seq id no: 56 | seq id no: 131 |
| hsa-mir-519d | seq id no: 57 | seq id no: 132 |
| hsa-mir-520a-3p | seq id no: 58 | seq id no: 133 |
| hsa-mir-520b | seq id no: 59 | seq id no: 134 |
| hsa-mir-520c-3p | seq id no: 60 | seq id no: 135 |
| hsa-mir-520d-3p | seq id no: 61 | seq id no: 136 |
| hsa-mir-520d-5p | seq id no: 62 | seq id no: 137 |
| hsa-mir-520e | seq id no: 63 | seq id no: 138 |
| hsa-mir-524-5p | seq id no: 64 | seq id no: 139 |
| hsa-mir-642b | seq id no: 65 | seq id no: 140 |
| hsa-mir-656 | seq id no: 66 | seq id no: 141 |
| hsa-mir-767-5p | seq id no: 67 | seq id no: 142 |
| hsa-mir-92a | seq id no: 68 | seq id no: 143 |
| | seq id no: 69 | seq id no: 144 |
| hsa-mir-92b | seq id no: 70 | seq id no: 145 |
| hsa-mir-93 | seq id no: 71 | seq id no: 146 |
| hsa-mir-98 | seq id no: 72 | seq id no: 147 |

TABLE 3

| Name | Sequence of mature | Sequence of premiRNA |
|---|---|---|
| hsa-mir-410 | seq id no: 148 | seq id no: 156 |
| hsa-mir-3163 | seq id no: 149 | seq id no: 157 |
| hsa-mir-148a | seq id no: 150 | seq id no: 158 |
| hsa-mir-148b | seq id no: 151 | seq id no: 159 |
| hsa-mir-152 | seq id no: 152 | seq id no: 160 |
| hsa-mir-3121-3p | seq id no: 153 | seq id no: 161 |
| hsa-mir-495 | seq id no: 154 | seq id no: 162 |
| hsa-mir-4680-3p | seq id no: 155 | seq id no: 163 |

TABLE 4

| Name | Sequence of mature | PMIR id | Sequence of premiRNA |
|---|---|---|---|
| miR-92ap | seq id no: 164 | MI0000093 | seq id no: 269 |
| | seq id no: 165 | MI0000094 | seq id no: 270 |
| miR-21 | seq id no: 166 | MI0000077 | seq id no: 271 |
| miR-26a 5P | seq id no: 167 | MI0000083 | seq id no: 272 |
| | seq id no: 168 | MI0000750 | seq id no: 273 |
| miR-18a | seq id no: 169 | MI0000072 | seq id no: 274 |
| miR-124 | seq id no: 170 | MI0000445 | seq id no: 275 |
| | seq id no: 171 | MI0000443 | seq id no: 276 |
| | seq id no: 172 | MI0000444 | seq id no: 277 |
| miR-99a | seq id no: 173 | MI0000101 | seq id no: 278 |
| miR-30c | seq id no: 174 | MI0000736 | seq id no: 279 |
| | | MI0000254 | seq id no: 280 |
| miR-301a 3P | seq id no: 175 | MI0000745 | seq id no: 281 |
| miR-145-50 | seq id no: 176 | MI0000461 | seq id no: 282 |
| miR-143-3p | seq id no: 177 | MI0000459 | seq id no: 283 |
| miR-373 3P | seq id no: 178 | MI0000781 | seq id no: 284 |
| miR-20b | seq id no: 179 | MI0001519 | seq id no: 285 |
| miR-29c 3P | seq id no: 180 | MI0000735 | seq id no: 286 |
| miR-29b 3P | seq id no: 181 | MI0000105 | seq id no: 287 |
| | | MI0000107 | seq id no: 288 |
| miR-143 | | | |
| let-7g | seq id no: 182 | MI0000433 | seq id no: 289 |
| let-7a | seq id no: 183 | MI0000060 | seq id no: 290 |
| | | MI0000061 | seq id no: 291 |
| | | MI0000062 | seq id no: 292 |
| let-7b | seq id no: 184 | MI0000063 | seq id no: 293 |
| miR-98 | seq id no: 185 | MI0000100 | seq id no: 294 |
| miR-30a* | seq id no: 186 | MI0000088 | seq id no: 295 |
| miR-17 | seq id no: 187 | MI0000071 | seq id no: 296 |
| miR-1-1 | seq id no: 188 | MI0000651 | seq id no: 297 |
| miR-1-2 | seq id no: 189 | MI0000437 | seq id no: 298 |

TABLE 4-continued

| Name | Sequence of mature | PMIR id | Sequence of premiRNA |
|---|---|---|---|
| miR-192 | seq id no: 190 | MI0000234 | seq id no: 299 |
| miR-155 | seq id no: 191 | MI0000681 | seq id no: 300 |
| miR-516-ap a1-5p-- | seq id no: 192 | MI0003180 | seq id no: 301 |
| a2-3p-- | seq id no: 193 | MI0003181 | seq id no: 302 |
| miR-31 | seq id no: 194 | MI0000089 | seq id no: 303 |
| miR-181a | seq id no: 195 | MI0000289 | seq id no: 304 |
| | seq id no: 196 | MI0000269 | seq id no: 305 |
| miR-181b | seq id no: 197 | MI0000270 | seq id no: 306 |
| | seq id no: 198 | MI0000683 | seq id no: 307 |
| miR-181c | seq id no: 199 | MI0000271 | seq id no: 308 |
| miR-34-c | seq id no: 200 | MI0000743 | seq id no: 309 |
| miR-34b* | seq id no: 201 | MI0000742 | seq id no: 310 |
| miR-103a | seq id no: 202 | MI0000109 | seq id no: 311 |
| | seq id no: 203 | MI0000108 | seq id no: 312 |
| miR-210 | seq id no: 204 | MI0000286 | seq id no: 313 |
| miR-16 | seq id no: 205 | MI0000070 | seq id no: 314 |
| | seq id no: 206 | MI0000115 | seq id no: 315 |
| miR-30a | seq id no: 207 | MI0000088 | seq id no: 316 |
| miR-31 | seq id no: 208 | MI0000089 | seq id no: 317 |
| miR-222 | seq id no: 209 | MI0000299 | seq id no: 318 |
| miR-17 | seq id no: 210 | MI0000071 | seq id no: 319 |
| miR-17* | seq id no: 211 | MI0000071 | seq id no: 320 |
| miR-200b | seq id no: 212 | MI0000342 | seq id no: 321 |
| miR-200c | seq id no: 213 | MI0000650 | seq id no: 322 |
| miR-128 | seq id no: 214 | MI0000447 | seq id no: 323 |
| | | MI0000727 | seq id no: 324 |
| miR-503 | seq id no: 215 | MI0003188 | seq id no: 325 |
| miR-424 | seq id no: 216 | MI0001446 | seq id no: 326 |
| miR-195 | seq id no: 217 | MI0000489 | seq id no: 327 |
| miR-1256 | seq id no: 218 | MI0006390 | seq id no: 328 |
| miR-203a | seq id no: 219 | MI0000283 | seq id no: 329 |
| miR-199 ?? | | | |
| hsa-miR-199a-3p__st | seq id no: 220 | MI0000242 | seq id no: 330 |
| hsa-miR-199a-5p__st | seq id no: 221 | MI0000242 | seq id no: 331 |
| hsa-miR-199b-3p__st | seq id no: 222 | MI0000282 | seq id no: 332 |
| miR-93 | seq id no: 223 | MI0000095 | seq id no: 333 |
| miR-98 | seq id no: 224 | MI0000100 | seq id no: 334 |
| miR-125-a | seq id no: 225 | MI0000469 | seq id no: 335 |
| miR-133a | seq id no: 226 | MI0000450 | seq id no: 336 |
| | | MI0000451 | seq id no: 337 |
| miR-133b | seq id no: 227 | MI0000822 | seq id no: 338 |
| miR-126 | seq id no: 228 | MI0000471 | seq id no: 339 |
| miR-194 | seq id no: 229 | MI0000488 | seq id no: 340 |
| | | MI0000732 | seq id no: 341 |
| miR-346 | seq id no: 230 | MI0000826 | seq id no: 342 |
| miR-15b | seq id no: 231 | MI0000438 | seq id no: 343 |
| miR-338-3p | seq id no: 232 | MI0000814 | seq id no: 344 |
| miR-373 | | | |
| miR-205 | seq id no: 233 | MI0000285 | seq id no: 345 |
| miR-210 | | | |
| miR-125 | | | |
| miR-1226 | seq id no: 234 | MI0006313 | seq id no: 346 |
| miR-708 | seq id no: 235 | MI0005543 | seq id no: 347 |
| miR-449 | seq id no: 236 | MI0001648 | seq id no: 348 |
| miR-422 | seq id no: 237 | MI0001444 | seq id no: 349 |
| miR-340 | seq id no: 238 | MI0000802 | seq id no: 350 |
| miR-605 | seq id no: 239 | MI0003618 | seq id no: 351 |
| miR-522 | seq id no: 240 | MI0003177 | seq id no: 352 |
| miR-663 | seq id no: 241 | MI0003672 | seq id no: 353 |
| miR-130a | seq id no: 242 | MI0000448 | seq id no: 354 |
| miR-130b | seq id no: 243 | MI0000748 | seq id no: 355 |
| miR-942 | seq id no: 244 | MI0005767 | seq id no: 356 |
| miR-572 | seq id no: 245 | MI0003579 | seq id no: 357 |
| miR-520 | | | |
| miR-639 | seq id no: 246 | MI0003654 | seq id no: 358 |
| miR-654 | seq id no: 247 | MI0003676 | seq id no: 359 |
| miR-519 | | | |
| miR-204 | | seq id no: 248 | MI0000284 |
| miR-224 | seq id no: 249 | MI0000301 | seq id no: 360 |
| miR-616 | seq id no: 250 | MI0003629 | seq id no: 361 |
| miR-122 | seq id no: 251 | MI0000442 | seq id no: 362 |
| miR-299 3p- | seq id no: 252 | MI0000744 | seq id no: 363 |
| 5p- | seq id no: 253 | | seq id no: 364 |

TABLE 4-continued

| Name | Sequence of mature | PMIR id | Sequence of premiRNA |
|---|---|---|---|
| miR-100 | seq id no: 254 | MI0000102 | |
| miR-138 | seq id no: 255 | MI0000476 | seq id no: 365 |
| miR-140 | seq id no: 256 | MI0000456 | seq id no: 366 |
| miR-375 | seq id no: 257 | MI0000783 | seq id no: 367 |
| miR-217 | seq id no: 258 | MI0000293 | seq id no: 368 |
| miR-302 | | | seq id no: 369 |
| miR-372 | seq id no: 259 | MI0000780 | |
| miR-96 | seq id no: 260 | MI0000098 | seq id no: 370 |
| miR-127-3p | seq id no: 261 | MI0000472 | seq id no: 371 |
| miR-449 | | | seq id no: 372 |
| miR-135b | seq id no: 262 | MI0000810 | |
| miR-101 | seq id no: 263 | MI0000103 | seq id no: 373 |
| | | MI0000739 | seq id no: 374 |
| miR-326 | seq id no: 264 | MI0000808 | seq id no: 375 |
| miR-3245p-3p- | seq id no: 265 | MI0000813 | seq id no: 376 |
| | seq id no: 266 | MI0000813 | seq id no: 377 |
| miR-335 | seq id no: 267 | MI0000816 | seq id no: 378 |
| miR-141 | seq id no: 268 | MI0000457 | seq id no: 379 |

TABLE 5

| Name | Sequence of mature miRNA | Sequence of premiRNA |
|---|---|---|
| miR-1275 | seq id no: 381 | seq id no: 414 |
| miR-891a | seq id no: 382 | seq id no: 415 |
| miR-154 | seq id no: 383 | seq id no: 416 |
| miR-1202 | seq id no: 384 | seq id no: 417 |
| miR-572 | seq id no: 385 | seq id no: 418 |
| miR-935a | seq id no: 386 | seq id no: 419 |
| miR-4317 | seq id no: 387 | seq id no: 420 |
| miR-153 | seq id no: 388 | seq id no: 421 |
| | | seq id no: 422 |
| miR-4288 | seq id no: 389 | seq id no: 423 |
| miR-409-5p | seq id no: 390 | seq id no: 424 |
| miR-193a-5p | seq id no: 391 | seq id no: 425 |
| miR-648 | seq id no: 392 | seq id no: 426 |
| miR-368 | | |
| miR-365 | seq id no: 393 | seq id no: 427 |
| miR-500 | seq id no: 394 | seq id no: 428 |
| miR-491 | seq id no: 395 | seq id no: 429 |
| hsa-miR-199a-3p__st | seq id no: 396 | seq id no: 430 |
| | seq id no: 397 | seq id no: 431 |
| hsa-miR-199a-5p__st | seq id no: 398 | seq id no: 432 |
| | seq id no: 399 | seq id no: 433 |
| miR-2113 | seq id no: 400 | seq id no: 434 |
| miR-372 | seq id no: 401 | seq id no: 435 |
| miR-373 | seq id no: 402 | seq id no: 436 |
| miR-942 | seq id no: 403 | seq id no: 437 |
| miR-1293 | seq id no: 404 | seq id no: 438 |
| miR-18 | seq id no: 405 | seq id no: 439 |
| miR-1182 | seq id no: 406 | seq id no: 440 |
| miR-1185 | seq id no: 407 | seq id no: 441 |
| | | seq id no: 442 |
| miR-1276 | seq id no: 408 | seq id no: 443 |
| miR-193b | seq id no: 409 | seq id no: 444 |
| miR-1238 | seq id no: 410 | seq id no: 445 |
| miR-889 | seq id no: 411 | seq id no: 446 |
| miR-370 | seq id no: 412 | seq id no: 447 |
| miR-548-d1 | seq id no: 413 | seq id no: 448 |

TABLE 6

| mir designation | seq id no: |
|---|---|
| hsa-miR-302b | seq id no: 449 |
| hsa-miR-371 | seq id no: 450 |
| hsa-miR-134 | seq id no: 451 |
| hsa-miR-219 | seq id no: 452 |
| hsa-miR-154 | seq id no: 453 |

TABLE 6-continued

| mir designation | seq id no: |
|---|---|
| hsa-miR-155 | seq id no: 454 |
| hsa-miR-32 | seq id no: 455 |
| hsa-miR-33 | seq id no: 456 |
| hsa-miR-126 | seq id no: 457 |
| hsa-miR-127 | seq id no: 458 |
| hsa-miR-132 | seq id no: 459 |
| hsa-miR-137 | seq id no: 460 |
| hsa-miR-10b | seq id no: 461 |
| hsa-miR-142-3p | seq id no: 462 |
| hsa-miR-131a | |
| hsa-miR-125b | seq id no: 463 |
| hsa-miR-153 | seq id no: 464 |
| hsa-miR-181a | seq id no: 465 |
| hsa-miR-123 | |
| hsa-miR-let-7a | seq id no: 466 |
| hsa-miR-let-7b | seq id no: 467 |
| hsa-miR-368 | seq id no: 468 |
| hsa-miR-365-3p | |
| hsa-miR-365-5p | |
| hsa-miR-218 | seq id no: 469 |
| hsa-miR-124 | seq id no: 470 |
| hsa-miR-125a | seq id no: 471 |
| hsa-miR-9 | seq id no: 472 |
| hsa-miR-20a | seq id no: 473 |
| hsa-miR-130a | seq id no: 474 |
| hsa-miR-372 | seq id no: 475 |
| hsa-miR-373 | seq id no: 476 |
| hsa-miR-141 | seq id no: 477 |
| hsa-miR-199a | seq id no: 478 |
| hsa-miR-221 | seq id no: 479 |
| hsa-miR-223 | seq id no: 480 |

Example 8 miRNAs that Play a Role in the Differentiation of MSCs to Motor Neurons

Materials and Methods

Plates were coated with 20 μg/ml laminin overnight and were then washed twice with PBS. The MSCs were plated in the confluency of 50% and after 24 hr were incubated with priming medium: NM medium with heparin (use 10 μg/mL) and bFGF (10 μg/mL) for 5 days. After day 5 the medium was changed to the differentiation medium: F12 with 1 mL of B27 in 50 μL F12 (or 2%), retinoic acid (RA, 0.1-1 μM), and SHH (200 ng/mL). The RA was added every other day. After 5 days GDNF and BDNF were added to the medium (10 ng/mL).

Results

Transfection of MSCs with various miRs and miR inhibitors to induce trans-differentiation to motor neuron progenitors and immature motor neurons was already discussed in Example 6, however, further effective combinations are herein described. MSCs were transfected with a control miR, miR-9, miR-218, miR-375, all three miRs, all three miRs and an antagomir to miR-221, and all three miRs and an antagomir to miR-373 and mRNA expression of the motor neuron markers Islet1 and HB9 was measured (FIG. 11). Expression was standardized to the control miR transfected MSCs, which was set as 1, and the results are presented in Table 7. Each miR on its own caused about a doubling in expression of Islet1 and HB9. Unexpectedly, expression of all three miRs had a synergistic effect on trans-differentiation and Islet1 was increased by more than 5 fold, while HB9 was increased by more than 6 fold. The three miR combination was also transfected in combination with antagomirs that knockdown expression of miR-221 or miR-373. These combinations were even more effective, as 8-9 fold increases in Islet1 and HB9 were observed.

TABLE 7

(Relative mRNA expression/S12 mRNA)

| | Islet1 | HB9 |
|---|---|---|
| Con miR | 1 | 1 |
| miR-9 | 1.8 | 2.12 |
| miR-218 | 2.09 | 1.96 |
| miR-375 | 2.43 | 2.39 |
| miR-9 + 218 + 375 | 5.23 | 6.48 |
| 3 miRs + anti-miR-221 | 8.6 | 7.9 |
| 3 miRs + anti-miR-373 | 9.2 | 8.45 |

Example 9

Combination RTVP-1 Silencing and miRNA Expression to Differentiate MSCs to NSCs Already having shown that RTVP-1 silencing alone was sufficient to drive MSC trans-differentiation to NSCs as measured by nestin mRNA expression, it was next investigated whether the silencing in combination with miR expression could enhance the levels of nestin expressed. MSCs were contacted with a control siRNA, RTVP-1 silencing agent alone (an siRNA against RTVP-1, with the sequence AAGACTGCGTTCGAATCCATA (SEQ ID NO: 481), or the agent in combination with miR-218, miR-504, miR-9, miR-125 or anti-miR-31 (FIG. 12). As compared to the siRNA control cells, RTVP-1 knockdown alone increased nestin mRNA expression by 3.9-fold. Addition of any of the above enumerated miRs or anti-miRs further increased nestin expression; and the addition of miR-504 or miR-9 more than doubled nestin expression. Knockdown of miR-31 in combination with RTVP-1 silencing also had a very strong synergistic effect, although not quite a doubling as compared to RTVP-1 silencing alone.

Example 10

Use of Motor Neuron-Differentiated MSCs to Treat ALS

SOD1G93A mice were used as a model for amyotrophic lateral sclerosis (ALS). Placenta-derived MSCs were trans-differentiated to motor neurons as described in Example 8 (transfection of miR-9, miR-218 and miR-375) and these cells were administered intrathecally (5×10^5-1×106 cells) to pre-symptomatic mice (90 days old). Cells were subsequently re-administered 1 week later. SOD1G93A mice were also administered placenta-derived MSCs that had been transfected with control miRs and well as administered PBS as a control. The mean survival of eight control mice who received only PBS was 135.1. The mean survival of eight control mice who received control MSCs was 132.5 days. Administration of motor neuron differentiated MSCs resulted in a statistically significant increase in the mean survival of the eight test mice, as these mice survived, on average, 160.4 days.

Example 11

Use of Motor Neuron-Differentiated MSCs to Treat Spinal Cord Injury

The ability of the motor neuron-differentiated MSCs to treat nerve, and specifically spinal cord, injury was investigated. Wild-type rats underwent spinal cord perfusion injury by blocking the abdominal aorta below the left renal artery for 15 minutes. The injured rats were then treated with PBS or motor neuron-differentiated MSCs (1×10^7 cells) injected at the L5-L6 segment of the spine. Four days later lower limb movement in the rats was evaluated using the Basso, Beattie and Bresnahan (BBB) locomotor scale method. Uninjured rats were also evaluated as a control. The BBB scale is a well-established and discriminating method for measuring behavioral outcome and for evaluating treatments after spinal cord injury. The scale ranges from zero to 21, with a higher score indicating superior movement. The scoring can be summarized by the following breakdown:

0-7: Isolated joint movements with little or no hindlimb movement.

8-13: Intervals of uncoordinated stepping.

14-21: Forelimb and hindlimb coordination.

As can be seen in FIG. 13, uninjured mice had a nearly perfect score of 20.6 on the BBB scale, whereas control injured mice treated with only PBS scored in the lowest category with an average score of 4.2. Mice treated with motor neuron-transdifferentiated MSCs showed a strong improvement in locomotion, with an average score of 11.8, which is the upper half of the middle category, and were capable of uncoordinated stepping.

Example 12

Use of NSC-Differentiated MSCs to Glioma

The ability of MSC transdifferentiated to NSCs by silencing of RTVP-1 to treat gliomas was investigated. Glioma stem cell (GSC)-derived xenografts were grown in immune-compromised mice, and the mice were treated with either RTVP-1 silenced MSCs transdifferentiated to NSCs (as described in Example 9), or MSCs expressing control molecules. The transdifferentiated MSCs decreased tumor growth by 59.7% as compared to the control MSC where the decrease was only 41.1%. Further, glioma cells highly express RTVP-1, indeed its other name is glioma pathogenesis-related protein-GLIPR1, but normal healthy brain tissue does not. After dissection of the GSC xenografts it was found that RTVP-1 silenced MSCs greatly reduced RTVP-1 levels in the tumor. Isolated exosomes from the transdifferentiated MSCs contained high levels of the siRNA, suggesting that the decrease in RTVP-1 in the tumor was likely a result of MSC-derived exosome transfer of the siRNA to tumor cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method of promoting mesenchymal stem cell (MSC) differentiation toward a motor neuron cell, the method comprising:

(i) culturing a MSC in a medium supporting motor neuron cell growth and differentiation;

(ii) introducing into said MSC the following exogenous microRNAs (miRs): miR-9, miR-218 and miR-375; and (iii) confirming increased expression of at least one motor neuron marker selected from the group consisting of Islet1 and HB9 by detecting expression of said marker in said MSC, thereby promoting differentiation of the MSC into the motor neuron cell.

2. The method of claim 1, wherein said introducing comprises any one of:

(i) transfecting said MSCs with an expression vector which comprises a polynucleotide sequence which encodes a pre-miRNA of said miR; or (ii) transfecting said MSCs with an expression vector which comprises a polynucleotide sequence which encodes said miR.

3. The method of claim 1, further comprising introducing into said MSC a miR-221 antagomir or a miR-373 antagomir, before said confirming.

4. A method of promoting mesenchymal stem cell (MSC) differentiation toward a motor neuron cell, the method comprising:

(i) culturing a MSC in a medium supporting motor neuron cell growth and differentiation;

(ii) introducing into said MSC the following exogenous microRNAs (miRs): miR-9, miR-218 and miR-375; and (iii) confirming expression of at least one motor neuron marker selected from the group consisting of Islet1 and HB9, wherein said expressing results in at least 50% of the MSCs expressing said motor neuron marker, thereby promoting differentiation of the MSC into the motor neuron cell.

5. The method of claim 4, wherein said introducing comprises any one of:

(i) transfecting said MSCs with an expression vector which comprises a polynucleotide sequence which encodes a pre-miRNA of said miR; or (ii) transfecting said MSCs with an expression vector which comprises a polynucleotide sequence which encodes said miR.

6. The method of claim 4, further comprising introducing into said MSC a miR-221 antagomir or a miR-373 antagomir, before said confirming.

* * * * *

SEQUENCE LISTING

```
<160> NUMBER OF SEQ ID NOS: 481

<210> SEQ ID NO 1
<211> LENGTH: 22
<212> TYPE: RNA
<213> ORGANISM: Homo sapiens

<400> SEQUENCE: 1

ugagguagua gguuguauag uu                                              22


<210> SEQ ID NO 2
<211> LENGTH: 22
<212> TYPE: RNA
<213> ORGANISM: Homo sapiens

<400> SEQUENCE: 2

ugagguagua gguugugugg uu                                              22


<210> SEQ ID NO 3
<211> LENGTH: 22
<212> TYPE: RNA
<213> ORGANISM: Homo sapiens

<400> SEQUENCE: 3

ugagguagua gguuguaugg uu                                              22


<210> SEQ ID NO 4
<211> LENGTH: 22
<212> TYPE: RNA
<213> ORGANISM: Homo sapiens
```

<400> SEQUENCE: 4
agagguagua gguugcauag uu 22

<210> SEQ ID NO 5
<211> LENGTH: 22
<212> TYPE: RNA
<213> ORGANISM: Homo sapiens

<400> SEQUENCE: 5
ugagguagga gguuguauag uu 22

<210> SEQ ID NO 6
<211> LENGTH: 22
<212> TYPE: RNA
<213> ORGANISM: Homo sapiens

<400> SEQUENCE: 6
ugagguagua gauuguauag uu 22

<210> SEQ ID NO 7
<211> LENGTH: 22
<212> TYPE: RNA
<213> ORGANISM: Homo sapiens

<400> SEQUENCE: 7
ugagguagua guuuguacag uu 22

<210> SEQ ID NO 8
<211> LENGTH: 22
<212> TYPE: RNA
<213> ORGANISM: Homo sapiens

<400> SEQUENCE: 8
ugagguagua guuugugcug uu 22

<210> SEQ ID NO 9
<211> LENGTH: 23
<212> TYPE: RNA
<213> ORGANISM: Homo sapiens

<400> SEQUENCE: 9
aaaagugcuu acagugcagg uag 23

<210> SEQ ID NO 10
<211> LENGTH: 21
<212> TYPE: RNA
<213> ORGANISM: Homo sapiens

<400> SEQUENCE: 10
uaaagugcug acagugcaga u 21

<210> SEQ ID NO 11
<211> LENGTH: 22
<212> TYPE: RNA
<213> ORGANISM: Homo sapiens

<400> SEQUENCE: 11
ugugagguug gcauuguugu cu 22

<210> SEQ ID NO 12
<211> LENGTH: 17
<212> TYPE: RNA

<213> ORGANISM: Homo sapiens

<400> SEQUENCE: 12
uucaaguaau ucaggug 17

<210> SEQ ID NO 13
<211> LENGTH: 22
<212> TYPE: RNA
<213> ORGANISM: Homo sapiens

<400> SEQUENCE: 13
ggugcagugc ugcaucucug gu 22

<210> SEQ ID NO 14
<211> LENGTH: 20
<212> TYPE: RNA
<213> ORGANISM: Homo sapiens

<400> SEQUENCE: 14
uacaguauag augauguacu 20

<210> SEQ ID NO 15
<211> LENGTH: 23
<212> TYPE: RNA
<213> ORGANISM: Homo sapiens

<400> SEQUENCE: 15
guccaguuuu cccaggaauc ccu 23

<210> SEQ ID NO 16
<211> LENGTH: 23
<212> TYPE: RNA
<213> ORGANISM: Homo sapiens

<400> SEQUENCE: 16
caaagugcuu acagugcagg uag 23

<210> SEQ ID NO 17
<211> LENGTH: 23
<212> TYPE: RNA
<213> ORGANISM: Homo sapiens

<400> SEQUENCE: 17
aacauucaac gcugucggug agu 23

<210> SEQ ID NO 18
<211> LENGTH: 23
<212> TYPE: RNA
<213> ORGANISM: Homo sapiens

<400> SEQUENCE: 18
aacauucaac gcugucggug agu 23

<210> SEQ ID NO 19
<211> LENGTH: 23
<212> TYPE: RNA
<213> ORGANISM: Homo sapiens

<400> SEQUENCE: 19
aacauucauu gcugucggug ggu 23

<210> SEQ ID NO 20
<211> LENGTH: 23

<212> TYPE: RNA
<213> ORGANISM: Homo sapiens

<400> SEQUENCE: 20
aacauucauu gcugucggug ggu                                              23

<210> SEQ ID NO 21
<211> LENGTH: 22
<212> TYPE: RNA
<213> ORGANISM: Homo sapiens

<400> SEQUENCE: 21
aacauucaac cugucgguga gu                                               22

<210> SEQ ID NO 22
<211> LENGTH: 23
<212> TYPE: RNA
<213> ORGANISM: Homo sapiens

<400> SEQUENCE: 22
aacauucauu guugucggug ggu                                              23

<210> SEQ ID NO 23
<211> LENGTH: 22
<212> TYPE: RNA
<213> ORGANISM: Homo sapiens

<400> SEQUENCE: 23
acaguagucu gcacauuggu ua                                               22

<210> SEQ ID NO 24
<211> LENGTH: 22
<212> TYPE: RNA
<213> ORGANISM: Homo sapiens

<400> SEQUENCE: 24
acaguagucu gcacauuggu ua                                               22

<210> SEQ ID NO 25
<211> LENGTH: 20
<212> TYPE: RNA
<213> ORGANISM: Homo sapiens

<400> SEQUENCE: 25
agagguauag ggcaugggaa                                                  20

<210> SEQ ID NO 26
<211> LENGTH: 23
<212> TYPE: RNA
<213> ORGANISM: Homo sapiens

<400> SEQUENCE: 26
uaaagugcuu auagugcagg uag                                              23

<210> SEQ ID NO 27
<211> LENGTH: 23
<212> TYPE: RNA
<213> ORGANISM: Homo sapiens

<400> SEQUENCE: 27
caaagugcuc auagugcagg uag                                              23

<210> SEQ ID NO 28

<211> LENGTH: 21
<212> TYPE: RNA
<213> ORGANISM: Homo sapiens

<400> SEQUENCE: 28
auuugugcuu ggcucuguca c 21

<210> SEQ ID NO 29
<211> LENGTH: 22
<212> TYPE: RNA
<213> ORGANISM: Homo sapiens

<400> SEQUENCE: 29
cauugcacuu gucucggucu ga 22

<210> SEQ ID NO 30
<211> LENGTH: 22
<212> TYPE: RNA
<213> ORGANISM: Homo sapiens

<400> SEQUENCE: 30
uucaaguaau ccaggauagg cu 22

<210> SEQ ID NO 31
<211> LENGTH: 22
<212> TYPE: RNA
<213> ORGANISM: Homo sapiens

<400> SEQUENCE: 31
uucaaguaau ccaggauagg cu 22

<210> SEQ ID NO 32
<211> LENGTH: 21
<212> TYPE: RNA
<213> ORGANISM: Homo sapiens

<400> SEQUENCE: 32
uucaaguaau ucaggauagg u 21

<210> SEQ ID NO 33
<211> LENGTH: 22
<212> TYPE: RNA
<213> ORGANISM: Homo sapiens

<400> SEQUENCE: 33
uagcaccauc ugaaaucggu ua 22

<210> SEQ ID NO 34
<211> LENGTH: 23
<212> TYPE: RNA
<213> ORGANISM: Homo sapiens

<400> SEQUENCE: 34
uagcaccauu ugaaaucagu guu 23

<210> SEQ ID NO 35
<211> LENGTH: 22
<212> TYPE: RNA
<213> ORGANISM: Homo sapiens

<400> SEQUENCE: 35
uagcaccauu ugaaaucggu ua 22

<210> SEQ ID NO 36
<211> LENGTH: 22
<212> TYPE: RNA
<213> ORGANISM: Homo sapiens

<400> SEQUENCE: 36
gcaguagugu agagauuggu uu 22

<210> SEQ ID NO 37
<211> LENGTH: 23
<212> TYPE: RNA
<213> ORGANISM: Homo sapiens

<400> SEQUENCE: 37
uguguacaca cgugccaggc gcu 23

<210> SEQ ID NO 38
<211> LENGTH: 22
<212> TYPE: RNA
<213> ORGANISM: Homo sapiens

<400> SEQUENCE: 38
uauugcacau uacuaaguug ca 22

<210> SEQ ID NO 39
<211> LENGTH: 20
<212> TYPE: RNA
<213> ORGANISM: Homo sapiens

<400> SEQUENCE: 39
ccucugggcc cuuccuccag 20

<210> SEQ ID NO 40
<211> LENGTH: 23
<212> TYPE: RNA
<213> ORGANISM: Homo sapiens

<400> SEQUENCE: 40
gcaaagcaca cggccugcag aga 23

<210> SEQ ID NO 41
<211> LENGTH: 22
<212> TYPE: RNA
<213> ORGANISM: Homo sapiens

<400> SEQUENCE: 41
aauugcacgg uauccaucug ua 22

<210> SEQ ID NO 42
<211> LENGTH: 21
<212> TYPE: RNA
<213> ORGANISM: Homo sapiens

<400> SEQUENCE: 42
ugaguguugu cuacgagggc a 21

<210> SEQ ID NO 43
<211> LENGTH: 24
<212> TYPE: RNA
<213> ORGANISM: Homo sapiens

<400> SEQUENCE: 43
gaaaaugaug aguagugacu gaug 24

<210> SEQ ID NO 44
<211> LENGTH: 22
<212> TYPE: RNA
<213> ORGANISM: Homo sapiens

<400> SEQUENCE: 44
aauugcacuu uagcaauggu ga 22

<210> SEQ ID NO 45
<211> LENGTH: 23
<212> TYPE: RNA
<213> ORGANISM: Homo sapiens

<400> SEQUENCE: 45
aaagugcugc gacauuugag cgu 23

<210> SEQ ID NO 46
<211> LENGTH: 23
<212> TYPE: RNA
<213> ORGANISM: Homo sapiens

<400> SEQUENCE: 46
gaagugcuuc gauuuugggg ugu 23

<210> SEQ ID NO 47
<211> LENGTH: 22
<212> TYPE: RNA
<213> ORGANISM: Homo sapiens

<400> SEQUENCE: 47
cagguagaua uuugauaggc au 22

<210> SEQ ID NO 48
<211> LENGTH: 17
<212> TYPE: RNA
<213> ORGANISM: Homo sapiens

<400> SEQUENCE: 48
gacauucaga cuaccug 17

<210> SEQ ID NO 49
<211> LENGTH: 16
<212> TYPE: RNA
<213> ORGANISM: Homo sapiens

<400> SEQUENCE: 49
cucuccuccc ggcuuc 16

<210> SEQ ID NO 50
<211> LENGTH: 19
<212> TYPE: RNA
<213> ORGANISM: Homo sapiens

<400> SEQUENCE: 50
agagguaggu guggaagaa 19

<210> SEQ ID NO 51
<211> LENGTH: 22
<212> TYPE: RNA
<213> ORGANISM: Homo sapiens

<400> SEQUENCE: 51
cucaaguagu cugaccaggg ga 22

<210> SEQ ID NO 52
<211> LENGTH: 17
<212> TYPE: RNA
<213> ORGANISM: Homo sapiens

<400> SEQUENCE: 52
ugagguagua guuucuu 17

<210> SEQ ID NO 53
<211> LENGTH: 23
<212> TYPE: RNA
<213> ORGANISM: Homo sapiens

<400> SEQUENCE: 53
gugagugugg auccuggagg aau 23

<210> SEQ ID NO 54
<211> LENGTH: 21
<212> TYPE: RNA
<213> ORGANISM: Homo sapiens

<400> SEQUENCE: 54
guaccuucug guucagcuag u 21

<210> SEQ ID NO 55
<211> LENGTH: 23
<212> TYPE: RNA
<213> ORGANISM: Homo sapiens

<400> SEQUENCE: 55
ucuguauucu ccuuugccug cag 23

<210> SEQ ID NO 56
<211> LENGTH: 18
<212> TYPE: RNA
<213> ORGANISM: Homo sapiens

<400> SEQUENCE: 56
ugagaugaca cuguagcu 18

<210> SEQ ID NO 57
<211> LENGTH: 22
<212> TYPE: RNA
<213> ORGANISM: Homo sapiens

<400> SEQUENCE: 57
caaagugccu cccuuuagag ug 22

<210> SEQ ID NO 58
<211> LENGTH: 22
<212> TYPE: RNA
<213> ORGANISM: Homo sapiens

<400> SEQUENCE: 58
aaagugcuuc ccuuuggacu gu 22

<210> SEQ ID NO 59
<211> LENGTH: 21
<212> TYPE: RNA
<213> ORGANISM: Homo sapiens

<400> SEQUENCE: 59
aaagugcuuc cuuuuagagg g 21

<210> SEQ ID NO 60
<211> LENGTH: 22
<212> TYPE: RNA
<213> ORGANISM: Homo sapiens

<400> SEQUENCE: 60
aaagugcuuc cuuuuagagg gu 22

<210> SEQ ID NO 61
<211> LENGTH: 22
<212> TYPE: RNA
<213> ORGANISM: Homo sapiens

<400> SEQUENCE: 61
aaagugcuuc ucuuuggugg gu 22

<210> SEQ ID NO 62
<211> LENGTH: 20
<212> TYPE: RNA
<213> ORGANISM: Homo sapiens

<400> SEQUENCE: 62
cuacaaaggg aagcccuuuc 20

<210> SEQ ID NO 63
<211> LENGTH: 21
<212> TYPE: RNA
<213> ORGANISM: Homo sapiens

<400> SEQUENCE: 63
aaagugcuuc cuuuuugagg g 21

<210> SEQ ID NO 64
<211> LENGTH: 22
<212> TYPE: RNA
<213> ORGANISM: Homo sapiens

<400> SEQUENCE: 64
cuacaaaggg aagcacuuuc uc 22

<210> SEQ ID NO 65
<211> LENGTH: 22
<212> TYPE: RNA
<213> ORGANISM: Homo sapiens

<400> SEQUENCE: 65
agacacauuu ggagagggac cc 22

<210> SEQ ID NO 66
<211> LENGTH: 21
<212> TYPE: RNA
<213> ORGANISM: Homo sapiens

<400> SEQUENCE: 66
aauauuauac agucaaccuc u 21

<210> SEQ ID NO 67
<211> LENGTH: 23
<212> TYPE: RNA
<213> ORGANISM: Homo sapiens

<400> SEQUENCE: 67
ugcaccaugg uugucugagc aug 23

<210> SEQ ID NO 68
<211> LENGTH: 22
<212> TYPE: RNA
<213> ORGANISM: Homo sapiens

<400> SEQUENCE: 68
uauugcacuu gucccggccu gu 22

<210> SEQ ID NO 69
<211> LENGTH: 22
<212> TYPE: RNA
<213> ORGANISM: Homo sapiens

<400> SEQUENCE: 69
uauugcacuu gucccggccu gu 22

<210> SEQ ID NO 70
<211> LENGTH: 22
<212> TYPE: RNA
<213> ORGANISM: Homo sapiens

<400> SEQUENCE: 70
uauugcacuc gucccggccu cc 22

<210> SEQ ID NO 71
<211> LENGTH: 23
<212> TYPE: RNA
<213> ORGANISM: Homo sapiens

<400> SEQUENCE: 71
caaagugcug uucgugcagg uag 23

<210> SEQ ID NO 72
<211> LENGTH: 22
<212> TYPE: RNA
<213> ORGANISM: Homo sapiens

<400> SEQUENCE: 72
ugagguagua aguuguauug uu 22

<210> SEQ ID NO 73
<211> LENGTH: 80
<212> TYPE: RNA
<213> ORGANISM: Homo sapiens

<400> SEQUENCE: 73
ugggaugagg uaguagguug uauaguuuua gggucacacc caccacuggg agauaacuau 60
acaaucuacu gucuuuccua 80

<210> SEQ ID NO 74
<211> LENGTH: 72
<212> TYPE: RNA
<213> ORGANISM: Homo sapiens

<400> SEQUENCE: 74
agguugaggu aguagguugu auaguuuaga auuacaucaa gggagauaac uguacagccu 60
ccuagcuuuc cu 72

<210> SEQ ID NO 75

-continued

<211> LENGTH: 74
<212> TYPE: RNA
<213> ORGANISM: Homo sapiens

<400> SEQUENCE: 75
gggugaggua guagguugua uaguuugggg cucugcccug cuaugggaua acuauacaau 60
cuacugucuu uccu 74

<210> SEQ ID NO 76
<211> LENGTH: 83
<212> TYPE: RNA
<213> ORGANISM: Homo sapiens

<400> SEQUENCE: 76
cggggugagg uaguagguug ugugguuuca gggcagugau guugccccuc ggaagauaac 60
uauacaaccu acugccuucc cug 83

<210> SEQ ID NO 77
<211> LENGTH: 84
<212> TYPE: RNA
<213> ORGANISM: Homo sapiens

<400> SEQUENCE: 77
gcauccgggu ugagguagua gguuguaugg uuuagaguua cacccuggga guuaacugua 60
caaccuucua gcuuuccuug gagc 84

<210> SEQ ID NO 78
<211> LENGTH: 87
<212> TYPE: RNA
<213> ORGANISM: Homo sapiens

<400> SEQUENCE: 78
ccuaggaaga gguaguaggu ugcauaguuu uagggcaggg auuuugccca caaggaggua 60
acuauacgac cugcugccuu ucuuagg 87

<210> SEQ ID NO 79
<211> LENGTH: 79
<212> TYPE: RNA
<213> ORGANISM: Homo sapiens

<400> SEQUENCE: 79
cccgggcuga gguaggaggu uguauaguug aggaggacac ccaaggagau cacuauacgg 60
ccuccuagcu uuccccagg 79

<210> SEQ ID NO 80
<211> LENGTH: 87
<212> TYPE: RNA
<213> ORGANISM: Homo sapiens

<400> SEQUENCE: 80
ucagagugag guaguagauu guauaguugu gggguaguga uuuuacccug uucaggagau 60
aacuauacaa ucuauugccu ucccuga 87

<210> SEQ ID NO 81
<211> LENGTH: 84
<212> TYPE: RNA
<213> ORGANISM: Homo sapiens

<400> SEQUENCE: 81
aggcugaggu aguaguuugu acaguuugag ggucuaugau accacccggu acaggagaua 60

-continued acuguacagg ccacugccuu gcca 84

<210> SEQ ID NO 82
<211> LENGTH: 84
<212> TYPE: RNA
<213> ORGANISM: Homo sapiens

<400> SEQUENCE: 82
cuggcugagg uaguaguuug ugcuguuggu cggguuguga cauugcccgc uguggagaua 60
acugcgcaag cuacugccuu gcua 84

<210> SEQ ID NO 83
<211> LENGTH: 81
<212> TYPE: RNA
<213> ORGANISM: Homo sapiens

<400> SEQUENCE: 83
ccuuggccau guaaaagugc uuacagugca gguagcuuuu ugagaucuac ugcaauguaa 60
gcacuucuua cauuaccaug g 81

<210> SEQ ID NO 84
<211> LENGTH: 82
<212> TYPE: RNA
<213> ORGANISM: Homo sapiens

<400> SEQUENCE: 84
ccugccgggg cuaaagugcu gacagugcag auaguggucc ucuccgugcu accgcacugu 60
ggguacuugc ugcuccagca gg 82

<210> SEQ ID NO 85
<211> LENGTH: 142
<212> TYPE: RNA
<213> ORGANISM: Homo sapiens

<400> SEQUENCE: 85
caccuaaugu gugccaagau cuguucauuu augaucucac cgaguccugu gagguuggca 60
uuguugucug gcauugucug auauacaaca gugccaaccu cacaggacuc agugagguga 120
aacugaggau uaggaaggug ua 142

<210> SEQ ID NO 86
<211> LENGTH: 77
<212> TYPE: RNA
<213> ORGANISM: Homo sapiens

<400> SEQUENCE: 86
uguuuaucuc uaggguugau cuauuagaau uacuuaucug agccaaagua auucaaguaa 60
uucaggugua gugaaac 77

<210> SEQ ID NO 87
<211> LENGTH: 106
<212> TYPE: RNA
<213> ORGANISM: Homo sapiens

<400> SEQUENCE: 87
gcgcagcgcc cugucuccca gccugaggug cagugcugca ucucugguca guugggaguc 60
ugagaugaag cacuguagcu caggaagaga gaaguuguuc ugcagc 106

<210> SEQ ID NO 88

<211> LENGTH: 86
<212> TYPE: RNA
<213> ORGANISM: Homo sapiens

<400> SEQUENCE: 88
uggggcccug gcugggauau caucauauac uguaaguuug cgaugagaca cuacaguaua 60
gaugauguac uaguccgggc accccc 86

<210> SEQ ID NO 89
<211> LENGTH: 88
<212> TYPE: RNA
<213> ORGANISM: Homo sapiens

<400> SEQUENCE: 89
caccuuguuc ucacggucca guuuucccag gaaucccuua gaugcuaaga uggggauucc 60
uggaaauacu guucuugagg ucaugguu 88

<210> SEQ ID NO 90
<211> LENGTH: 84
<212> TYPE: RNA
<213> ORGANISM: Homo sapiens

<400> SEQUENCE: 90
gucagaauaa ugucaaagug cuuacagugc agguagugau augugcaucu acugcaguga 60
aggcacuugu agcauuaugg ugac 84

<210> SEQ ID NO 91
<211> LENGTH: 110
<212> TYPE: RNA
<213> ORGANISM: Homo sapiens

<400> SEQUENCE: 91
ugaguuuuga gguugcuuca gugaacauuc aacgcugucg gugaguuugg aauuaaaauc 60
aaaaccaucg accguugauu guacccuaug gcuaaccauc aucuacucca 110

<210> SEQ ID NO 92
<211> LENGTH: 110
<212> TYPE: RNA
<213> ORGANISM: Homo sapiens

<400> SEQUENCE: 92
agaagggcua ucaggccagc cuucagagga cuccaaggaa cauucaacgc ugucggugag 60
uuugggauuu gaaaaaacca cugaccguug acuguaccuu ggggguccuua 110

<210> SEQ ID NO 93
<211> LENGTH: 110
<212> TYPE: RNA
<213> ORGANISM: Homo sapiens

<400> SEQUENCE: 93
ccugugcaga gauuauuuuu uaaaagguca caaucaacau ucauugcugu cgguggguug 60
aacugugugg acaagcucac ugaacaauga augcaacugu ggccccgcuu 110

<210> SEQ ID NO 94
<211> LENGTH: 89
<212> TYPE: RNA
<213> ORGANISM: Homo sapiens

<400> SEQUENCE: 94
cugauggcug cacucaacau ucauugcugu cgguggguuu gagucugaau caacucacug 60
aucaaugaau gcaaacugcg gaccaaaca 89

<210> SEQ ID NO 95
<211> LENGTH: 110
<212> TYPE: RNA
<213> ORGANISM: Homo sapiens

<400> SEQUENCE: 95
cggaaaauuu gccaaggguu ugggggaaca uucaaccugu cggugaguuu gggcagcuca 60
ggcaaaccau cgaccguuga guggacccug aggccuggaa uugccauccu 110

<210> SEQ ID NO 96
<211> LENGTH: 137
<212> TYPE: RNA
<213> ORGANISM: Homo sapiens

<400> SEQUENCE: 96
guccccuccc cuaggccaca gccgagguca caaucaacau ucauuguugu cgguggguug 60
ugaggacuga ggccagaccc accgggggau gaaugucacu guggcugggc cagacacggc 120
uuaaggggaa uggggac 137

<210> SEQ ID NO 97
<211> LENGTH: 71
<212> TYPE: RNA
<213> ORGANISM: Homo sapiens

<400> SEQUENCE: 97
gccaacccag uguucagacu accuguucag gaggcucuca auguguacag uagucugcac 60
auugguuagg c 71

<210> SEQ ID NO 98
<211> LENGTH: 110
<212> TYPE: RNA
<213> ORGANISM: Homo sapiens

<400> SEQUENCE: 98
ccagaggaca ccuccacucc gucuacccag uguuuagacu aucuguucag gacucccaaa 60
uuguacagua gucugcacau ugguuaggcu gggcuggguu agacccucgg 110

<210> SEQ ID NO 99
<211> LENGTH: 110
<212> TYPE: RNA
<213> ORGANISM: Homo sapiens

<400> SEQUENCE: 99
cgccucagag ccgcccgccg uuccuuuuuc cuaugcauau acuucuuuga ggaucuggcc 60
uaaagaggua uagggcaugg gaaaacgggg cggucggguc cuccccagcg 110

<210> SEQ ID NO 100
<211> LENGTH: 71
<212> TYPE: RNA
<213> ORGANISM: Homo sapiens

<400> SEQUENCE: 100
guagcacuaa agugcuuaua gugcagguag uguuuaguua ucuacugcau uaugagcacu 60
uaaaguacug c 71

<210> SEQ ID NO 101

<211> LENGTH: 69
<212> TYPE: RNA
<213> ORGANISM: Homo sapiens

<400> SEQUENCE: 101
aguaccaaag ugcucauagu gcagguaguu uuggcaugac ucuacuguag uaugggcacu 60
uccaguacu 69

<210> SEQ ID NO 102
<211> LENGTH: 91
<212> TYPE: RNA
<213> ORGANISM: Homo sapiens

<400> SEQUENCE: 102
uuuucaaagc aaugugugac agguacaggg acaaaucccg uuaauaagua agaggauuug 60
ugcuuggcuc ugucacaugc cacuuugaaa a 91

<210> SEQ ID NO 103
<211> LENGTH: 84
<212> TYPE: RNA
<213> ORGANISM: Homo sapiens

<400> SEQUENCE: 103
ggccaguguu gagaggcgga gacuugggca auugcuggac gcugcccugg gcauugcacu 60
ugucucgguc ugacagugcc ggcc 84

<210> SEQ ID NO 104
<211> LENGTH: 77
<212> TYPE: RNA
<213> ORGANISM: Homo sapiens

<400> SEQUENCE: 104
guggccucgu ucaaguaauc caggauaggc ugugcagguc ccaaugggcc uauucuuggu 60
uacuugcacg gggacgc 77

<210> SEQ ID NO 105
<211> LENGTH: 84
<212> TYPE: RNA
<213> ORGANISM: Homo sapiens

<400> SEQUENCE: 105
ggcuguggcu ggauucaagu aauccaggau aggcuguuuc caucugugag gccuauucuu 60
gauuacuugu uucuggaggc agcu 84

<210> SEQ ID NO 106
<211> LENGTH: 77
<212> TYPE: RNA
<213> ORGANISM: Homo sapiens

<400> SEQUENCE: 106
ccgggaccca guucaaguaa uucaggauag guugugugcu guccagccug uucuccauua 60
cuuggcucgg ggaccgg 77

<210> SEQ ID NO 107
<211> LENGTH: 64
<212> TYPE: RNA
<213> ORGANISM: Homo sapiens

<400> SEQUENCE: 107
augacugauu ucuuuuggug uucagaguca auauaauuuu cuagcaccau cugaaaucgg 60
uuau 64

<210> SEQ ID NO 108
<211> LENGTH: 81
<212> TYPE: RNA
<213> ORGANISM: Homo sapiens

<400> SEQUENCE: 108
cuucaggaag cugguuucau augguguuu agauuuaaau agugauuguc uagcaccauu 60
ugaaaucagu guucuugggg g 81

<210> SEQ ID NO 109
<211> LENGTH: 81
<212> TYPE: RNA
<213> ORGANISM: Homo sapiens

<400> SEQUENCE: 109
cuucuggaag cugguuucac augguggcuu agauuuuucc aucuuuguau cuagcaccau 60
uugaaaucag uguuuuagga g 81

<210> SEQ ID NO 110
<211> LENGTH: 88
<212> TYPE: RNA
<213> ORGANISM: Homo sapiens

<400> SEQUENCE: 110
aucucuuaca caggcugacc gauuucuccu ggguguucaga gucuguuuuu gucuagcacc 60
auuugaaauc gguuaugaug uaggggga 88

<210> SEQ ID NO 111
<211> LENGTH: 76
<212> TYPE: RNA
<213> ORGANISM: Homo sapiens

<400> SEQUENCE: 111
guacuugggc aguaguguag agauugguuu gccuguuaau gaauucaaac uaaucucuac 60
acugcugccc aagagc 76

<210> SEQ ID NO 112
<211> LENGTH: 82
<212> TYPE: RNA
<213> ORGANISM: Homo sapiens

<400> SEQUENCE: 112
ccacgugcca uguguacaca cgugccaggc gcugucuuga gacauucgcg cagugcacgg 60
cacuggggac acguggcacu gg 82

<210> SEQ ID NO 113
<211> LENGTH: 70
<212> TYPE: RNA
<213> ORGANISM: Homo sapiens

<400> SEQUENCE: 113
ggagauauug cacauuacua aguugcaugu ugucacggcc ucaaugcaau uuagugugug 60
ugauauuuuc 70

<210> SEQ ID NO 114
<211> LENGTH: 95
<212> TYPE: RNA

-continued

<213> ORGANISM: Homo sapiens

<400> SEQUENCE: 114
cucaucuguc uguugggcug gaggcagggc cuuugugaag gcggguggug cucagaucgc 60
cucugggccc uuccuccagc cccgaggcgg auuca 95

<210> SEQ ID NO 115
<211> LENGTH: 94
<212> TYPE: RNA
<213> ORGANISM: Homo sapiens

<400> SEQUENCE: 115
cuuuggcgau cacugccucu cugggccugu gucuuaggcu cugcaagauc aaccgagcaa 60
agcacacggc cugcagagag gcagcgcucu gccc 94

<210> SEQ ID NO 116
<211> LENGTH: 75
<212> TYPE: RNA
<213> ORGANISM: Homo sapiens

<400> SEQUENCE: 116
uguugucggg uggaucacga ugcaauuuug augaguauca uaggagaaaa auugcacggu 60
auccaucugu aaacc 75

<210> SEQ ID NO 117
<211> LENGTH: 99
<212> TYPE: RNA
<213> ORGANISM: Homo sapiens

<400> SEQUENCE: 117
ucuacaagca gauacaagga ugcccuugua cacaacacac gugcugcuug uauagacaug 60
aguguugucu acgagggcau ccuugugucu gugugugug 99

<210> SEQ ID NO 118
<211> LENGTH: 95
<212> TYPE: RNA
<213> ORGANISM: Homo sapiens

<400> SEQUENCE: 118
uguguuuucc ucaacgcuca caguuacacu ucuuacucuc aauccauuca uauugaaaau 60
gaugaguagu gacugaugaa gcacaaauca gccaa 95

<210> SEQ ID NO 119
<211> LENGTH: 68
<212> TYPE: RNA
<213> ORGANISM: Homo sapiens

<400> SEQUENCE: 119
ccauuacugu ugcuaauaug caacucuguu gaauauaaau uggaauugca cuuuagcaau 60
ggugaugg 68

<210> SEQ ID NO 120
<211> LENGTH: 67
<212> TYPE: RNA
<213> ORGANISM: Homo sapiens

<400> SEQUENCE: 120
gugggccuca aauguggagc acuauucuga uguccaagug gaaagugcug cgacauuuga 60
gcgucac 67

<210> SEQ ID NO 121
<211> LENGTH: 69
<212> TYPE: RNA
<213> ORGANISM: Homo sapiens

<400> SEQUENCE: 121
gggauacuca aaaugggggc gcuuuccuuu uugucuguac ugggaagugc uucgauuuug 60 gggugucce 69

<210> SEQ ID NO 122
<211> LENGTH: 71
<212> TYPE: RNA
<213> ORGANISM: Homo sapiens

<400> SEQUENCE: 122
ugccaaugcc uaucacauau cugccugucc uaugacaaac auggcaggua gauauuugau 60
aggcauuggc a 71

<210> SEQ ID NO 123
<211> LENGTH: 54
<212> TYPE: RNA
<213> ORGANISM: Homo sapiens

<400> SEQUENCE: 123
gaaagcugca ggugcugaug uugggggac auucagacua ccugcagcag agcc 54

<210> SEQ ID NO 124
<211> LENGTH: 58
<212> TYPE: RNA
<213> ORGANISM: Homo sapiens

<400> SEQUENCE: 124
ugcucugugg agcugaggag cagauucucu cucucuccuc ccggcuucac cuccugag 58

<210> SEQ ID NO 125
<211> LENGTH: 75
<212> TYPE: RNA
<213> ORGANISM: Homo sapiens

<400> SEQUENCE: 125
gagcgcacag agguaggugu ggaagaaagu gaaacacuau uuuagguuuu aguuacacuc 60
ugcuguggug ugcug 75

<210> SEQ ID NO 126
<211> LENGTH: 70
<212> TYPE: RNA
<213> ORGANISM: Homo sapiens

<400> SEQUENCE: 126 caugugucce cuggcacgcu auuugagguu uacuauggaa ccucaaguag ucugaccagg 60
ggacacauga 70

<210> SEQ ID NO 127
<211> LENGTH: 76
<212> TYPE: RNA
<213> ORGANISM: Homo sapiens

<400> SEQUENCE: 127
caggagagaa aguacugccc agaagcuaaa guguagauca aacgcauaau ggcugaggua 60
guaguuucuu gaacuu 76

<210> SEQ ID NO 128
<211> LENGTH: 65
<212> TYPE: RNA
<213> ORGANISM: Homo sapiens

<400> SEQUENCE: 128
gcugcccuuc acucagagca ucuacaccca cuaccgguga guguggaucc uggaggaauc 60
guggc 65

<210> SEQ ID NO 129
<211> LENGTH: 89
<212> TYPE: RNA
<213> ORGANISM: Homo sapiens

<400> SEQUENCE: 129
acgcaaaaug aacugaacca ggagugagcu ucguguacau uaucuauuag aaaaugaagu 60
accuucuggu ucagcuaguc ccugugcgu 89

<210> SEQ ID NO 130
<211> LENGTH: 85
<212> TYPE: RNA
<213> ORGANISM: Homo sapiens

<400> SEQUENCE: 130
ucaggcaaag ggauauuuac agauacuuuu uaaaauuugu uugaguugag gcagauuaaa 60
uaucuguauu cuccuuugcc ugcag 85

<210> SEQ ID NO 131
<211> LENGTH: 58
<212> TYPE: RNA
<213> ORGANISM: Homo sapiens

<400> SEQUENCE: 131
gaguuauggg gucaucuauc cuucccuugg aaaaugaucu gagaugacac uguagcuc 58

<210> SEQ ID NO 132
<211> LENGTH: 88
<212> TYPE: RNA
<213> ORGANISM: Homo sapiens

<400> SEQUENCE: 132
ucccaugcug ugacccucca aagggaagcg cuuucuguuu guuuucucuu aaacaaagug 60
ccucccuuua gaguguuacc guuuggga 88

<210> SEQ ID NO 133
<211> LENGTH: 85
<212> TYPE: RNA
<213> ORGANISM: Homo sapiens

<400> SEQUENCE: 133
cucaggcugu gacccuccag agggaaguac uuucuguugu cugagagaaa agaaagugcu 60
ucccuuugga cuguuucggu uugag 85

<210> SEQ ID NO 134
<211> LENGTH: 61
<212> TYPE: RNA
<213> ORGANISM: Homo sapiens

<400> SEQUENCE: 134
cccucuacag ggaagcgcuu ucuguugucu gaaagaaaag aaagugcuuc cuuuuagagg 60
g 61

<210> SEQ ID NO 135
<211> LENGTH: 87
<212> TYPE: RNA
<213> ORGANISM: Homo sapiens

<400> SEQUENCE: 135
ucucaggcug ucguccucua gagggaagca cuuucuguug ucugaaagaa aagaaagugc 60
uuccuuuuag aggguuaccg uuugaga 87

<210> SEQ ID NO 136
<211> LENGTH: 87
<212> TYPE: RNA
<213> ORGANISM: Homo sapiens

<400> SEQUENCE: 136
ucucaagcug ugagucuaca aagggaagcc cuuucuguug ucuaaaagaa aagaaagugc 60
uucucuuugg uggguuacgg uuugaga 87

<210> SEQ ID NO 137
<211> LENGTH: 87
<212> TYPE: RNA
<213> ORGANISM: Homo sapiens

<400> SEQUENCE: 137
ucucaagcug ugagucuaca aagggaagcc cuuucuguug ucuaaaagaa aagaaagugc 60
uucucuuugg uggguuacgg uuugaga 87

<210> SEQ ID NO 138
<211> LENGTH: 87
<212> TYPE: RNA
<213> ORGANISM: Homo sapiens

<400> SEQUENCE: 138
ucuccugcug ugacccucaa gauggaagca guuucuguug ucugaaagga aagaaagugc 60
uuccuuuuug aggguuacug uuugaga 87

<210> SEQ ID NO 139
<211> LENGTH: 87
<212> TYPE: RNA
<213> ORGANISM: Homo sapiens

<400> SEQUENCE: 139
ucucaugcug ugacccuaca aagggaagca cuuucucuug uccaaaggaa aagaaggcgc 60
uucccuuugg aguguuacgg uuugaga 87

<210> SEQ ID NO 140
<211> LENGTH: 77
<212> TYPE: RNA
<213> ORGANISM: Homo sapiens

<400> SEQUENCE: 140
gaguugggag guucccucuc caaaugugucuugaucccccaccccaagac acauuuggag 60 agggacccuc ccaacuc 77

<210> SEQ ID NO 141

<211> LENGTH: 78
<212> TYPE: RNA
<213> ORGANISM: Homo sapiens

<400> SEQUENCE: 141
cugaaauagg uugccuguga gguguucacu uucuauauga ugaauauuau acagucaacc 60
ucuuuccgau aucgaauc 78

<210> SEQ ID NO 142
<211> LENGTH: 109
<212> TYPE: RNA
<213> ORGANISM: Homo sapiens

<400> SEQUENCE: 142
gcuuuuauau uguagguuuu ugcucaugca ccaugguugu cugagcaugc agcaugcuug 60
ucugcucaua ccccaugguu ucugagcagg aaccuucauu gucuacugc 109

<210> SEQ ID NO 143
<211> LENGTH: 78
<212> TYPE: RNA
<213> ORGANISM: Homo sapiens

<400> SEQUENCE: 143
cuuucuacac agguugggau cgguugcaau gcuguguuuc uguaugguau ugcacuuguc 60
ccggccuguu gaguuugg 78

<210> SEQ ID NO 144
<211> LENGTH: 75
<212> TYPE: RNA
<213> ORGANISM: Homo sapiens

<400> SEQUENCE: 144
ucaucccugg gugggggauuu guugcauuac uuguguucua uauaaaguau ugcacuuguc 60
ccggccugug gaaga 75

<210> SEQ ID NO 145
<211> LENGTH: 96
<212> TYPE: RNA
<213> ORGANISM: Homo sapiens

<400> SEQUENCE: 145
cgggccccgg gcgggcggga gggacgggac gcggugcagu guuguuuuuu cccccgccaa 60
uauugcacuc gucccggccu ccggcccccc cggccc 96

<210> SEQ ID NO 146
<211> LENGTH: 80
<212> TYPE: RNA
<213> ORGANISM: Homo sapiens

<400> SEQUENCE: 146
cugggggcuc caaagugcug uucgugcagg uagugugauu acccaaccua cugcugagcu 60
agcacuuccc gagcccccgg 80

<210> SEQ ID NO 147
<211> LENGTH: 119
<212> TYPE: RNA
<213> ORGANISM: Homo sapiens

<400> SEQUENCE: 147
aggauucugc ucaugccagg gugagguagu aaguuguauu guuguggggu agggauauua 60
ggccccaauu agaagauaac uauacaacuu acuacuuucc cuggugugug gcauauuca 119

<210> SEQ ID NO 148
<211> LENGTH: 21
<212> TYPE: RNA
<213> ORGANISM: Homo sapiens

<400> SEQUENCE: 148
aauauaacac agauggccug u 21

<210> SEQ ID NO 149
<211> LENGTH: 22
<212> TYPE: RNA
<213> ORGANISM: Homo sapiens

<400> SEQUENCE: 149
uauaaaauga gggcaguaag ac 22

<210> SEQ ID NO 150
<211> LENGTH: 22
<212> TYPE: RNA
<213> ORGANISM: Homo sapiens

<400> SEQUENCE: 150
ucagugcacu acagaacuuu gu 22

<210> SEQ ID NO 151
<211> LENGTH: 22
<212> TYPE: RNA
<213> ORGANISM: Homo sapiens

<400> SEQUENCE: 151
ucagugcauc acagaacuuu gu 22

<210> SEQ ID NO 152
<211> LENGTH: 21
<212> TYPE: RNA
<213> ORGANISM: Homo sapiens

<400> SEQUENCE: 152
ucagugcaug acagaacuug g 21

<210> SEQ ID NO 153
<211> LENGTH: 22
<212> TYPE: RNA
<213> ORGANISM: Homo sapiens

<400> SEQUENCE: 153
uaaauagagu aggcaaagga ca 22

<210> SEQ ID NO 154
<211> LENGTH: 22
<212> TYPE: RNA
<213> ORGANISM: Homo sapiens

<400> SEQUENCE: 154
aaacaaacau ggugcacuuc uu 22

<210> SEQ ID NO 155
<211> LENGTH: 21
<212> TYPE: RNA
<213> ORGANISM: Homo sapiens

<400> SEQUENCE: 155
ucugaauugu aagaguuguu a 21

<210> SEQ ID NO 156
<211> LENGTH: 80
<212> TYPE: RNA
<213> ORGANISM: Homo sapiens

<400> SEQUENCE: 156
gguaccugag aagagguugu cugugaugag uucgcuuuua uuaaugacga auauaacaca 60
gauggccugu uuucaguacc 80

<210> SEQ ID NO 157
<211> LENGTH: 73
<212> TYPE: RNA
<213> ORGANISM: Homo sapiens

<400> SEQUENCE: 157
uuccucaucu auaaaaugag ggcaguaaga ccuuccuucc uugucuuacu acccccauuu 60
uauagaugag gaa 73

<210> SEQ ID NO 158
<211> LENGTH: 68
<212> TYPE: RNA
<213> ORGANISM: Homo sapiens

<400> SEQUENCE: 158
gaggcaaagu ucugagacac uccgacucug aguaugauag aagucagugc acuacagaac 60
uuugucuc 68

<210> SEQ ID NO 159
<211> LENGTH: 99
<212> TYPE: RNA
<213> ORGANISM: Homo sapiens

<400> SEQUENCE: 159
caagcacgau uagcauuuga ggugaaguuc uguuauacac ucaggcugug gcucucugaa 60
agucagugca ucacagaacu uugucucgaa agcuuucua 99

<210> SEQ ID NO 160
<211> LENGTH: 87
<212> TYPE: RNA
<213> ORGANISM: Homo sapiens

<400> SEQUENCE: 160 ugucccccc ggcccagguu cugugauaca cuccgacucg ggcucuggag cagucagugc 60
augacagaac uugggcccgg aaggacc 87

<210> SEQ ID NO 161
<211> LENGTH: 77
<212> TYPE: RNA
<213> ORGANISM: Homo sapiens

<400> SEQUENCE: 161
aaaugguuau guccuuugcc uauucuauuu aagacacccu guaccuuaaa uagaguaggc 60
aaaggacaga aacauuu 77

<210> SEQ ID NO 162
<211> LENGTH: 82

<212> TYPE: RNA
<213> ORGANISM: Homo sapiens

<400> SEQUENCE: 162
ugguaccuga aaagaaguug cccauguuau uuucgcuuua uaugugacga aacaaacaug 60
gugcacuucu uuuucgguau ca 82

<210> SEQ ID NO 163
<211> LENGTH: 66
<212> TYPE: RNA
<213> ORGANISM: Homo sapiens

<400> SEQUENCE: 163
uauaagaacu cuugcagucu uagauguuau aaaaauauau aucugaauug uaagaguugu 60
uagcac 66

<210> SEQ ID NO 164
<211> LENGTH: 22
<212> TYPE: RNA
<213> ORGANISM: Homo sapiens

<400> SEQUENCE: 164
uauugcacuu gucccggccu gu 22

<210> SEQ ID NO 165
<211> LENGTH: 22
<212> TYPE: RNA
<213> ORGANISM: Homo sapiens

<400> SEQUENCE: 165
uauugcacuu gucccggccu gu 22

<210> SEQ ID NO 166
<211> LENGTH: 22
<212> TYPE: RNA
<213> ORGANISM: Homo sapiens

<400> SEQUENCE: 166
uagcuuauca gacugauguu ga 22

<210> SEQ ID NO 167
<211> LENGTH: 22
<212> TYPE: RNA
<213> ORGANISM: Homo sapiens

<400> SEQUENCE: 167
uucaaguaau ccaggauagg cu 22

<210> SEQ ID NO 168
<211> LENGTH: 22
<212> TYPE: RNA
<213> ORGANISM: Homo sapiens

<400> SEQUENCE: 168
uucaaguaau ccaggauagg cu 22

<210> SEQ ID NO 169
<211> LENGTH: 23
<212> TYPE: RNA
<213> ORGANISM: Homo sapiens

<400> SEQUENCE: 169
uaaggugcau cuagugcaga uag 23

<210> SEQ ID NO 170
<211> LENGTH: 20
<212> TYPE: RNA
<213> ORGANISM: Homo sapiens

<400> SEQUENCE: 170
uaaggcacgc ggugaaugcc 20

<210> SEQ ID NO 171
<211> LENGTH: 20
<212> TYPE: RNA
<213> ORGANISM: Homo sapiens

<400> SEQUENCE: 171
uaaggcacgc ggugaaugcc 20

<210> SEQ ID NO 172
<211> LENGTH: 20
<212> TYPE: RNA
<213> ORGANISM: Homo sapiens

<400> SEQUENCE: 172
uaaggcacgc ggugaaugcc 20

<210> SEQ ID NO 173
<211> LENGTH: 22
<212> TYPE: RNA
<213> ORGANISM: Homo sapiens

<400> SEQUENCE: 173
aacccguaga uccgaucuug ug 22

<210> SEQ ID NO 174
<211> LENGTH: 23
<212> TYPE: RNA
<213> ORGANISM: Homo sapiens

<400> SEQUENCE: 174
uguaaacauc cuacacucuc agc 23

<210> SEQ ID NO 175
<211> LENGTH: 23
<212> TYPE: RNA
<213> ORGANISM: Homo sapiens

<400> SEQUENCE: 175
cagugcaaua guauugucaa agc 23

<210> SEQ ID NO 176
<211> LENGTH: 23
<212> TYPE: RNA
<213> ORGANISM: Homo sapiens

<400> SEQUENCE: 176
guccaguuuu cccaggaauc ccu 23

<210> SEQ ID NO 177
<211> LENGTH: 22
<212> TYPE: RNA
<213> ORGANISM: Homo sapiens

<400> SEQUENCE: 177
ggugcagugc ugcaucucug gu 22

<210> SEQ ID NO 178
<211> LENGTH: 23
<212> TYPE: RNA
<213> ORGANISM: Homo sapiens

<400> SEQUENCE: 178
gaagugcuuc gauuuugggg ugu 23

<210> SEQ ID NO 179
<211> LENGTH: 23
<212> TYPE: RNA
<213> ORGANISM: Homo sapiens

<400> SEQUENCE: 179
caaagugcuc auagugcagg uag 23

<210> SEQ ID NO 180
<211> LENGTH: 22
<212> TYPE: RNA
<213> ORGANISM: Homo sapiens

<400> SEQUENCE: 180
uagcaccauu ugaaaucggu ua 22

<210> SEQ ID NO 181
<211> LENGTH: 23
<212> TYPE: RNA
<213> ORGANISM: Homo sapiens

<400> SEQUENCE: 181
uagcaccauu ugaaaucagu guu 23

<210> SEQ ID NO 182
<211> LENGTH: 22
<212> TYPE: RNA
<213> ORGANISM: Homo sapiens

<400> SEQUENCE: 182
ugagguagua guuuguacag uu 22

<210> SEQ ID NO 183
<211> LENGTH: 22
<212> TYPE: RNA
<213> ORGANISM: Homo sapiens

<400> SEQUENCE: 183
ugagguagua gguuguauag uu 22

<210> SEQ ID NO 184
<211> LENGTH: 22
<212> TYPE: RNA
<213> ORGANISM: Homo sapiens

<400> SEQUENCE: 184
ugagguagua gguugugugg uu 22

<210> SEQ ID NO 185
<211> LENGTH: 22
<212> TYPE: RNA
<213> ORGANISM: Homo sapiens

<400> SEQUENCE: 185
ugagguagua aguuguauug uu 22

<210> SEQ ID NO 186
<211> LENGTH: 22
<212> TYPE: RNA
<213> ORGANISM: Homo sapiens

<400> SEQUENCE: 186
cuuucagucg gauguuugca gc 22

<210> SEQ ID NO 187
<211> LENGTH: 23
<212> TYPE: RNA
<213> ORGANISM: Homo sapiens

<400> SEQUENCE: 187
caaagugcuu acagugcagg uag 23

<210> SEQ ID NO 188
<211> LENGTH: 22
<212> TYPE: RNA
<213> ORGANISM: Homo sapiens

<400> SEQUENCE: 188
uggaauguaa agaaguaugu au 22

<210> SEQ ID NO 189
<211> LENGTH: 22
<212> TYPE: RNA
<213> ORGANISM: Homo sapiens

<400> SEQUENCE: 189
uggaauguaa agaaguaugu au 22

<210> SEQ ID NO 190
<211> LENGTH: 21
<212> TYPE: RNA
<213> ORGANISM: Homo sapiens

<400> SEQUENCE: 190
cugaccuaug aauugacagc c 21

<210> SEQ ID NO 191
<211> LENGTH: 23
<212> TYPE: RNA
<213> ORGANISM: Homo sapiens

<400> SEQUENCE: 191
uuaaugcuaa ucgugauagg ggu 23

<210> SEQ ID NO 192
<211> LENGTH: 23
<212> TYPE: RNA
<213> ORGANISM: Homo sapiens

<400> SEQUENCE: 192
uucucgagga aagaagcacu uuc 23

<210> SEQ ID NO 193
<211> LENGTH: 18
<212> TYPE: RNA
<213> ORGANISM: Homo sapiens

<400> SEQUENCE: 193
ugcuuccuuu cagagggu 18

<210> SEQ ID NO 194
<211> LENGTH: 21
<212> TYPE: RNA
<213> ORGANISM: Homo sapiens

<400> SEQUENCE: 194
aggcaagaug cuggcauagc u 21

<210> SEQ ID NO 195
<211> LENGTH: 23
<212> TYPE: RNA
<213> ORGANISM: Homo sapiens

<400> SEQUENCE: 195
aacauucaac gcugucggug agu 23

<210> SEQ ID NO 196
<211> LENGTH: 23
<212> TYPE: RNA
<213> ORGANISM: Homo sapiens

<400> SEQUENCE: 196
aacauucaac gcugucggug agu 23

<210> SEQ ID NO 197
<211> LENGTH: 23
<212> TYPE: RNA
<213> ORGANISM: Homo sapiens

<400> SEQUENCE: 197
aacauucauu gcugucggug ggu 23

<210> SEQ ID NO 198
<211> LENGTH: 23
<212> TYPE: RNA
<213> ORGANISM: Homo sapiens

<400> SEQUENCE: 198
aacauucauu gcugucggug ggu 23

<210> SEQ ID NO 199
<211> LENGTH: 22
<212> TYPE: RNA
<213> ORGANISM: Homo sapiens

<400> SEQUENCE: 199
aacauucaac cugucgguga gu 22

<210> SEQ ID NO 200
<211> LENGTH: 23
<212> TYPE: RNA
<213> ORGANISM: Homo sapiens

<400> SEQUENCE: 200
aggcagugua guuagcugau ugc 23

<210> SEQ ID NO 201
<211> LENGTH: 23
<212> TYPE: RNA

<213> ORGANISM: Homo sapiens

<400> SEQUENCE: 201
uaggcagugu cauuagcuga uug 23

<210> SEQ ID NO 202
<211> LENGTH: 23
<212> TYPE: RNA
<213> ORGANISM: Homo sapiens

<400> SEQUENCE: 202
agcagcauug uacagggcua uga 23

<210> SEQ ID NO 203
<211> LENGTH: 23
<212> TYPE: RNA
<213> ORGANISM: Homo sapiens

<400> SEQUENCE: 203
agcagcauug uacagggcua uga 23

<210> SEQ ID NO 204
<211> LENGTH: 22
<212> TYPE: RNA
<213> ORGANISM: Homo sapiens

<400> SEQUENCE: 204
cugugcgugu gacagcggcu ga 22

<210> SEQ ID NO 205
<211> LENGTH: 22
<212> TYPE: RNA
<213> ORGANISM: Homo sapiens

<400> SEQUENCE: 205
uagcagcacg uaaauauugg cg 22

<210> SEQ ID NO 206
<211> LENGTH: 22
<212> TYPE: RNA
<213> ORGANISM: Homo sapiens

<400> SEQUENCE: 206
uagcagcacg uaaauauugg cg 22

<210> SEQ ID NO 207
<211> LENGTH: 22
<212> TYPE: RNA
<213> ORGANISM: Homo sapiens

<400> SEQUENCE: 207
uguaaacauc cucgacugga ag 22

<210> SEQ ID NO 208
<211> LENGTH: 21
<212> TYPE: RNA
<213> ORGANISM: Homo sapiens

<400> SEQUENCE: 208
aggcaagaug cuggcauagc u 21

<210> SEQ ID NO 209
<211> LENGTH: 21

<212> TYPE: RNA
<213> ORGANISM: Homo sapiens

<400> SEQUENCE: 209
agcuacaucu ggcuacuggg u 21

<210> SEQ ID NO 210
<211> LENGTH: 23
<212> TYPE: RNA
<213> ORGANISM: Homo sapiens

<400> SEQUENCE: 210
caaagugcuu acagugcagg uag 23

<210> SEQ ID NO 211
<211> LENGTH: 22
<212> TYPE: RNA
<213> ORGANISM: Homo sapiens

<400> SEQUENCE: 211
acugcaguga aggcacuugu ag 22

<210> SEQ ID NO 212
<211> LENGTH: 22
<212> TYPE: RNA
<213> ORGANISM: Homo sapiens

<400> SEQUENCE: 212
uaauacugcc ugguaaugau ga 22

<210> SEQ ID NO 213
<211> LENGTH: 23
<212> TYPE: RNA
<213> ORGANISM: Homo sapiens

<400> SEQUENCE: 213
uaauacugcc ggguaaugau gga 23

<210> SEQ ID NO 214
<211> LENGTH: 21
<212> TYPE: RNA
<213> ORGANISM: Homo sapiens

<400> SEQUENCE: 214
ucacagugaa ccggucucuu u 21

<210> SEQ ID NO 215
<211> LENGTH: 23
<212> TYPE: RNA
<213> ORGANISM: Homo sapiens

<400> SEQUENCE: 215
uagcagcggg aacaguucug cag 23

<210> SEQ ID NO 216
<211> LENGTH: 22
<212> TYPE: RNA
<213> ORGANISM: Homo sapiens

<400> SEQUENCE: 216
cagcagcaau ucauguuuug aa 22

<210> SEQ ID NO 217

<211> LENGTH: 21
<212> TYPE: RNA
<213> ORGANISM: Homo sapiens

<400> SEQUENCE: 217
uagcagcaca gaaauauugg c 21

<210> SEQ ID NO 218
<211> LENGTH: 22
<212> TYPE: RNA
<213> ORGANISM: Homo sapiens

<400> SEQUENCE: 218
aggcauugac uucucacuag cu 22

<210> SEQ ID NO 219
<211> LENGTH: 22
<212> TYPE: RNA
<213> ORGANISM: Homo sapiens

<400> SEQUENCE: 219
gugaaauguu uaggaccacu ag 22

<210> SEQ ID NO 220
<211> LENGTH: 22
<212> TYPE: RNA
<213> ORGANISM: Homo sapiens

<400> SEQUENCE: 220
acaguagucu gcacauuggu ua 22

<210> SEQ ID NO 221
<211> LENGTH: 23
<212> TYPE: RNA
<213> ORGANISM: Homo sapiens

<400> SEQUENCE: 221
cccaguguuc agacuaccug uuc 23

<210> SEQ ID NO 222
<211> LENGTH: 22
<212> TYPE: RNA
<213> ORGANISM: Homo sapiens

<400> SEQUENCE: 222
acaguagucu gcacauuggu ua 22

<210> SEQ ID NO 223
<211> LENGTH: 23
<212> TYPE: RNA
<213> ORGANISM: Homo sapiens

<400> SEQUENCE: 223
caaagugcug uucgugcagg uag 23

<210> SEQ ID NO 224
<211> LENGTH: 22
<212> TYPE: RNA
<213> ORGANISM: Homo sapiens

<400> SEQUENCE: 224
ugagguagua aguuguauug uu 22

<210> SEQ ID NO 225
<211> LENGTH: 24
<212> TYPE: RNA
<213> ORGANISM: Homo sapiens

<400> SEQUENCE: 225
ucccugagac ccuuuaaccu guga 24

<210> SEQ ID NO 226
<211> LENGTH: 22
<212> TYPE: RNA
<213> ORGANISM: Homo sapiens

<400> SEQUENCE: 226
uuuggucccc uucaaccagc ug 22

<210> SEQ ID NO 227
<211> LENGTH: 22
<212> TYPE: RNA
<213> ORGANISM: Homo sapiens

<400> SEQUENCE: 227
uuuggucccc uucaaccagc ua 22

<210> SEQ ID NO 228
<211> LENGTH: 22
<212> TYPE: RNA
<213> ORGANISM: Homo sapiens

<400> SEQUENCE: 228
ucguaccgug aguaauaaug cg 22

<210> SEQ ID NO 229
<211> LENGTH: 22
<212> TYPE: RNA
<213> ORGANISM: Homo sapiens

<400> SEQUENCE: 229
uguaacagca acuccaugug ga 22

<210> SEQ ID NO 230
<211> LENGTH: 23
<212> TYPE: RNA
<213> ORGANISM: Homo sapiens

<400> SEQUENCE: 230
ugucugcccg caugccugcc ucu 23

<210> SEQ ID NO 231
<211> LENGTH: 22
<212> TYPE: RNA
<213> ORGANISM: Homo sapiens

<400> SEQUENCE: 231
uagcagcaca ucaugguuua ca 22

<210> SEQ ID NO 232
<211> LENGTH: 22
<212> TYPE: RNA
<213> ORGANISM: Homo sapiens

<400> SEQUENCE: 232
uccagcauca gugauuuugu ug 22

<210> SEQ ID NO 233
<211> LENGTH: 22
<212> TYPE: RNA
<213> ORGANISM: Homo sapiens

<400> SEQUENCE: 233
uccuucauuc caccggaguc ug 22

<210> SEQ ID NO 234
<211> LENGTH: 22
<212> TYPE: RNA
<213> ORGANISM: Homo sapiens

<400> SEQUENCE: 234
ucaccagccc uguguucccu ag 22

<210> SEQ ID NO 235
<211> LENGTH: 23
<212> TYPE: RNA
<213> ORGANISM: Homo sapiens

<400> SEQUENCE: 235
aaggagcuua caaucuagcu ggg 23

<210> SEQ ID NO 236
<211> LENGTH: 22
<212> TYPE: RNA
<213> ORGANISM: Homo sapiens

<400> SEQUENCE: 236
uggcagugua uuguuagcug gu 22

<210> SEQ ID NO 237
<211> LENGTH: 22
<212> TYPE: RNA
<213> ORGANISM: Homo sapiens

<400> SEQUENCE: 237
acuggacuua gggucagaag gc 22

<210> SEQ ID NO 238
<211> LENGTH: 22
<212> TYPE: RNA
<213> ORGANISM: Homo sapiens

<400> SEQUENCE: 238
uuauaaagca augagacuga uu 22

<210> SEQ ID NO 239
<211> LENGTH: 23
<212> TYPE: RNA
<213> ORGANISM: Homo sapiens

<400> SEQUENCE: 239
uaaaucccau ggugccuucu ccu 23

<210> SEQ ID NO 240
<211> LENGTH: 22
<212> TYPE: RNA
<213> ORGANISM: Homo sapiens

<400> SEQUENCE: 240
aaaaugguuc ccuuuagagu gu 22

<210> SEQ ID NO 241
<211> LENGTH: 22
<212> TYPE: RNA
<213> ORGANISM: Homo sapiens

<400> SEQUENCE: 241
aggcggggcg ccgcgggacc gc 22

<210> SEQ ID NO 242
<211> LENGTH: 22
<212> TYPE: RNA
<213> ORGANISM: Homo sapiens

<400> SEQUENCE: 242
cagugcaaug uuaaaagggc au 22

<210> SEQ ID NO 243
<211> LENGTH: 22
<212> TYPE: RNA
<213> ORGANISM: Homo sapiens

<400> SEQUENCE: 243
cagugcaaug augaaagggc au 22

<210> SEQ ID NO 244
<211> LENGTH: 22
<212> TYPE: RNA
<213> ORGANISM: Homo sapiens

<400> SEQUENCE: 244
ucuucucugu uuuggccaug ug 22

<210> SEQ ID NO 245
<211> LENGTH: 20
<212> TYPE: RNA
<213> ORGANISM: Homo sapiens

<400> SEQUENCE: 245
guccgcucgg cgguggccca 20

<210> SEQ ID NO 246
<211> LENGTH: 23
<212> TYPE: RNA
<213> ORGANISM: Homo sapiens

<400> SEQUENCE: 246
aucgcugcgg uugcgagcgc ugu 23

<210> SEQ ID NO 247
<211> LENGTH: 22
<212> TYPE: RNA
<213> ORGANISM: Homo sapiens

<400> SEQUENCE: 247
uggugggccg cagaacaugu gc 22

<210> SEQ ID NO 248
<211> LENGTH: 22
<212> TYPE: RNA
<213> ORGANISM: Homo sapiens

<400> SEQUENCE: 248
uucccuuugu cauccuaugc cu 22

<210> SEQ ID NO 249
<211> LENGTH: 21
<212> TYPE: RNA
<213> ORGANISM: Homo sapiens

<400> SEQUENCE: 249
caagucacua gugguuccgu u 21

<210> SEQ ID NO 250
<211> LENGTH: 22
<212> TYPE: RNA
<213> ORGANISM: Homo sapiens

<400> SEQUENCE: 250
agucauugga ggguuugagc ag 22

<210> SEQ ID NO 251
<211> LENGTH: 22
<212> TYPE: RNA
<213> ORGANISM: Homo sapiens

<400> SEQUENCE: 251
uggaguguga caaugguguu ug 22

<210> SEQ ID NO 252
<211> LENGTH: 22
<212> TYPE: RNA
<213> ORGANISM: Homo sapiens

<400> SEQUENCE: 252
uaugugggau gguaaaccgc uu 22

<210> SEQ ID NO 253
<211> LENGTH: 22
<212> TYPE: RNA
<213> ORGANISM: Homo sapiens

<400> SEQUENCE: 253
ugguuuaccg ucccacauac au 22

<210> SEQ ID NO 254
<211> LENGTH: 22
<212> TYPE: RNA
<213> ORGANISM: Homo sapiens

<400> SEQUENCE: 254
aacccguaga uccgaacuug ug 22

<210> SEQ ID NO 255
<211> LENGTH: 23
<212> TYPE: RNA
<213> ORGANISM: Homo sapiens

<400> SEQUENCE: 255
agcugguguu gugaaucagg ccg 23

<210> SEQ ID NO 256
<211> LENGTH: 22
<212> TYPE: RNA
<213> ORGANISM: Homo sapiens

<400> SEQUENCE: 256
cagugguuuu acccuauggu ag 22

<210> SEQ ID NO 257
<211> LENGTH: 22
<212> TYPE: RNA
<213> ORGANISM: Homo sapiens

<400> SEQUENCE: 257
uuuguucguu cggcucgcgu ga 22

<210> SEQ ID NO 258
<211> LENGTH: 23
<212> TYPE: RNA
<213> ORGANISM: Homo sapiens

<400> SEQUENCE: 258
uacugcauca ggaacugauu gga 23

<210> SEQ ID NO 259
<211> LENGTH: 23
<212> TYPE: RNA
<213> ORGANISM: Homo sapiens

<400> SEQUENCE: 259
aaagugcugc gacauuugag cgu 23

<210> SEQ ID NO 260
<211> LENGTH: 23
<212> TYPE: RNA
<213> ORGANISM: Homo sapiens

<400> SEQUENCE: 260
uuuggcacua gcacauuuuu gcu 23

<210> SEQ ID NO 261
<211> LENGTH: 22
<212> TYPE: RNA
<213> ORGANISM: Homo sapiens

<400> SEQUENCE: 261
ucggauccgu cugagcuugg cu 22

<210> SEQ ID NO 262
<211> LENGTH: 23
<212> TYPE: RNA
<213> ORGANISM: Homo sapiens

<400> SEQUENCE: 262
uauggcuuuu cauuccuaug uga 23

<210> SEQ ID NO 263
<211> LENGTH: 21
<212> TYPE: RNA
<213> ORGANISM: Homo sapiens

<400> SEQUENCE: 263
uacaguacug ugauaacuga a 21

<210> SEQ ID NO 264
<211> LENGTH: 20
<212> TYPE: RNA
<213> ORGANISM: Homo sapiens

<400> SEQUENCE: 264
ccucugggcc cuuccuccag 20

<210> SEQ ID NO 265
<211> LENGTH: 23
<212> TYPE: RNA
<213> ORGANISM: Homo sapiens

<400> SEQUENCE: 265 cgcaucccu agggcauugg ugu 23

<210> SEQ ID NO 266
<211> LENGTH: 20
<212> TYPE: RNA
<213> ORGANISM: Homo sapiens

<400> SEQUENCE: 266
acugccccag gugcugcugg 20

<210> SEQ ID NO 267
<211> LENGTH: 23
<212> TYPE: RNA
<213> ORGANISM: Homo sapiens

<400> SEQUENCE: 267
ucaagagcaa uaacgaaaaa ugu 23

<210> SEQ ID NO 268
<211> LENGTH: 22
<212> TYPE: RNA
<213> ORGANISM: Homo sapiens

<400> SEQUENCE: 268
uaacacuguc ugguaaagau gg 22

<210> SEQ ID NO 269
<211> LENGTH: 78
<212> TYPE: RNA
<213> ORGANISM: Homo sapiens

<400> SEQUENCE: 269
cuuucuacac agguugggau cgguugcaau gcuguguuuc uguaugguau ugcacuuguc 60
ccggccuguu gaguuugg 78

<210> SEQ ID NO 270
<211> LENGTH: 75
<212> TYPE: RNA
<213> ORGANISM: Homo sapiens

<400> SEQUENCE: 270
ucaucccugg guggggauuu guugcauuac uuguguucua uauaaaguau ugcacuuguc 60
ccggccugug gaaga 75

<210> SEQ ID NO 271
<211> LENGTH: 72
<212> TYPE: RNA
<213> ORGANISM: Homo sapiens

<400> SEQUENCE: 271
ugucggguag cuuaucagac ugauguugac uguugaaucu cauggcaaca ccagucgaug 60
ggcugucuga ca 72

<210> SEQ ID NO 272
<211> LENGTH: 77
<212> TYPE: RNA
<213> ORGANISM: Homo sapiens

<400> SEQUENCE: 272
guggccucgu ucaaguaauc caggauaggc ugugcagguc ccaaugggcc uauucuuggu 60
uacuugcacg gggacgc 77

<210> SEQ ID NO 273
<211> LENGTH: 84
<212> TYPE: RNA
<213> ORGANISM: Homo sapiens

<400> SEQUENCE: 273
ggcuguggcu ggauucaagu aauccaggau aggcuguuuc caucugugag gccuauucuu 60
gauuacuugu uucuggaggc agcu 84

<210> SEQ ID NO 274
<211> LENGTH: 71
<212> TYPE: RNA
<213> ORGANISM: Homo sapiens

<400> SEQUENCE: 274
uguucuaagg ugcaucuagu gcagauagug aaguagauua gcaucuacug cccuaagugc 60
uccuucuggc a 71

<210> SEQ ID NO 275
<211> LENGTH: 87
<212> TYPE: RNA
<213> ORGANISM: Homo sapiens

<400> SEQUENCE: 275
ugagggcccc ucugcguguu cacagcggac cuugauuuaa ugucuauaca auuaaggcac 60
gcggugaaug ccaagagagg cgccucc 87

<210> SEQ ID NO 276
<211> LENGTH: 85
<212> TYPE: RNA
<213> ORGANISM: Homo sapiens

<400> SEQUENCE: 276
aggccucucu cuccguguuc acagcggacc uugauuuaaa uguccauaca auuaaggcac 60
gcggugaaug ccaagaaugg ggcug 85

<210> SEQ ID NO 277
<211> LENGTH: 109
<212> TYPE: RNA
<213> ORGANISM: Homo sapiens

<400> SEQUENCE: 277
aucaagauua gaggcucugc ucuccguguu cacagcggac cuugauuuaa ugucauacaa 60
uuaaggcacg cggugaaugc caagagcgga gccuacggcu gcacuugaa 109

<210> SEQ ID NO 278
<211> LENGTH: 81
<212> TYPE: RNA
<213> ORGANISM: Homo sapiens

<400> SEQUENCE: 278
cccauuggca uaaacccgua gauccgaucu uguggugaag uggaccgcac aagcucgcuu 60
cuaugggucu gugucagugu g 81

<210> SEQ ID NO 279
<211> LENGTH: 89
<212> TYPE: RNA
<213> ORGANISM: Homo sapiens

<400> SEQUENCE: 279
accaugcugu agugugugua aacauccuac acucucagcu gugagcucaa gguggcuggg 60
agaggguugu uuacuccuuc ugccaugga 89

<210> SEQ ID NO 280
<211> LENGTH: 72
<212> TYPE: RNA
<213> ORGANISM: Homo sapiens

<400> SEQUENCE: 280
agauacugua aacauccuac acucucagcu guggaaagua agaaagcugg gagaaggcug 60
uuuacucuuu cu 72

<210> SEQ ID NO 281
<211> LENGTH: 86
<212> TYPE: RNA
<213> ORGANISM: Homo sapiens

<400> SEQUENCE: 281
acugcuaacg aaugcucuga cuuuauugca cuacuguacu uuacagcuag cagugcaaua 60
guauugucaa agcaucugaa agcagg 86

<210> SEQ ID NO 282
<211> LENGTH: 88
<212> TYPE: RNA
<213> ORGANISM: Homo sapiens

<400> SEQUENCE: 282
caccuugucc ucacggucca guuuucccag gaaucccuua gaugcuaaga uggggauucc 60
uggaaauacu guucuugagg ucaugguu 88

<210> SEQ ID NO 283
<211> LENGTH: 106
<212> TYPE: RNA
<213> ORGANISM: Homo sapiens

<400> SEQUENCE: 283
gcgcagcgcc cugucuccca gccugaggug cagugcugca ucucugguca guugggaguc 60
ugagaugaag cacuguagcu caggaagaga gaaguuguuc ugcagc 106

<210> SEQ ID NO 284
<211> LENGTH: 69
<212> TYPE: RNA
<213> ORGANISM: Homo sapiens

<400> SEQUENCE: 284
gggauacuca aaaugggggc gcuuuccuuu uugucuguac ugggaagugc uucgauuuug 60
gggugucccc 69

```
<210> SEQ ID NO 285
<211> LENGTH: 69
<212> TYPE: RNA
<213> ORGANISM: Homo sapiens

<400> SEQUENCE: 285

aguaccaaag ugcucauagu gcagguaguu uuggcaugac ucuacuguag uaugggcacu    60

uccaguacu                                                          69

<210> SEQ ID NO 286
<211> LENGTH: 88
<212> TYPE: RNA
<213> ORGANISM: Homo sapiens

<400> SEQUENCE: 286

aucucuuaca caggcugacc gauuucuccu gguguucaga gucuguuuuu gucuagcacc    60

auuugaaauc gguuaugaug uaggggga                                      88

<210> SEQ ID NO 287
<211> LENGTH: 81
<212> TYPE: RNA
<213> ORGANISM: Homo sapiens

<400> SEQUENCE: 287

cuucaggaag cugguuucau auggugguuu agauuuaaau agugauuguc uagcaccauu    60

ugaaaucagu guucuugggg g                                             81

<210> SEQ ID NO 288
<211> LENGTH: 81
<212> TYPE: RNA
<213> ORGANISM: Homo sapiens

<400> SEQUENCE: 288

cuucuggaag cugguuucac augguggcuu agauuuuucc aucuuuguau cuagcaccau    60

uugaaaucag uguuuuagga g                                             81

<210> SEQ ID NO 289
<211> LENGTH: 84
<212> TYPE: RNA
<213> ORGANISM: Homo sapiens

<400> SEQUENCE: 289

aggcugaggu aguaguuugu acaguuugag ggucuaugau accacccggu acaggagaua    60

acuguacagg ccacugccuu gcca                                          84

<210> SEQ ID NO 290
<211> LENGTH: 80
<212> TYPE: RNA
<213> ORGANISM: Homo sapiens

<400> SEQUENCE: 290

ugggaugagg uaguagguug uauaguuuua gggucacacc caccacuggg agauaacuau    60

acaaucuacu gucuuuccua                                               80

<210> SEQ ID NO 291
<211> LENGTH: 72
<212> TYPE: RNA
<213> ORGANISM: Homo sapiens

<400> SEQUENCE: 291
```

agguugaggu aguagguugu auaguuuaga auuacaucaa gggagauaac uguacagccu 60
ccuagcuuuc cu 72

<210> SEQ ID NO 292
<211> LENGTH: 74
<212> TYPE: RNA
<213> ORGANISM: Homo sapiens

<400> SEQUENCE: 292
gggugaggua guagguugua uaguuugggg cucugcccug cuaugggaua acuauacaau 60
cuacugucuu uccu 74

<210> SEQ ID NO 293
<211> LENGTH: 83
<212> TYPE: RNA
<213> ORGANISM: Homo sapiens

<400> SEQUENCE: 293
cggggugagg uaguagguug ugugguuuca gggcagugau guugccccuc ggaagauaac 60
uauacaaccu acugccuucc cug 83

<210> SEQ ID NO 294
<211> LENGTH: 119
<212> TYPE: RNA
<213> ORGANISM: Homo sapiens

<400> SEQUENCE: 294
aggauucugc ucaugccagg gugagguagu aaguuguauu guuguggggu agggauauua 60
ggccccaauu agaagauaac uauacaacuu acuacuuucc cuggugugug gcauauuca 119

<210> SEQ ID NO 295
<211> LENGTH: 71
<212> TYPE: RNA
<213> ORGANISM: Homo sapiens

<400> SEQUENCE: 295
gcgacuguaa acauccucga cuggaagcug ugaagccaca gaugggcuuu cagucggaug 60
uuugcagcug c 71

<210> SEQ ID NO 296
<211> LENGTH: 84
<212> TYPE: RNA
<213> ORGANISM: Homo sapiens

<400> SEQUENCE: 296
gucagaauaa ugucaaagug cuuacagugc agguagugau augugcaucu acugcaguga 60
aggcacuugu agcauuaugg ugac 84

<210> SEQ ID NO 297
<211> LENGTH: 71
<212> TYPE: RNA
<213> ORGANISM: Homo sapiens

<400> SEQUENCE: 297
ugggaaacau acuucuuuau augcccauau ggaccugcua agcuauggaa uguaaagaag 60
uauguaucuc a 71

<210> SEQ ID NO 298
<211> LENGTH: 85

<212> TYPE: RNA
<213> ORGANISM: Homo sapiens

<400> SEQUENCE: 298
accuacucag aguacauacu ucuuuaugua cccauaugaa cauacaaugc uauggaaugu 60
aaagaaguau guauuuuugg uaggc 85

<210> SEQ ID NO 299
<211> LENGTH: 110
<212> TYPE: RNA
<213> ORGANISM: Homo sapiens

<400> SEQUENCE: 299
gccgagaccg agugcacagg gcucugaccu augaauugac agccagugcu cucgucuccc 60
cucuggcugc caauuccaua ggucacaggu auguucgccu caaugccagc 110

<210> SEQ ID NO 300
<211> LENGTH: 65
<212> TYPE: RNA
<213> ORGANISM: Homo sapiens

<400> SEQUENCE: 300
cuguuaaugc uaaucgugau aggggguuuu gccuccaacu gacuccuaca uauuagcauu 60
aacag 65

<210> SEQ ID NO 301
<211> LENGTH: 90
<212> TYPE: RNA
<213> ORGANISM: Homo sapiens

<400> SEQUENCE: 301
ucucaggcug ugaccuucuc gaggaaagaa gcacuuucug uugucugaaa gaaaagaaag 60
ugcuuccuuu cagaggguua cgguuugaga 90

<210> SEQ ID NO 302
<211> LENGTH: 90
<212> TYPE: RNA
<213> ORGANISM: Homo sapiens

<400> SEQUENCE: 302
ucucagguug ugaccuucuc gaggaaagaa gcacuuucug uugucugaaa gaaaagaaag 60
ugcuuccuuu cagaggguua cgguuugaga 90

<210> SEQ ID NO 303
<211> LENGTH: 71
<212> TYPE: RNA
<213> ORGANISM: Homo sapiens

<400> SEQUENCE: 303
ggagaggagg caagaugcug gcauagcugu ugaacuggga accugcuaug ccaacauauu 60
gccaucuuuc c 71

<210> SEQ ID NO 304
<211> LENGTH: 110
<212> TYPE: RNA
<213> ORGANISM: Homo sapiens

<400> SEQUENCE: 304
ugaguuuuga gguugcuuca gugaacauuc aacgcugucg gugaguuugg aauuaaaauc 60

-continued aaaaccaucg accguugauu guacccuaug gcuaaccauc aucuacucca 110

<210> SEQ ID NO 305
<211> LENGTH: 110
<212> TYPE: RNA
<213> ORGANISM: Homo sapiens

<400> SEQUENCE: 305
agaagggcua ucaggccagc cuucagagga cuccaaggaa cauucaacgc ugucggugag 60
uuugggauuu gaaaaaacca cugaccguug acuguaccuu ggggguccuua 110

<210> SEQ ID NO 306
<211> LENGTH: 110
<212> TYPE: RNA
<213> ORGANISM: Homo sapiens

<400> SEQUENCE: 306
ccugugcaga gauuauuuuu uaaaagguca caaucaacau ucauugcugu cgguggguug 60
aacugugugg acaagcucac ugaacaauga augcaacugu ggccccgcuu 110

<210> SEQ ID NO 307
<211> LENGTH: 89
<212> TYPE: RNA
<213> ORGANISM: Homo sapiens

<400> SEQUENCE: 307
cugauggcug cacucaacau ucauugcugu cgguggguuu gagucugaau caacucacug 60
aucaaugaau gcaaacugcg gaccaaaca 89

<210> SEQ ID NO 308
<211> LENGTH: 110
<212> TYPE: RNA
<213> ORGANISM: Homo sapiens

<400> SEQUENCE: 308
cggaaaauuu gccaaggguu ugggggaaca uucaaccugu cggugaguuu gggcagcuca 60
ggcaaaccau cgaccguuga guggacccug aggccuggaa uugccauccu 110

<210> SEQ ID NO 309
<211> LENGTH: 77
<212> TYPE: RNA
<213> ORGANISM: Homo sapiens

<400> SEQUENCE: 309
agucuaguua cuaggcagug uaguuagcug auugcuaaua guaccaauca cuaaccacac 60
ggccagguaa aaagauu 77

<210> SEQ ID NO 310
<211> LENGTH: 84
<212> TYPE: RNA
<213> ORGANISM: Homo sapiens

<400> SEQUENCE: 310
gugcucgguu uguaggcagu gucauuagcu gauuguacug uggugguuac aaucacuaac 60
uccacugcca ucaaaacaag gcac 84

<210> SEQ ID NO 311
<211> LENGTH: 78
<212> TYPE: RNA
<213> ORGANISM: Homo sapiens

<400> SEQUENCE: 311
uacugcccuc ggcuucuuua cagugcugcc uuguugcaua uggaucaagc agcauuguac 60
agggcuauga aggcauug 78

<210> SEQ ID NO 312
<211> LENGTH: 78
<212> TYPE: RNA
<213> ORGANISM: Homo sapiens

<400> SEQUENCE: 312
uugugcuuuc agcuucuuua cagugcugcc uuguagcauu caggucaagc agcauuguac 60
agggcuauga aagaacca 78

<210> SEQ ID NO 313
<211> LENGTH: 110
<212> TYPE: RNA
<213> ORGANISM: Homo sapiens

<400> SEQUENCE: 313
acccggcagu gccuccaggc gcagggcagc cccugcccac cgcacacugc gcugccccag 60
acccacugug cgugugacag cggcugaucu gugccugggc agcgcgaccc 110

<210> SEQ ID NO 314
<211> LENGTH: 89
<212> TYPE: RNA
<213> ORGANISM: Homo sapiens

<400> SEQUENCE: 314
gucagcagug ccuuagcagc acguaaauau uggcguuaag auucuaaaau uaucuccagu 60
auuaacugug cugcugaagu aagguugac 89

<210> SEQ ID NO 315
<211> LENGTH: 81
<212> TYPE: RNA
<213> ORGANISM: Homo sapiens

<400> SEQUENCE: 315
guuccacucu agcagcacgu aaauauuggc guagugaaau auauauuaaa caccaauauu 60
acugugcugc uuuaguguga c 81

<210> SEQ ID NO 316
<211> LENGTH: 71
<212> TYPE: RNA
<213> ORGANISM: Homo sapiens

<400> SEQUENCE: 316
gcgacuguaa acauccucga cuggaagcug ugaagccaca gaugggcuuu cagucggaug 60
uuugcagcug c 71

<210> SEQ ID NO 317
<211> LENGTH: 71
<212> TYPE: RNA
<213> ORGANISM: Homo sapiens

<400> SEQUENCE: 317
ggagaggagg caagaugcug gcauagcugu ugaacuggga accugcuaug ccaacauauu 60
gccaucuuuc c 71

<210> SEQ ID NO 318
<211> LENGTH: 110
<212> TYPE: RNA
<213> ORGANISM: Homo sapiens

<400> SEQUENCE: 318
gcugcuggaa gguguaggua cccucaaugg cucaguagcc aguguagauc cugucuuucg 60
uaaucagcag cuacaucugg cuacugggucu ucugauggca ucuucuagcu 110

<210> SEQ ID NO 319
<211> LENGTH: 84
<212> TYPE: RNA
<213> ORGANISM: Homo sapiens

<400> SEQUENCE: 319
gucagaauaa ugucaaagug cuuacagugc agguagugau augugcaucu acugcaguga 60
aggcacuugu agcauuaugg ugac 84

<210> SEQ ID NO 320
<211> LENGTH: 84
<212> TYPE: RNA
<213> ORGANISM: Homo sapiens

<400> SEQUENCE: 320
gucagaauaa ugucaaagug cuuacagugc agguagugau augugcaucu acugcaguga 60
aggcacuugu agcauuaugg ugac 84

<210> SEQ ID NO 321
<211> LENGTH: 95
<212> TYPE: RNA
<213> ORGANISM: Homo sapiens

<400> SEQUENCE: 321
ccagcucggg cagccguggc caucuuacug ggcagcauug gauggaguca ggucucuaau 60
acugccuggu aaugaugacg gcggagcccu gcacg 95

<210> SEQ ID NO 322
<211> LENGTH: 68
<212> TYPE: RNA
<213> ORGANISM: Homo sapiens

<400> SEQUENCE: 322
cccucgucuu acccagcagu guuugggugc gguugggagu cucuaauacu gccggguaau 60
gauggagg 68

<210> SEQ ID NO 323
<211> LENGTH: 82
<212> TYPE: RNA
<213> ORGANISM: Homo sapiens

<400> SEQUENCE: 323
ugagcuguug gauucggggc cguagcacug ucugagaggu uuacauuucu cacagugaac 60
cggucucuuu uucagcugcu uc 82

<210> SEQ ID NO 324
<211> LENGTH: 84
<212> TYPE: RNA
<213> ORGANISM: Homo sapiens

<400> SEQUENCE: 324
ugugcagugg gaagggggc cgauacacug uacgagagug aguagcaggu cucacaguga 60
accggucucu uucccuacug uguc 84

<210> SEQ ID NO 325
<211> LENGTH: 71
<212> TYPE: RNA
<213> ORGANISM: Homo sapiens

<400> SEQUENCE: 325
ugcccuagca gcgggaacag uucugcagug agcgaucggu gcucuggggu auuguuuccg 60
cugccagggu a 71

<210> SEQ ID NO 326
<211> LENGTH: 98
<212> TYPE: RNA
<213> ORGANISM: Homo sapiens

<400> SEQUENCE: 326
cgaggggaua cagcagcaau ucauguuuug aaguguucua aaugguucaa aacgugaggc 60
gcugcuauac ccccucgugg ggaagguaga aggugggg 98

<210> SEQ ID NO 327
<211> LENGTH: 87
<212> TYPE: RNA
<213> ORGANISM: Homo sapiens

<400> SEQUENCE: 327
agcuucccug gcucuagcag cacagaaaua uuggcacagg gaagcgaguc ugccaauauu 60
ggcugugcug cuccaggcag gguggug 87

<210> SEQ ID NO 328
<211> LENGTH: 119
<212> TYPE: RNA
<213> ORGANISM: Homo sapiens

<400> SEQUENCE: 328
agucagccug uugaagcuuu gaagcuuuga ugccaggcau ugacuucuca cuagcuguga 60
aaguccuagc uaaagagaag ucaaugcaug acaucuuguu ucaauagaug gcuguuuca 119

<210> SEQ ID NO 329
<211> LENGTH: 110
<212> TYPE: RNA
<213> ORGANISM: Homo sapiens

<400> SEQUENCE: 329
guguugggga cucgcgcgcu ggguccagug guucuuaaca guucaacagu ucuguagcgc 60
aauugugaaa uguuuaggac cacuagaccc ggcgggcgcg gcgacagcga 110

<210> SEQ ID NO 330
<211> LENGTH: 71
<212> TYPE: RNA
<213> ORGANISM: Homo sapiens

<400> SEQUENCE: 330
gccaacccag uguucagacu accuguucag gaggcucuca auguguacag uagucugcac 60
auugguuagg c 71

<210> SEQ ID NO 331

<211> LENGTH: 71
<212> TYPE: RNA
<213> ORGANISM: Homo sapiens

<400> SEQUENCE: 331
gccaacccag uguucagacu accuguucag gaggcucuca auguguacag uagucugcac 60
auugguuagg c 71

<210> SEQ ID NO 332
<211> LENGTH: 110
<212> TYPE: RNA
<213> ORGANISM: Homo sapiens

<400> SEQUENCE: 332
ccagaggaca ccuccacucc gucuacccag uguuuagacu aucuguucag gacucccaaa 60
uuguacagua gucugcacau ugguuaggcu gggcuggguu agacccucgg 110

<210> SEQ ID NO 333
<211> LENGTH: 80
<212> TYPE: RNA
<213> ORGANISM: Homo sapiens

<400> SEQUENCE: 333
cugggggcuc caaagugcug uucgugcagg uagugugauu acccaaccua cugcugagcu 60
agcacuuccc gagcccccgg 80

<210> SEQ ID NO 334
<211> LENGTH: 119
<212> TYPE: RNA
<213> ORGANISM: Homo sapiens

<400> SEQUENCE: 334
aggauucugc ucaugccagg gugagguagu aaguuguauu guuguggggu agggauauua 60
ggccccaauu agaagauaac uauacaacuu acuacuuucc cuggugugug gcauauuca 119

<210> SEQ ID NO 335
<211> LENGTH: 86
<212> TYPE: RNA
<213> ORGANISM: Homo sapiens

<400> SEQUENCE: 335
ugccagucuc uagguccug agacccuuua accugugagg acauccaggg ucacagguga 60
gguucuuggg agccuggcgu cuggcc 86

<210> SEQ ID NO 336
<211> LENGTH: 88
<212> TYPE: RNA
<213> ORGANISM: Homo sapiens

<400> SEQUENCE: 336
acaaugcuuu gcuagagcug guaaaaugga accaaaucgc cucuucaaug gauuuggucc 60
ccuucaacca gcuguagcua ugcauuga 88

<210> SEQ ID NO 337
<211> LENGTH: 102
<212> TYPE: RNA
<213> ORGANISM: Homo sapiens

<400> SEQUENCE: 337
gggagccaaa ugcuuugcua gagcugguaa aauggaacca aaucgacugu ccaauggauu 60 uggucccuu caaccagcug uagcugugca uugauggcgc cg 102

<210> SEQ ID NO 338
<211> LENGTH: 119
<212> TYPE: RNA
<213> ORGANISM: Homo sapiens

<400> SEQUENCE: 338
ccucagaaga aagaugcccc cugcucuggc uggucaaacg gaaccaaguc cgucuuccug 60
agagguuugg uccccuucaa ccagcuacag cagggcuggc aaugcccagu ccuuggaga 119

<210> SEQ ID NO 339
<211> LENGTH: 85
<212> TYPE: RNA
<213> ORGANISM: Homo sapiens

<400> SEQUENCE: 339
cgcuggcgac gggacauuau uacuuuuggu acgcgcugug acacuucaaa cucguaccgu 60
gaguaauaau gcgccgucca cggca 85

<210> SEQ ID NO 340
<211> LENGTH: 85
<212> TYPE: RNA
<213> ORGANISM: Homo sapiens

<400> SEQUENCE: 340
augguguuau caaguguaac agcaacucca uguggacugu guaccaauuu ccaguggaga 60
ugcuguuacu uuugaugguu accaa 85

<210> SEQ ID NO 341
<211> LENGTH: 85
<212> TYPE: RNA
<213> ORGANISM: Homo sapiens

<400> SEQUENCE: 341
ugguucccgc ccccuguaac agcaacucca uguggaagug cccacugguu ccaguggggc 60
ugcuguuauc uggggcgagg gccag 85

<210> SEQ ID NO 342
<211> LENGTH: 95
<212> TYPE: RNA
<213> ORGANISM: Homo sapiens

<400> SEQUENCE: 342
ggucucugug uugggcgucu gucugcccgc augccugccu cucuguugcu cugaaggagg 60
caggggcugg gccugcagcu gccugggcag agcgg 95

<210> SEQ ID NO 343
<211> LENGTH: 98
<212> TYPE: RNA
<213> ORGANISM: Homo sapiens

<400> SEQUENCE: 343
uugaggccuu aaaguacugu agcagcacau caugguuuac augcuacagu caagaugcga 60
aucauuauuu gcugcucuag aaauuuaagg aaauucau 98

<210> SEQ ID NO 344
<211> LENGTH: 67
<212> TYPE: RNA

<213> ORGANISM: Homo sapiens

<400> SEQUENCE: 344
ucuccaacaa uauccuggug cugagugaug acucaggcga cuccagcauc agugauuuug 60
uugaaga 67

<210> SEQ ID NO 345
<211> LENGTH: 110
<212> TYPE: RNA
<213> ORGANISM: Homo sapiens

<400> SEQUENCE: 345
aaagauccuc agacaaucca ugugcuucuc uuguccuuca uuccaccgga gucugucuca 60
uacccaacca gauuucagug gagugaaguu caggaggcau ggagcugaca 110

<210> SEQ ID NO 346
<211> LENGTH: 75
<212> TYPE: RNA
<213> ORGANISM: Homo sapiens

<400> SEQUENCE: 346
gugagggcau gcaggccugg auggggcagc ugggaugguc caaaagggug gccucaccag 60
cccuguguuc ccuag 75

<210> SEQ ID NO 347
<211> LENGTH: 88
<212> TYPE: RNA
<213> ORGANISM: Homo sapiens

<400> SEQUENCE: 347
aacugcccuc aaggagcuua caaucuagcu gggggguaaau gacuugcaca ugaacacaac 60
uagacuguga gcuucuagag ggcaggga 88

<210> SEQ ID NO 348
<211> LENGTH: 91
<212> TYPE: RNA
<213> ORGANISM: Homo sapiens

<400> SEQUENCE: 348
cuguguguga ugagcuggca guguauuguu agcugguuga auaugugaau ggcaucggcu 60
aacaugcaac ugcugucuua uugcauauac a 91

<210> SEQ ID NO 349
<211> LENGTH: 90
<212> TYPE: RNA
<213> ORGANISM: Homo sapiens

<400> SEQUENCE: 349
gagagaagca cuggacuuag ggucagaagg ccugagucuc ucugcugcag augggcucuc 60
ugucccugag ccaagcuuug uccucccugg 90

<210> SEQ ID NO 350
<211> LENGTH: 95
<212> TYPE: RNA
<213> ORGANISM: Homo sapiens

<400> SEQUENCE: 350
uuguaccugg ugugauuaua aagcaaugag acugauuguc auaugucguu ugugggaucc 60
gucucaguua cuuuauagcc auaccuggua ucuua 95

<210> SEQ ID NO 351
<211> LENGTH: 83
<212> TYPE: RNA
<213> ORGANISM: Homo sapiens

<400> SEQUENCE: 351
gcccuagcuu gguucuaaau cccauggugc cuucuccuug ggaaaaacag agaaggcacu 60
augagauuua gaaucaaguu agg 83

<210> SEQ ID NO 352
<211> LENGTH: 87
<212> TYPE: RNA
<213> ORGANISM: Homo sapiens

<400> SEQUENCE: 352
ucucaggcug ugucccucua gagggaagcg cuuucuguug ucugaaagaa aagaaaaugg 60
uucccuuuag aguguuacgc uuugaga 87

<210> SEQ ID NO 353
<211> LENGTH: 93
<212> TYPE: RNA
<213> ORGANISM: Homo sapiens

<400> SEQUENCE: 353
ccuuccggcg ucccaggcgg ggcgccgcgg gaccgcccuc gugucugugg cggugggauc 60
ccgcggccgu guuuuccugg uggcccggcc aug 93

<210> SEQ ID NO 354
<211> LENGTH: 89
<212> TYPE: RNA
<213> ORGANISM: Homo sapiens

<400> SEQUENCE: 354
ugcugcuggc cagagcucuu uucacauugu gcuacugucu gcaccuguca cuagcagugc 60
aauguuaaaa gggcauuggc cguguagug 89

<210> SEQ ID NO 355
<211> LENGTH: 82
<212> TYPE: RNA
<213> ORGANISM: Homo sapiens

<400> SEQUENCE: 355
ggccugcccg acacucuuuc ccuguugcac uacuauaggc cgcugggaag cagugcaaug 60
augaaagggc aucggucagg uc 82

<210> SEQ ID NO 356
<211> LENGTH: 86
<212> TYPE: RNA
<213> ORGANISM: Homo sapiens

<400> SEQUENCE: 356
auuaggagag uaucuucucu guuuuggcca ugugugugacu cacagccccu cacacauggc 60
cgaaacagag aaguuacuuu ccuaau 86

<210> SEQ ID NO 357
<211> LENGTH: 95
<212> TYPE: RNA
<213> ORGANISM: Homo sapiens

<400> SEQUENCE: 357
gucgaggccg uggcccggaa gugguucgggg ccgcugcggg cggaagggcg ccugugcuuc 60
guccgcucgg cgguggccca gccaggcccg cggga 95

<210> SEQ ID NO 358
<211> LENGTH: 98
<212> TYPE: RNA
<213> ORGANISM: Homo sapiens

<400> SEQUENCE: 358
uggccgacgg ggcgcgcgcg gccuggaggg gcggggcgga cgcagagccg cguuuagucu 60
aucgcugcgg uugcgagcgc uguagggagc cugugcug 98

<210> SEQ ID NO 359
<211> LENGTH: 81
<212> TYPE: RNA
<213> ORGANISM: Homo sapiens

<400> SEQUENCE: 359
ggguaagugg aaagauggug ggccgcagaa caugugcuga guucgugcca uaugucugcu 60
gaccaucacc uuuagaagcc c 81

<210> SEQ ID NO 360
<211> LENGTH: 110
<212> TYPE: RNA
<213> ORGANISM: Homo sapiens

<400> SEQUENCE: 360
ggcuacaguc uuucuucaug ugacucgugg acuucccuuu gucauccuau gccugagaau 60
auaugaagga ggcugggaag gcaaagggac guucaauugu caucacuggc 110

<210> SEQ ID NO 361
<211> LENGTH: 81
<212> TYPE: RNA
<213> ORGANISM: Homo sapiens

<400> SEQUENCE: 361
gggcuuucaa gucacuagug guuccguuua guagaugauu gugcauuguu ucaaaauggu 60
gcccuaguga cuacaaagcc c 81

<210> SEQ ID NO 362
<211> LENGTH: 97
<212> TYPE: RNA
<213> ORGANISM: Homo sapiens

<400> SEQUENCE: 362
uuagguaauu ccuccacuca aaacccuuca gugacuucca ugacaugaaa uaggaaguca 60
uuggaggguu ugagcagagg aaugaccugu uuuaaaa 97

<210> SEQ ID NO 363
<211> LENGTH: 85
<212> TYPE: RNA
<213> ORGANISM: Homo sapiens

<400> SEQUENCE: 363
ccuuagcaga gcuguggagu gugacaaugg uguuuguguc uaaacuauca aacgccauua 60
ucacacuaaa uagcuacugc uaggc 85

<210> SEQ ID NO 364
<211> LENGTH: 63
<212> TYPE: RNA
<213> ORGANISM: Homo sapiens

<400> SEQUENCE: 364
aagaaauggu uuaccguccc acauacauuu ugaauaugua ugugggaugg uaaaccgcuu 60
cuu 63

<210> SEQ ID NO 365
<211> LENGTH: 80
<212> TYPE: RNA
<213> ORGANISM: Homo sapiens

<400> SEQUENCE: 365
ccuguugcca caaacccgua gauccgaacu ugugguauua guccgcacaa gcuuguaucu 60
auagguaugu gucuguuagg 80

<210> SEQ ID NO 366
<211> LENGTH: 99
<212> TYPE: RNA
<213> ORGANISM: Homo sapiens

<400> SEQUENCE: 366
cccuggcaug guguggguggg gcagcuggug uugugaauca ggccguugcc aaucagagaa 60
cggcuacuuc acaacaccag ggccacacca cacuacagg 99

<210> SEQ ID NO 367
<211> LENGTH: 100
<212> TYPE: RNA
<213> ORGANISM: Homo sapiens

<400> SEQUENCE: 367
ugugucucuc ucuguguccu gccagugguu uuacccuaug guagguuacg ucaugcuguu 60
cuaccacagg guagaaccac ggacaggaua ccggggcacc 100

<210> SEQ ID NO 368
<211> LENGTH: 64
<212> TYPE: RNA
<213> ORGANISM: Homo sapiens

<400> SEQUENCE: 368
ccccgcgacg agccccucgc acaaaccgga ccugagcguu uuguucguuc ggcucgcgug 60
aggc 64

<210> SEQ ID NO 369
<211> LENGTH: 110
<212> TYPE: RNA
<213> ORGANISM: Homo sapiens

<400> SEQUENCE: 369
aguauaauua uuacauaguu uuugaugucg cagauacugc aucaggaacu gauuggauaa 60
gaaucaguca ccaucaguuc cuaaugcauu gccuucagca ucuaaacaag 110

<210> SEQ ID NO 370
<211> LENGTH: 67
<212> TYPE: RNA
<213> ORGANISM: Homo sapiens

<400> SEQUENCE: 370

-continued gugggccuca aauguggagc acuauucuga uguccaagug gaaagugcug cgacauuuga 60
gcgucac 67

<210> SEQ ID NO 371
<211> LENGTH: 78
<212> TYPE: RNA
<213> ORGANISM: Homo sapiens

<400> SEQUENCE: 371
uggccgauuu uggcacuagc acauuuuugc uugugucucu ccgcucugag caaucaugug 60
cagugccaau augggaaa 78

<210> SEQ ID NO 372
<211> LENGTH: 97
<212> TYPE: RNA
<213> ORGANISM: Homo sapiens

<400> SEQUENCE: 372
ugugaucacu gucuccagcc ugcugaagcu cagagggcuc ugauucagaa agaucaucgg 60
auccgucuga gcuuggcugg ucggaagucu caucauc 97

<210> SEQ ID NO 373
<211> LENGTH: 97
<212> TYPE: RNA
<213> ORGANISM: Homo sapiens

<400> SEQUENCE: 373
cacucugcug uggccuaugg cuuuucauuc cuaugugauu gcugucccaa acucauguag 60
ggcuaaaagc caugggcuac agugaggggc gagcucc 97

<210> SEQ ID NO 374
<211> LENGTH: 75
<212> TYPE: RNA
<213> ORGANISM: Homo sapiens

<400> SEQUENCE: 374
ugcccuggcu caguuaucac agugcugaug cugucuauuc uaaagguaca guacugugau 60
aacugaagga uggca 75

<210> SEQ ID NO 375
<211> LENGTH: 79
<212> TYPE: RNA
<213> ORGANISM: Homo sapiens

<400> SEQUENCE: 375
acuguccuuu uucgguuauc augguaccga ugcuguauau cugaaaggua caguacugug 60
auaacugaag aaugguggu 79

<210> SEQ ID NO 376
<211> LENGTH: 95
<212> TYPE: RNA
<213> ORGANISM: Homo sapiens

<400> SEQUENCE: 376
cucaucuguc uguugggcug gaggcagggc cuuugugaag gcggguggug cucagaucgc 60
cucugggccc uuccuccagc cccgaggcgg auuca 95

<210> SEQ ID NO 377
<211> LENGTH: 83

<212> TYPE: RNA
<213> ORGANISM: Homo sapiens

<400> SEQUENCE: 377
cugacuaugc cuccccgcau ccccuagggc auugguguaa agcuggagac ccacugcccc 60
aggugcugcu gggggguugua guc 83

<210> SEQ ID NO 378
<211> LENGTH: 83
<212> TYPE: RNA
<213> ORGANISM: Homo sapiens

<400> SEQUENCE: 378
cugacuaugc cuccccgcau ccccuagggc auugguguaa agcuggagac ccacugcccc 60
aggugcugcu gggggguugua guc 83

<210> SEQ ID NO 379
<211> LENGTH: 94
<212> TYPE: RNA
<213> ORGANISM: Homo sapiens

<400> SEQUENCE: 379
uguuuugagc gggggucaag agcaauaacg aaaaauguuu gucauaaacc guuuuucauu 60
auugcuccug accuccucuc auuugcuaua uuca 94

<210> SEQ ID NO 380
<211> LENGTH: 95
<212> TYPE: RNA
<213> ORGANISM: Homo sapiens

<400> SEQUENCE: 380
cggccggccc ugggguccauc uuccaguaca guguuggaug gucuaauugu gaagcuccua 60
acacugucug guaaagaugg cucccgggug gguuc 95

<210> SEQ ID NO 381
<211> LENGTH: 17
<212> TYPE: RNA
<213> ORGANISM: Homo sapiens

<400> SEQUENCE: 381
gugggggaga ggcuguc 17

<210> SEQ ID NO 382
<211> LENGTH: 22
<212> TYPE: RNA
<213> ORGANISM: Homo sapiens

<400> SEQUENCE: 382
ugcaacgaac cugagccacu ga 22

<210> SEQ ID NO 383
<211> LENGTH: 22
<212> TYPE: RNA
<213> ORGANISM: Homo sapiens

<400> SEQUENCE: 383
uagguuaucc guguugccuu cg 22

<210> SEQ ID NO 384
<211> LENGTH: 21
<212> TYPE: RNA

-continued

<213> ORGANISM: Homo sapiens

<400> SEQUENCE: 384
gugccagcug caguggggga g 21

<210> SEQ ID NO 385
<211> LENGTH: 20
<212> TYPE: RNA
<213> ORGANISM: Homo sapiens

<400> SEQUENCE: 385
guccgcucgg cgguggccca 20

<210> SEQ ID NO 386
<211> LENGTH: 23
<212> TYPE: RNA
<213> ORGANISM: Homo sapiens

<400> SEQUENCE: 386
ccaguuaccg cuuccgcuac cgc 23

<210> SEQ ID NO 387
<211> LENGTH: 17
<212> TYPE: RNA
<213> ORGANISM: Homo sapiens

<400> SEQUENCE: 387
acauugccag ggaguuu 17

<210> SEQ ID NO 388
<211> LENGTH: 22
<212> TYPE: RNA
<213> ORGANISM: Homo sapiens

<400> SEQUENCE: 388
uugcauaguc acaaaaguga uc 22

<210> SEQ ID NO 389
<211> LENGTH: 17
<212> TYPE: RNA
<213> ORGANISM: Homo sapiens

<400> SEQUENCE: 389
uugucugcug aguuucc 17

<210> SEQ ID NO 390
<211> LENGTH: 23
<212> TYPE: RNA
<213> ORGANISM: Homo sapiens

<400> SEQUENCE: 390
agguuacccg agcaacuuug cau 23

<210> SEQ ID NO 391
<211> LENGTH: 22
<212> TYPE: RNA
<213> ORGANISM: Homo sapiens

<400> SEQUENCE: 391
ugggucuuug cgggcgagau ga 22

<210> SEQ ID NO 392
<211> LENGTH: 19

<212> TYPE: RNA
<213> ORGANISM: Homo sapiens

<400> SEQUENCE: 392
aagugugcag ggcacuggu 19

<210> SEQ ID NO 393
<211> LENGTH: 22
<212> TYPE: RNA
<213> ORGANISM: Homo sapiens

<400> SEQUENCE: 393
uaaugccccu aaaaauccuu au 22

<210> SEQ ID NO 394
<211> LENGTH: 23
<212> TYPE: RNA
<213> ORGANISM: Homo sapiens

<400> SEQUENCE: 394
uaauccuugc uaccugggug aga 23

<210> SEQ ID NO 395
<211> LENGTH: 22
<212> TYPE: RNA
<213> ORGANISM: Homo sapiens

<400> SEQUENCE: 395
aguggggaac ccuuccauga gg 22

<210> SEQ ID NO 396
<211> LENGTH: 22
<212> TYPE: RNA
<213> ORGANISM: Homo sapiens

<400> SEQUENCE: 396
acaguagucu gcacauuggu ua 22

<210> SEQ ID NO 397
<211> LENGTH: 22
<212> TYPE: RNA
<213> ORGANISM: Homo sapiens

<400> SEQUENCE: 397
acaguagucu gcacauuggu ua 22

<210> SEQ ID NO 398
<211> LENGTH: 23
<212> TYPE: RNA
<213> ORGANISM: Homo sapiens

<400> SEQUENCE: 398
cccaguguuc agacuaccug uuc 23

<210> SEQ ID NO 399
<211> LENGTH: 23
<212> TYPE: RNA
<213> ORGANISM: Homo sapiens

<400> SEQUENCE: 399
cccaguguuc agacuaccug uuc 23

<210> SEQ ID NO 400

<211> LENGTH: 21
<212> TYPE: RNA
<213> ORGANISM: Homo sapiens

<400> SEQUENCE: 400
auuugugcuu ggcucuguca c 21

<210> SEQ ID NO 401
<211> LENGTH: 23
<212> TYPE: RNA
<213> ORGANISM: Homo sapiens

<400> SEQUENCE: 401
aaagugcugc gacauuugag cgu 23

<210> SEQ ID NO 402
<211> LENGTH: 23
<212> TYPE: RNA
<213> ORGANISM: Homo sapiens

<400> SEQUENCE: 402
gaagugcuuc gauuuugggg ugu 23

<210> SEQ ID NO 403
<211> LENGTH: 22
<212> TYPE: RNA
<213> ORGANISM: Homo sapiens

<400> SEQUENCE: 403
ucuucucugu uuuggccaug ug 22

<210> SEQ ID NO 404
<211> LENGTH: 22
<212> TYPE: RNA
<213> ORGANISM: Homo sapiens

<400> SEQUENCE: 404
uggguggucu ggagauuugu gc 22

<210> SEQ ID NO 405
<211> LENGTH: 23
<212> TYPE: RNA
<213> ORGANISM: Homo sapiens

<400> SEQUENCE: 405
uaaggugcau cuagugcaga uag 23

<210> SEQ ID NO 406
<211> LENGTH: 23
<212> TYPE: RNA
<213> ORGANISM: Homo sapiens

<400> SEQUENCE: 406
gagggucuug ggagggaugu gac 23

<210> SEQ ID NO 407
<211> LENGTH: 21
<212> TYPE: RNA
<213> ORGANISM: Homo sapiens

<400> SEQUENCE: 407
agaggauacc cuuuguaugu u 21

<210> SEQ ID NO 408
<211> LENGTH: 20
<212> TYPE: RNA
<213> ORGANISM: Homo sapiens

<400> SEQUENCE: 408
uaaagagccc uguggagaca 20

<210> SEQ ID NO 409
<211> LENGTH: 22
<212> TYPE: RNA
<213> ORGANISM: Homo sapiens

<400> SEQUENCE: 409
aacuggcccu caaagucccg cu 22

<210> SEQ ID NO 410
<211> LENGTH: 20
<212> TYPE: RNA
<213> ORGANISM: Homo sapiens

<400> SEQUENCE: 410
cuuccucguc ugucugcccc 20

<210> SEQ ID NO 411
<211> LENGTH: 21
<212> TYPE: RNA
<213> ORGANISM: Homo sapiens

<400> SEQUENCE: 411
uuaauaucgg acaaccauug u 21

<210> SEQ ID NO 412
<211> LENGTH: 22
<212> TYPE: RNA
<213> ORGANISM: Homo sapiens

<400> SEQUENCE: 412
gccugcuggg guggaaccug gu 22

<210> SEQ ID NO 413
<211> LENGTH: 22
<212> TYPE: RNA
<213> ORGANISM: Homo sapiens

<400> SEQUENCE: 413
caaaaaccac aguuucuuuu gc 22

<210> SEQ ID NO 414
<211> LENGTH: 80
<212> TYPE: RNA
<213> ORGANISM: Homo sapiens

<400> SEQUENCE: 414
ccucugugag aaagggugug ggggagaggc ugucuugugu cuguaaguau gccaaacuua 60
uuuuccccaa ggcagaggga 80

<210> SEQ ID NO 415
<211> LENGTH: 79
<212> TYPE: RNA
<213> ORGANISM: Homo sapiens

<400> SEQUENCE: 415

```
ccuuaauccu ugcaacgaac cugagccacu gauucaguaa aauacucagu ggcacauguu    60

uguugugagg gucaaaaga                                                 79

<210> SEQ ID NO 416
<211> LENGTH: 84
<212> TYPE: RNA
<213> ORGANISM: Homo sapiens

<400> SEQUENCE: 416

gugguacuug aagauagguu auccguguug ccuucgcuuu auuugugacg aaucauacac    60

gguugaccua uuuuucagua ccaa                                           84

<210> SEQ ID NO 417
<211> LENGTH: 83
<212> TYPE: RNA
<213> ORGANISM: Homo sapiens

<400> SEQUENCE: 417

ccugcugcag aggugccagc ugcagugggg gaggcacugc cagggcugcc cacucugcuu    60

agccagcagg ugccaagaac agg                                            83

<210> SEQ ID NO 418
<211> LENGTH: 95
<212> TYPE: RNA
<213> ORGANISM: Homo sapiens

<400> SEQUENCE: 418

gucgaggccg uggcccggaa guggucgggg ccgcugcggg cggaagggcg ccugugcuuc    60

guccgcucgg cgguggccca gccaggcccg cggga                               95

<210> SEQ ID NO 419
<211> LENGTH: 91
<212> TYPE: RNA
<213> ORGANISM: Homo sapiens

<400> SEQUENCE: 419

ggcgggggcg cgggcggcag uggcgggagc ggccccucgg ccauccuccg ucugcccagu    60

uaccgcuucc gcuaccgccg ccgcucccgc u                                   91

<210> SEQ ID NO 420
<211> LENGTH: 65
<212> TYPE: RNA
<213> ORGANISM: Homo sapiens

<400> SEQUENCE: 420

aaaaggcgag acauugccag ggaguuuauu uuguagcucu cuugauaaaa uguuuuagca    60

aacac                                                                65

<210> SEQ ID NO 421
<211> LENGTH: 90
<212> TYPE: RNA
<213> ORGANISM: Homo sapiens

<400> SEQUENCE: 421

cucacagcug ccagugucau uuuugugauc ugcagcuagu auucucacuc caguugcaua    60

gucacaaaag ugaucauugg cagguguggc                                     90

<210> SEQ ID NO 422
<211> LENGTH: 87
```

<212> TYPE: RNA
<213> ORGANISM: Homo sapiens

<400> SEQUENCE: 422
agcgguggcc agugucauuu uugugauguu gcagcuagua auaugagccc aguugcauag 60
ucacaaaagu gaucauugga aacugug 87

<210> SEQ ID NO 423
<211> LENGTH: 67
<212> TYPE: RNA
<213> ORGANISM: Homo sapiens

<400> SEQUENCE: 423
auggaggugg agagucauca gcagcacuga gcaggcagug uugucugcug aguuuccacg 60
ucauuug 67

<210> SEQ ID NO 424
<211> LENGTH: 79
<212> TYPE: RNA
<213> ORGANISM: Homo sapiens

<400> SEQUENCE: 424
ugguacucgg ggagagguua cccgagcaac uuugcaucug gacgacgaau guugcucggu 60
gaaccccuuu ucgguauca 79

<210> SEQ ID NO 425
<211> LENGTH: 88
<212> TYPE: RNA
<213> ORGANISM: Homo sapiens

<400> SEQUENCE: 425
cgaggauggg agcugagggc ugggucuuug cgggcgagau gagggugucg gaucaacugg 60
ccuacaaagu cccaguucuc ggcccccg 88

<210> SEQ ID NO 426
<211> LENGTH: 94
<212> TYPE: RNA
<213> ORGANISM: Homo sapiens

<400> SEQUENCE: 426
aucacagaca ccuccaagug ugcagggcac uggugggggc cggggcaggc ccagcgaaag 60
ugcaggaccu ggcacuuagu cggaagugag ggug 94

<210> SEQ ID NO 427
<211> LENGTH: 87
<212> TYPE: RNA
<213> ORGANISM: Homo sapiens

<400> SEQUENCE: 427
accgcaggga aaaugaggga cuuuuggggg cagauguguu uccauuccac uaucauaaug 60
ccccuaaaaa uccuuauugc ucuugca 87

<210> SEQ ID NO 428
<211> LENGTH: 84
<212> TYPE: RNA
<213> ORGANISM: Homo sapiens

<400> SEQUENCE: 428
gcucccccuc ucuaauccuu gcuaccuggg ugagagugcu gucugaaugc aaugcaccug 60
ggcaaggauu cugagagcga gagc 84

<210> SEQ ID NO 429
<211> LENGTH: 84
<212> TYPE: RNA
<213> ORGANISM: Homo sapiens

<400> SEQUENCE: 429
uugacuuagc uggguagugg ggaacccuuc caugaggagu agaacacucc uuaugcaaga 60
uucccuucua ccuggcuggg uugg 84

<210> SEQ ID NO 430
<211> LENGTH: 71
<212> TYPE: RNA
<213> ORGANISM: Homo sapiens

<400> SEQUENCE: 430
gccaacccag uguucagacu accuguucag gaggcucuca auguguacag uagucugcac 60
auugguuagg c 71

<210> SEQ ID NO 431
<211> LENGTH: 110
<212> TYPE: RNA
<213> ORGANISM: Homo sapiens

<400> SEQUENCE: 431
aggaagcuuc uggagauccu gcuccgucgc cccaguguuc agacuaccug uucaggacaa 60
ugccguugua caguagucug cacauugguu agacugggca agggagagca 110

<210> SEQ ID NO 432
<211> LENGTH: 71
<212> TYPE: RNA
<213> ORGANISM: Homo sapiens

<400> SEQUENCE: 432
gccaacccag uguucagacu accuguucag gaggcucuca auguguacag uagucugcac 60
auugguuagg c 71

<210> SEQ ID NO 433
<211> LENGTH: 110
<212> TYPE: RNA
<213> ORGANISM: Homo sapiens

<400> SEQUENCE: 433
aggaagcuuc uggagauccu gcuccgucgc cccaguguuc agacuaccug uucaggacaa 60
ugccguugua caguagucug cacauugguu agacugggca agggagagca 110

<210> SEQ ID NO 434
<211> LENGTH: 91
<212> TYPE: RNA
<213> ORGANISM: Homo sapiens

<400> SEQUENCE: 434
uuuucaaagc aaugugugac agguacaggg acaaaucccg uuaauaagua agaggauuug 60
ugcuuggcuc ugucacaugc cacuuugaaa a 91

<210> SEQ ID NO 435
<211> LENGTH: 67
<212> TYPE: RNA
<213> ORGANISM: Homo sapiens

<400> SEQUENCE: 435
gugggccuca aauguggagc acuauucuga uguccaagug gaaagugcug cgacauuuga 60
gcgucac 67

<210> SEQ ID NO 436
<211> LENGTH: 69
<212> TYPE: RNA
<213> ORGANISM: Homo sapiens

<400> SEQUENCE: 436
gggauacuca aaaugggggc gcuuuccuuu uugucuguac ugggaagugc uucgauuuug 60
gggugucc 69

<210> SEQ ID NO 437
<211> LENGTH: 86
<212> TYPE: RNA
<213> ORGANISM: Homo sapiens

<400> SEQUENCE: 437
auuaggagag uaucuucucu guuuuggcca ugugugacu cacagccccu cacacauggc 60
cgaaacagag aaguuacuuu ccuaau 86

<210> SEQ ID NO 438
<211> LENGTH: 71
<212> TYPE: RNA
<213> ORGANISM: Homo sapiens

<400> SEQUENCE: 438
agguuguucu gggugggucug gagauuugug cagcuuguac cugcacaaau cuccggacca 60
cuuagucuuu a 71

<210> SEQ ID NO 439
<211> LENGTH: 71
<212> TYPE: RNA
<213> ORGANISM: Homo sapiens

<400> SEQUENCE: 439
uguucuaagg ugcaucuagu gcagauagug aaguagauua gcaucuacug cccuaagugc 60
uccuucuggc a 71

<210> SEQ ID NO 440
<211> LENGTH: 97
<212> TYPE: RNA
<213> ORGANISM: Homo sapiens

<400> SEQUENCE: 440
gggacuuguc acugccuguc uccucccucu ccagcagcga cuggauucug gaguccaucu 60
agagggucuu gggagggaug ugacuguugg gaagccc 97

<210> SEQ ID NO 441
<211> LENGTH: 86
<212> TYPE: RNA
<213> ORGANISM: Homo sapiens

<400> SEQUENCE: 441
uuugguacuu gaagagagga uacccuuugu auguucacuu gauuaauggc gaauauacag 60
ggggagacuc uuauuugcgu aucaaa 86

<210> SEQ ID NO 442
<211> LENGTH: 86
<212> TYPE: RNA
<213> ORGANISM: Homo sapiens

<400> SEQUENCE: 442
uuugguacuu aaagagagga uacccuuugu auguucacuu gauuaauggc gaauauacag 60
ggggagacuc ucauuugcgu aucaaa 86

<210> SEQ ID NO 443
<211> LENGTH: 83
<212> TYPE: RNA
<213> ORGANISM: Homo sapiens

<400> SEQUENCE: 443
ccccagcuag guaaagagcc cuguggagac accuggauuc agagaacaug ucuccacuga 60
gcacuugggc cuugauggcg gcu 83

<210> SEQ ID NO 444
<211> LENGTH: 83
<212> TYPE: RNA
<213> ORGANISM: Homo sapiens

<400> SEQUENCE: 444
guggucucag aaucgggguu uugagggcga gaugaguuua uguuuuaucc aacuggcccu 60
caaagucccg cuuuuggggu cau 83

<210> SEQ ID NO 445
<211> LENGTH: 83
<212> TYPE: RNA
<213> ORGANISM: Homo sapiens

<400> SEQUENCE: 445
gugaguggga gccccagugu gugguugggg ccauggcggg ugggcagccc agccucugag 60
ccuuccucgu cugucugccc cag 83

<210> SEQ ID NO 446
<211> LENGTH: 79
<212> TYPE: RNA
<213> ORGANISM: Homo sapiens

<400> SEQUENCE: 446
gugcuuaaag aauggcuguc cguaguaugg ucucuauauu uaugaugauu aauaucggac 60
aaccauuguu uuaguaucc 79

<210> SEQ ID NO 447
<211> LENGTH: 75
<212> TYPE: RNA
<213> ORGANISM: Homo sapiens

<400> SEQUENCE: 447
agacagagaa gccaggucac gucucugcag uuacacagcu cacgagugcc ugcuggggug 60
gaaccugguc ugucu 75

<210> SEQ ID NO 448
<211> LENGTH: 97
<212> TYPE: RNA
<213> ORGANISM: Homo sapiens

<400> SEQUENCE: 448
aaacaaguua uauuagguug gugcaaaagu aauugugguu uuugccugua aaaguaaugg 60
caaaaaccac aguuucuuuu gcaccagacu aauaaag 97

<210> SEQ ID NO 449
<211> LENGTH: 22
<212> TYPE: RNA
<213> ORGANISM: Homo sapiens

<400> SEQUENCE: 449
acuuuaacau ggaagugcuu uc 22

<210> SEQ ID NO 450
<211> LENGTH: 23
<212> TYPE: RNA
<213> ORGANISM: Homo sapiens

<400> SEQUENCE: 450
aagugccgcc aucuuuugag ugu 23

<210> SEQ ID NO 451
<211> LENGTH: 22
<212> TYPE: RNA
<213> ORGANISM: Homo sapiens

<400> SEQUENCE: 451
ugugacuggu ugaccagagg gg 22

<210> SEQ ID NO 452
<211> LENGTH: 21
<212> TYPE: RNA
<213> ORGANISM: Homo sapiens

<400> SEQUENCE: 452
ugauugucca aacgcaauuc u 21

<210> SEQ ID NO 453
<211> LENGTH: 22
<212> TYPE: RNA
<213> ORGANISM: Homo sapiens

<400> SEQUENCE: 453
uagguuaucc guguugccuu cg 22

<210> SEQ ID NO 454
<211> LENGTH: 23
<212> TYPE: RNA
<213> ORGANISM: Homo sapiens

<400> SEQUENCE: 454
uuaaugcuaa ucgugauagg ggu 23

<210> SEQ ID NO 455
<211> LENGTH: 22
<212> TYPE: RNA
<213> ORGANISM: Homo sapiens

<400> SEQUENCE: 455
uauugcacau uacuaaguug ca 22

<210> SEQ ID NO 456
<211> LENGTH: 21
<212> TYPE: RNA

<213> ORGANISM: Homo sapiens

<400> SEQUENCE: 456
gugcauugua guugcauugc a 21

<210> SEQ ID NO 457
<211> LENGTH: 21
<212> TYPE: RNA
<213> ORGANISM: Homo sapiens

<400> SEQUENCE: 457
cauuauuacu uuugguacgc g 21

<210> SEQ ID NO 458
<211> LENGTH: 22
<212> TYPE: RNA
<213> ORGANISM: Homo sapiens

<400> SEQUENCE: 458
ucggauccgu cugagcuugg cu 22

<210> SEQ ID NO 459
<211> LENGTH: 22
<212> TYPE: RNA
<213> ORGANISM: Homo sapiens

<400> SEQUENCE: 459
uaacagucua cagccauggu cg 22

<210> SEQ ID NO 460
<211> LENGTH: 23
<212> TYPE: RNA
<213> ORGANISM: Homo sapiens

<400> SEQUENCE: 460
uuauugcuua agaauacgcg uag 23

<210> SEQ ID NO 461
<211> LENGTH: 23
<212> TYPE: RNA
<213> ORGANISM: Homo sapiens

<400> SEQUENCE: 461
uacccuguag aaccgaauuu gug 23

<210> SEQ ID NO 462
<211> LENGTH: 23
<212> TYPE: RNA
<213> ORGANISM: Homo sapiens

<400> SEQUENCE: 462
uguaguguuu ccuacuuuau gga 23

<210> SEQ ID NO 463
<211> LENGTH: 22
<212> TYPE: RNA
<213> ORGANISM: Homo sapiens

<400> SEQUENCE: 463
ucccugagac ccuaacuugu ga 22

<210> SEQ ID NO 464
<211> LENGTH: 22

<212> TYPE: RNA
<213> ORGANISM: Homo sapiens

<400> SEQUENCE: 464
uugcauaguc acaaaaguga uc 22

<210> SEQ ID NO 465
<211> LENGTH: 23
<212> TYPE: RNA
<213> ORGANISM: Homo sapiens

<400> SEQUENCE: 465
aacauucaac gcugucggug agu 23

<210> SEQ ID NO 466
<211> LENGTH: 22
<212> TYPE: RNA
<213> ORGANISM: Homo sapiens

<400> SEQUENCE: 466
ugagguagua gguuguauag uu 22

<210> SEQ ID NO 467
<211> LENGTH: 22
<212> TYPE: RNA
<213> ORGANISM: Homo sapiens

<400> SEQUENCE: 467
ugagguagua gguugugugg uu 22

<210> SEQ ID NO 468
<211> LENGTH: 21
<212> TYPE: RNA
<213> ORGANISM: Homo sapiens

<400> SEQUENCE: 468
aacauagagg aaauuccacg u 21

<210> SEQ ID NO 469
<211> LENGTH: 21
<212> TYPE: RNA
<213> ORGANISM: Homo sapiens

<400> SEQUENCE: 469
uugugcuuga ucuaaccaug u 21

<210> SEQ ID NO 470
<211> LENGTH: 20
<212> TYPE: RNA
<213> ORGANISM: Homo sapiens

<400> SEQUENCE: 470
uaaggcacgc ggugaaugcc 20

<210> SEQ ID NO 471
<211> LENGTH: 24
<212> TYPE: RNA
<213> ORGANISM: Homo sapiens

<400> SEQUENCE: 471
ucccugagac ccuuuaaccu guga 24

<210> SEQ ID NO 472

-continued

<211> LENGTH: 23
<212> TYPE: RNA
<213> ORGANISM: Homo sapiens

<400> SEQUENCE: 472
ucuuugguua ucuagcugua uga 23

<210> SEQ ID NO 473
<211> LENGTH: 23
<212> TYPE: RNA
<213> ORGANISM: Homo sapiens

<400> SEQUENCE: 473
uaaagugcuu auagugcagg uag 23

<210> SEQ ID NO 474
<211> LENGTH: 22
<212> TYPE: RNA
<213> ORGANISM: Homo sapiens

<400> SEQUENCE: 474
cagugcaaug uuaaaagggc au 22

<210> SEQ ID NO 475
<211> LENGTH: 23
<212> TYPE: RNA
<213> ORGANISM: Homo sapiens

<400> SEQUENCE: 475
aaagugcugc gacauuugag cgu 23

<210> SEQ ID NO 476
<211> LENGTH: 22
<212> TYPE: RNA
<213> ORGANISM: Homo sapiens

<400> SEQUENCE: 476
acucaaaaug ggggcgcuuu cc 22

<210> SEQ ID NO 477
<211> LENGTH: 22
<212> TYPE: RNA
<213> ORGANISM: Homo sapiens

<400> SEQUENCE: 477
uaacacuguc ugguaaagau gg 22

<210> SEQ ID NO 478
<211> LENGTH: 23
<212> TYPE: RNA
<213> ORGANISM: Homo sapiens

<400> SEQUENCE: 478
cccaguguuc agacuaccug uuc 23

<210> SEQ ID NO 479
<211> LENGTH: 23
<212> TYPE: RNA
<213> ORGANISM: Homo sapiens

<400> SEQUENCE: 479
agcuacauug ucugcugggu uuc 23

-continued

```
<210> SEQ ID NO 480
<211> LENGTH: 22
<212> TYPE: RNA
<213> ORGANISM: Homo sapiens

<400> SEQUENCE: 480

ugucaguuug ucaaauaccc ca                                    22


<210> SEQ ID NO 481
<211> LENGTH: 21
<212> TYPE: DNA
<213> ORGANISM: Homo sapiens

<400> SEQUENCE: 481

aagactgcgt tcgaatccat a                                     21
```